(12) United States Patent
Call et al.

(10) Patent No.: US 7,578,973 B2
(45) Date of Patent: Aug. 25, 2009

(54) DEVICES FOR CONTINUOUS SAMPLING OF AIRBORNE PARTICLES USING A REGENERATIVE SURFACE

(75) Inventors: Charles John Call, Albuquerque, NM (US); Ezra Merrill, Albuquerque, NM (US); Robert Beckius, Placitas, NM (US)

(73) Assignee: MesoSystems Technology, Inc., Albuquerque, NM (US)

(*) Notice: Subject to any disclaimer, the term of this patent is extended or adjusted under 35 U.S.C. 154(b) by 923 days.

(21) Appl. No.: 10/790,936

(22) Filed: Mar. 1, 2004

(65) Prior Publication Data

US 2004/0232052 A1 Nov. 25, 2004

Related U.S. Application Data

(63) Continuation-in-part of application No. 10/366,595, filed on Feb. 11, 2003, now Pat. No. 6,938,777, and a continuation-in-part of application No. 09/955,481, filed on Sep. 17, 2001, now Pat. No. 6,695,146, which is a continuation-in-part of application No. 09/265,620, filed on Mar. 10, 1999, now Pat. No. 6,363,800, and a continuation-in-part of application No. 09/494,962, filed on Jan. 31, 2000, now Pat. No. 6,290,065, which is a continuation-in-part of application No. 09/191,980, filed on Nov. 13, 1998, now Pat. No. 6,062,392.

(60) Provisional application No. 60/355,915, filed on Feb. 11, 2002.

(51) Int. Cl.
*G01N 7/02* (2006.01)

(52) U.S. Cl. .................. 422/83; 422/88; 436/165; 73/23.2; 340/539.26

(58) Field of Classification Search ............ 422/83, 422/88; 436/165; 73/23.2; 340/539.26
See application file for complete search history.

(56) References Cited

U.S. PATENT DOCUMENTS

| | | | |
|---|---|---|---|
| 3,001,914 A | 9/1961 | Andersen | 435/30 |
| 3,518,815 A | 7/1970 | McFarland et al | 73/863.22 |
| 3,572,128 A | 3/1971 | Hemeon | 73/863.24 |
| 3,633,405 A | 1/1972 | Noll | |
| 3,760,630 A | 9/1973 | Brumbaugh | 73/28.05 |

(Continued)

FOREIGN PATENT DOCUMENTS

EP 0 543 108 5/1993

(Continued)

OTHER PUBLICATIONS

Carrano, John. "*Ultraviolet Light*." Spies's Oe magazine, Jun. 2003, pp. 20-23.

(Continued)

*Primary Examiner*—Lyle A Alexander
(74) *Attorney, Agent, or Firm*—Ronald M. Anderson

(57) ABSTRACT

Airborne particles are impacted on a collection surface, analyzed, and then the collection surface is regenerated. Thus, the same collection surface can be used in numerous cycles. The analysis can be focused on one or more properties of interest, such as the concentration of airborne biologicals. Sensors based on regenerative collection surfaces may be incorporated in many networks for applications such as building automation.

27 Claims, 29 Drawing Sheets

U.S. PATENT DOCUMENTS

| | | | |
|---|---|---|---|
| 3,901,798 A | 8/1975 | Peterson | 209/143 |
| 3,922,905 A | 12/1975 | Roth, Thomas P | 73/28.04 |
| 3,972,226 A | 8/1976 | Rountree et al. | |
| 3,997,297 A | 12/1976 | Jenkins et al. | 23/232 E |
| 4,111,049 A | 9/1978 | Lerner et al. | 73/421.5 R |
| 4,301,002 A | 11/1981 | Loo | 209/143 |
| 4,473,384 A | 9/1984 | Lefkowitz | 55/290 |
| 4,580,440 A | 4/1986 | Reid et al. | 73/23 |
| 4,670,135 A | 6/1987 | Marple et al. | 209/143 |
| 4,697,462 A | 10/1987 | Daube, Jr. et al. | |
| 4,742,009 A * | 5/1988 | Beverly et al. | 436/57 |
| 4,764,186 A | 8/1988 | Langer | |
| 4,767,524 A | 8/1988 | Yeh et al. | 209/143 |
| 4,820,920 A | 4/1989 | Bather | 250/282 |
| 4,941,899 A | 7/1990 | Liu | |
| 4,942,297 A | 7/1990 | Johnson et al. | |
| 4,961,966 A | 10/1990 | Stevens et al. | 427/299 |
| 4,987,286 A | 1/1991 | Allen | 219/121.68 |
| 4,990,740 A | 2/1991 | Meyer | |
| 5,039,490 A | 8/1991 | Marsoner et al. | |
| 5,040,424 A | 8/1991 | Marple et al. | |
| 5,063,164 A | 11/1991 | Goldstein | |
| 5,128,539 A | 7/1992 | Rodgers et al. | |
| 5,254,861 A | 10/1993 | Carpenter et al. | |
| 5,299,141 A | 3/1994 | Hungerford et al. | 364/510 |
| 5,304,125 A | 4/1994 | Leith | 604/57 |
| 5,412,975 A | 5/1995 | Raabe et al. | |
| 5,425,802 A | 6/1995 | Burton et al. | |
| 5,472,645 A | 12/1995 | Rock et al. | |
| 5,498,271 A | 3/1996 | Marple et al. | |
| 5,512,216 A | 4/1996 | Rock et al. | |
| 5,533,406 A | 7/1996 | Geise | 73/863.22 |
| 5,553,795 A | 9/1996 | Tsai et al. | |
| 5,585,575 A | 12/1996 | Corrigan et al. | 73/863.71 |
| 5,760,314 A | 6/1998 | Bromberg et al. | 73/863.21 |
| 5,776,754 A | 7/1998 | Caldwell | 435/240.2 |
| 5,786,894 A | 7/1998 | Shields et al. | 356/338 |
| 5,859,375 A * | 1/1999 | Danylewych-May et al. | 73/864.71 |
| 5,932,795 A | 8/1999 | Koutrakis et al. | 73/28.01 |
| 5,949,001 A | 9/1999 | Willeke | 73/865.5 |
| 6,024,923 A | 2/2000 | Melendez et al. | |
| 6,062,392 A | 5/2000 | Birmingham et al. | 209/143 |
| 6,101,886 A | 8/2000 | Brenizer et al. | 73/863.23 |
| 6,110,247 A | 8/2000 | Birmingham et al. | 55/442 |
| 6,125,845 A | 10/2000 | Halvorsen et al. | 128/200.24 |
| 6,193,587 B1 | 2/2001 | Lin et al. | 451/56 |
| 6,194,731 B1 | 2/2001 | Jeys et al. | 250/461.2 |
| 6,217,636 B1 | 4/2001 | McFarland | 95/216 |
| 6,235,002 B1 | 5/2001 | Carver et al. | 604/183 |
| 6,240,768 B1 | 6/2001 | Lemmonier | 73/28.05 |
| 6,267,016 B1 | 7/2001 | Call et al. | |
| 6,276,016 B1 | 8/2001 | Springer | 14/71.1 |
| 6,284,025 B1 | 9/2001 | Kreisberg et al. | 95/267 |
| 6,324,927 B1 | 12/2001 | Ornath et al. | 73/863.11 |
| 6,334,365 B1 | 1/2002 | Linker et al. | 73/864.81 |
| 6,363,800 B1 | 4/2002 | Call et al. | |
| 6,435,043 B1 | 8/2002 | Ferguson et al. | 73/863.22 |
| 6,511,854 B1 | 1/2003 | Asanov et al. | |
| 6,573,836 B1 | 6/2003 | Gitis et al. | 340/603 |
| 6,695,146 B2 | 2/2004 | Call et al. | 73/863.22 |
| 6,707,539 B2 | 3/2004 | Selinfreund et al. | |
| 6,805,751 B2 | 10/2004 | Allen | 134/1 |
| 6,887,710 B2 * | 5/2005 | Call et al. | 436/53 |
| 6,908,567 B2 | 6/2005 | Uziel | 216/66 |
| 6,949,147 B2 | 9/2005 | Uziel et al. | 134/1 |
| 7,096,125 B2 | 8/2006 | Padmanabhan et al. | 702/24 |
| 7,265,669 B2 * | 9/2007 | Call et al. | 340/539.26 |
| 2002/0124664 A1 | 9/2002 | Call et al. | 73/863.22 |
| 2004/0028561 A1 | 2/2004 | Daugherty et al. | 422/99 |

FOREIGN PATENT DOCUMENTS

| | | |
|---|---|---|
| JP | 59196713 | 11/1984 |
| WO | WO 98/58725 | 12/1998 |
| WO | WO 03/089661 | 10/2003 |
| WO | WO 03/089907 | 10/2003 |

OTHER PUBLICATIONS

Cassarly, William. *"Taming Light." "Non-imaging optical systems focus on transferring light efficiently and controlling its distribution."* Oe magazine, 7pp. <http://www.oemagazine.com/fromTheMagazine/dec02/taminglight.html>.

Cousins, Daniel. *"Biodefense of Passenger Aircraft."* Biodefense Systems Group, MIT Lincoln Labroratory. Presented at FAA Center of Excellence. 23pp.

Foot, Virginia, E., et al. *"Characterising single airborne particles by fluorescence emission and spatial analysis of elastic scattered light."* Defence Science and Technology Lab. (United Kingdom) 2pp, 2005 Copyright SPIE-The international Society for Optical Engineering. <http://spiedl.aip.or/GetabsServlet?prog=normal&id=PSISDG00561700000....>.

Frye-Mason, Greg et al. *"Novel fluorescence-based integrated sensor for chemical and biological agent detection."* Nomadics, Inc. (USA) 2pp, 2005 Copyright SPIE-The international Society for Optical Engineering. <http://spiedl.aip.or/GetabsServlet?prog=normal&id=PSISDG00561700000....>.

Huston, Alan, L., et al. *"Optical classification of bioaerosols using UV fluorescence and IR absorption spectroscopy."* Naval Research Lab. (USA) 2pp, 2005 Copyright SPIE-The international Society for Optical Engineering. <http://spiedl.aip.or/GetabsServlet?prog=normal&id=PSISDG00561700000....>.

Jeys, T.H., L., et al. *"Development of UV LED based biosensor."* SPIE vol. 5071, 2003 Copyright SPIE., pp. 234-240.

Kaye, Paul, H., et al. *"A low-cost multi-channel aerosol fluorescence sensor for networked deployment."* University of Hertfordshire (UK) and Defence Science Technology Lab (UK) 11pp, 2005 Copyright SPIE-The international Society for Optical Engineering. <http://spiedl.aip.or/GetabsServlet?prog=normal&id=PSISDG00561700000....>.

* cited by examiner

MAJOR FLOW

MINOR FLOW

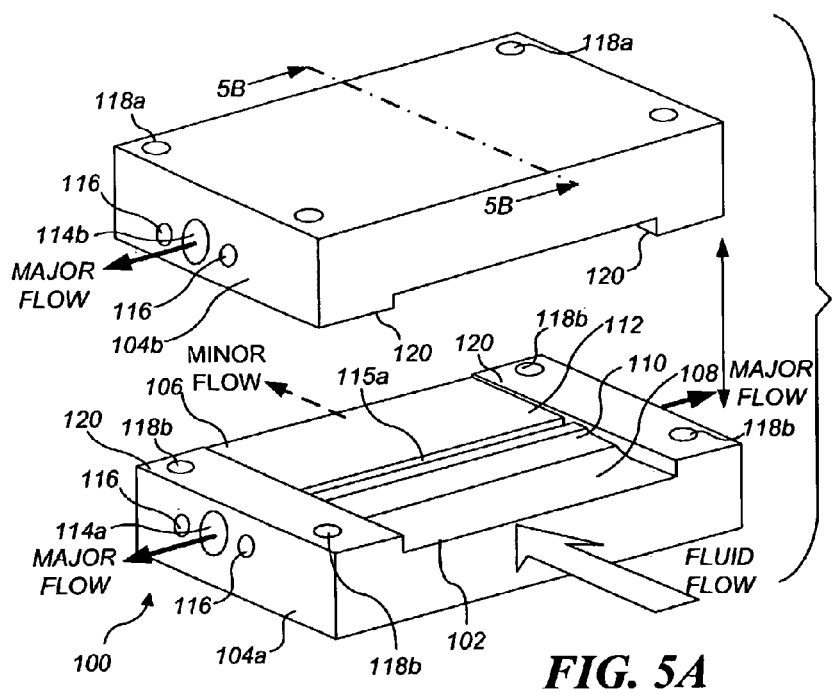
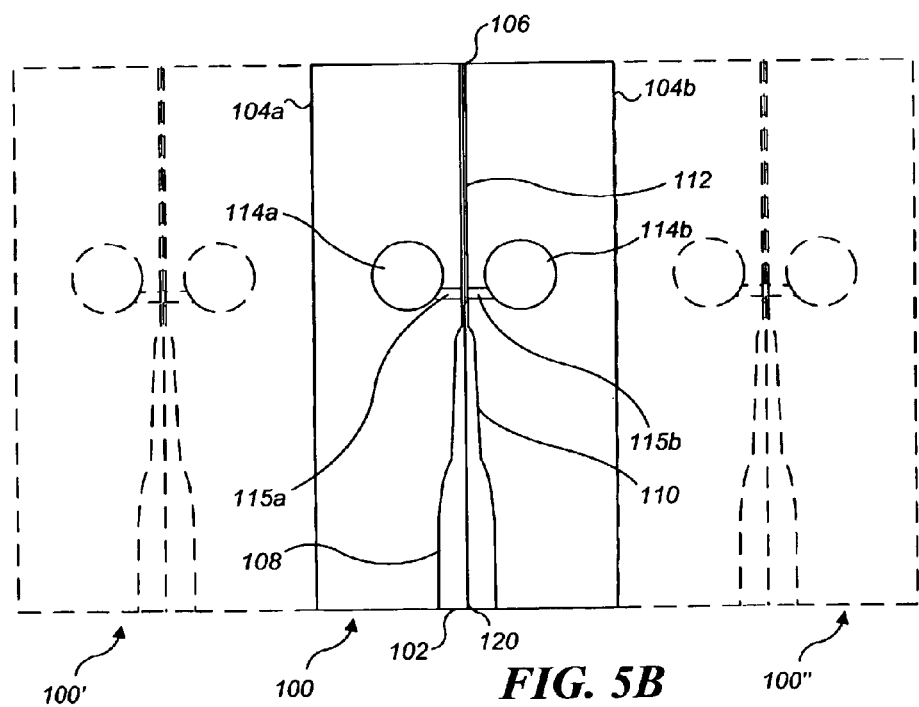

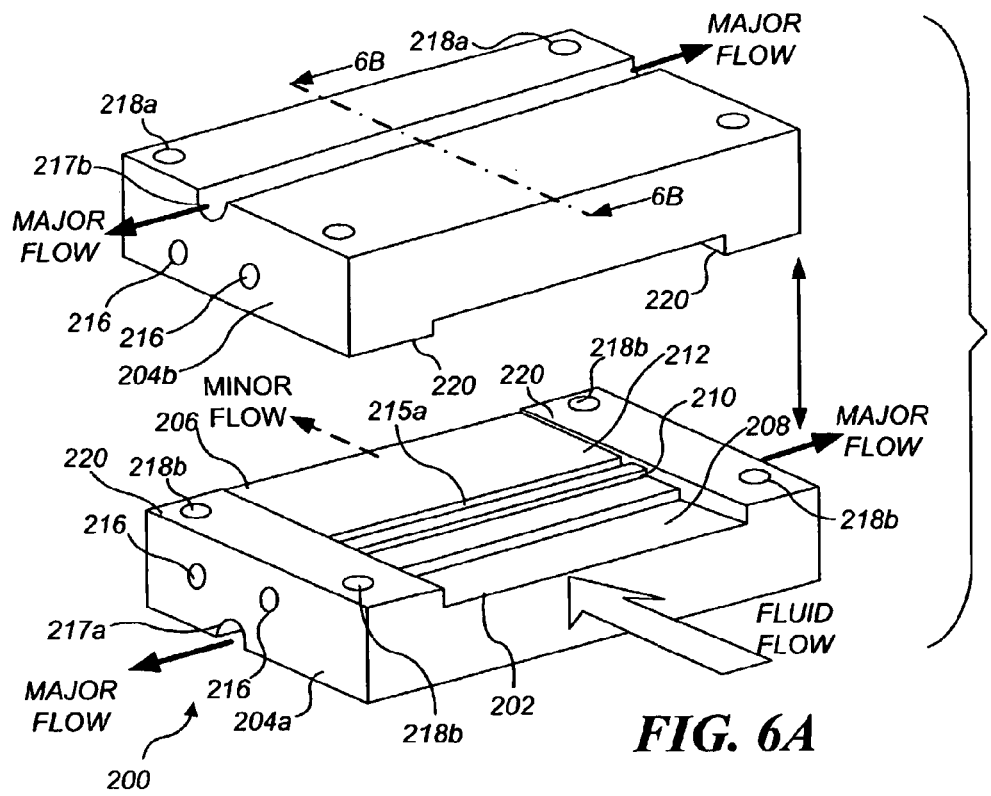
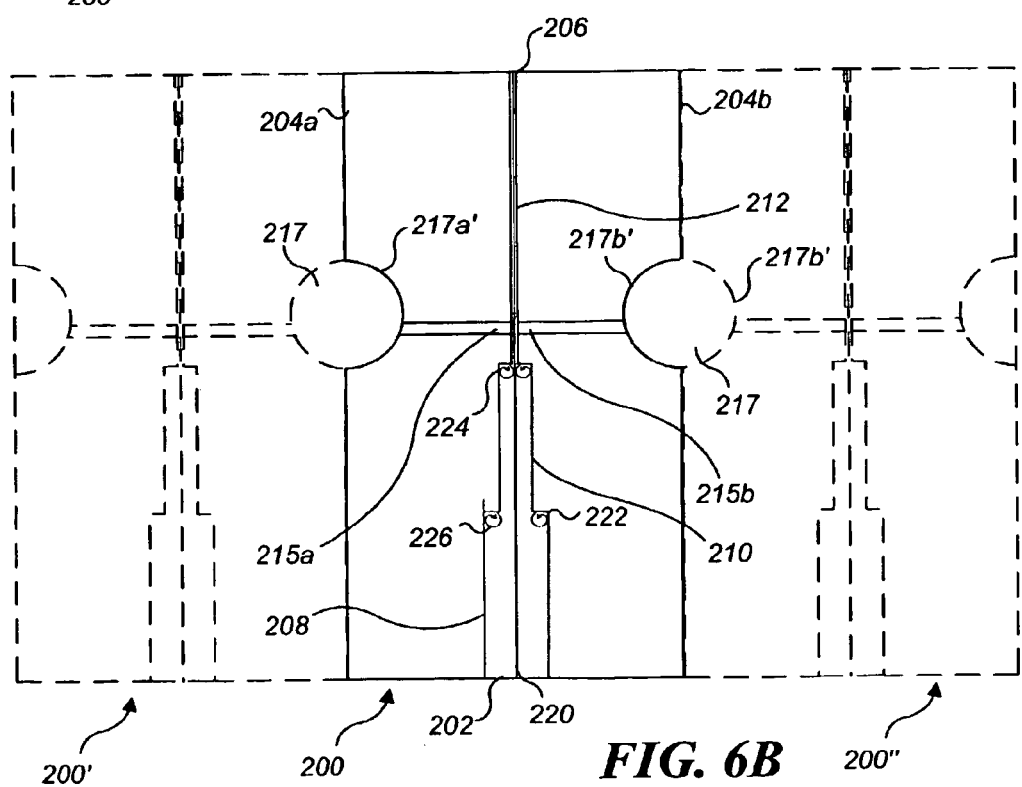

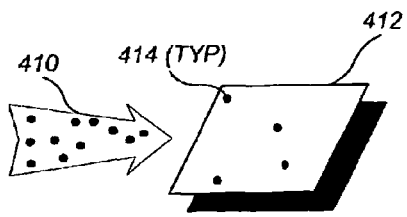
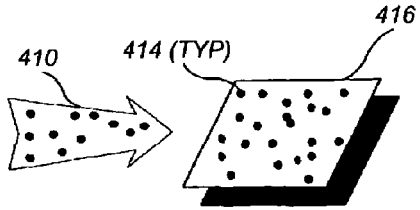
FIG. 10 (PRIOR ART)　　　FIG. 11
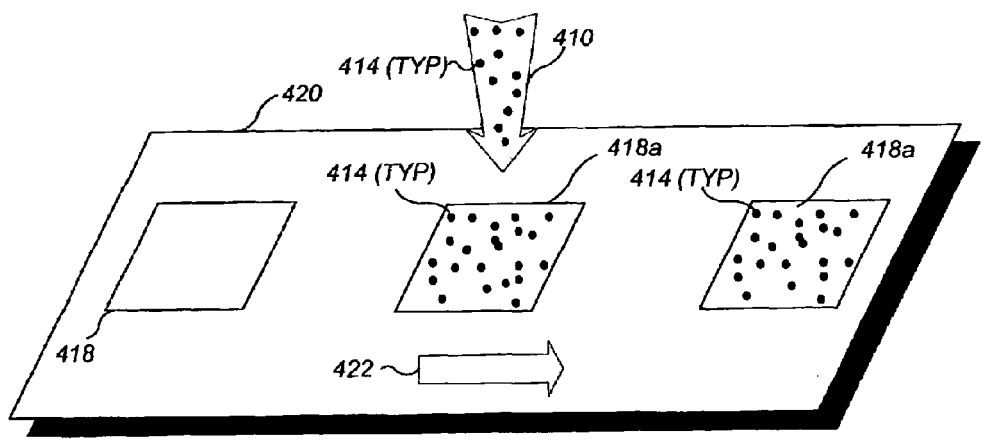
FIG. 12
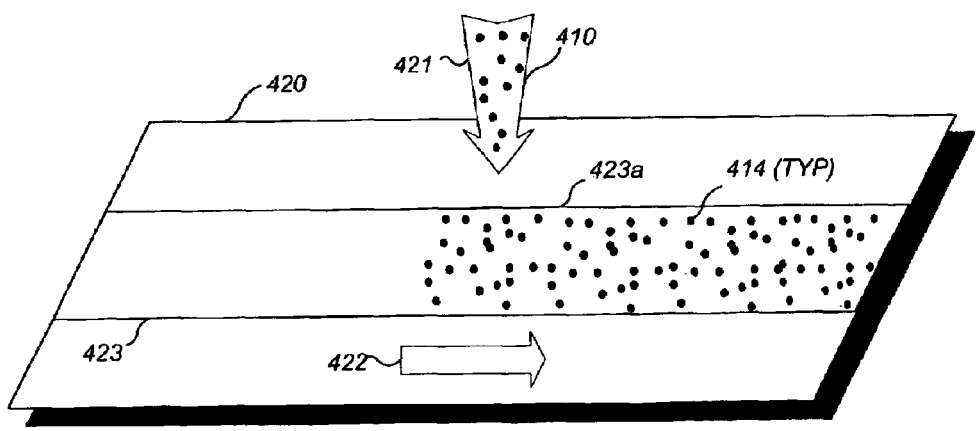
FIG. 13

2710
preconditioning air sample

2720
concentrating airborne particles of desirable size range

2740
depositing airborne particles on a collection surface

2730
moistening collection surface

2750
analyzing deposit on collection surface

2770
verifying regeneration

2760
regenerating the surface

FIG. 27

DEVICES FOR CONTINUOUS SAMPLING OF AIRBORNE PARTICLES USING A REGENERATIVE SURFACE

RELATED APPLICATIONS

This application is a continuation in part of a prior application Ser. No. 10/366,595, filed Feb. 11, 2003 now U.S. Pat. No. 6,938,777, which is based on a prior provisional application Ser. No. 60/355,915, filed on Feb. 11, 2002, and is further a continuation in part of a prior application Ser. No. 09/955,481, filed on Sep. 17, 2001 now U.S. Pat. No. 6,695,146, which is a continuation-in-part of prior utility application Ser. No. 09/265,620, filed on Mar. 10, 1999 now U.S. Pat. No. 6,363,800, and is further a continuation-in-part of a utility application Ser. No. 09/494,962, filed on Jan. 31, 2000 now U.S. Pat. No. 6,290,065, which is a continuation-in-part of application Ser. No. 09/191,980 now U.S. Pat. No. 6,062,392, filed on Nov. 13, 1998 the benefits of the filing dates of which are hereby claimed under 35 U.S.C. §119(e) and 35 U.S.C. §120.

FIELD OF INVENTION

The invention relates to methods and devices for continuous monitoring of airborne particles, airborne biological particles, and systems of monitoring air quality.

BACKGROUND OF INVENTION

The separation and collection of particulates/aerosols from an airstream (or other fluid streams) is of concern in several contexts. In some cases, the goal may be to simply remove the particulates/aerosols from the fluid stream, thereby cleaning or purifying the fluid. Often it is desired to remove all particulates, regardless of composition, if the particulates are above a certain size. For example, automobile painting and the fabrication of silicon chips in clean rooms represent two situations in which all particulates large enough to result in an inferior product are desirably removed from the processing environment.

In other cases, particulates are collected for analysis to determine the type and concentration of such particulates/aerosols entrained in the fluid. For example, this technology may be employed in the detection of airborne biological or chemical warfare agents, the detection of biological contamination in confined spaces, such as aircraft or hospitals, or the detection of industrial pollutants (either in ambient fluid or in the effluent of smokestacks).

Much effort has been expended in the past in the detection and classification of particulates or aerosols in fluid streams. Impactors have been used for collecting aerosol particulates for many decades. In the earliest embodiments, a stream of fluid containing the particulates was accelerated toward an impactor plate. Due to their inertia, the particulates striking the impactor plate were collected on its surface, while the fluid was deflected to the side. With these types of impactors, only larger particulates could be collected, since particulates below a certain "cut size" were carried away by the fluid stream.

However, a significant disadvantage of such an impactor is the deposition of particulates on surfaces of the impactor other than the intended collection surfaces. This phenomenon reduces the accuracy of measurement of total particulate mass concentration and of the size-fractionation of particulates, since such losses cannot be accurately estimated for aerosols or particulates of varying size, shape, or chemistry.

Additionally, particulates may either become re-entrained in the fluid stream, or may bounce off the impactor's collection surface upon impact. To remedy this problem, "virtual" impactors have been developed that separate particulates from a fluid stream with techniques other than direct impaction. Virtual impactors may operate on a number of different principles, but all avoid actual "impact" as a means to separate particulates from a fluid in which the particulates are entrained and rely on differences in particulate mass to induce inertial separation. Specifically, a particulate-laden fluid stream is directed toward a surface presenting an obstruction to the forward movement of the fluid stream. The surface includes a void at the point where the particulates would normally impact the surface. When a major portion of the fluid stream changes direction to avoid the obstruction presented by the surface, fine particulates remain entrained in the deflected major portion of the fluid stream. Heavier or denser particulates, on the other hand, fail to change direction and are collected in a region of relatively stagnant fluid (a "dead zone") that is created near the surface. The heavier particulates entrained in a minor portion of the fluid stream enter the void defined through the surface, where they can be captured or analyzed.

Some examples of virtual impactors can be found in U.S. Pat. Nos. 3,901,798; 4,670,135; 4,767,524; 5,425,802; and 5,533,406. Because typical virtual impactors do not actually collect particulates themselves, but merely redirect them into two different fluid streams according to their mass, they are essentially free of the problems of particulate bounce and particulate re-entrainment associated with actual impactor devices. Still, particulate "wall loss," i.e., unintended deposition of particulates on various surfaces of virtual impactor structures, especially at curved or bent portions, remains a challenge with some designs of virtual impactors, because typically, many stages or layers of virtual impactors are required to complete particulate separation.

An additional aspect of the collection of fluid-entrained particulates, especially with respect to particulates that will be analyzed to determine a type and concentration of particulates, relates to when the collected particulates are to be analyzed. A common practice is to sample a fluid for a period of time, and then analyze the collected sample immediately, or at least as soon as practical. Depending on the nature of the particulates for which the fluid is being sampled, immediate analysis may be required. For example, if chemical or biological agents that pose an immediate health threat are suspected, real time analysis is preferred to enable protective measures to be taken immediately, before irreversible harm can occur. However, there are also many applications, such as routine monitoring of smokestacks and wastewater discharge, in which only a portion of the collected sample might need to be analyzed shortly after collection, while other portions are best archived for later analysis.

Archival samples can be prepared by taking a collected sample and manually splitting that sample into various fractions, including a first fraction to be analyzed relatively soon, and one or more additional portions to be archived for possible later analysis. While archival samples prepared by such a method are useful, the manual nature of such a method is time consuming and costly. Furthermore, during each step in which a sample is handled or manipulated (collection, separation, storage, and analysis), there is a significant chance that the sample will be inadvertently contaminated. It would thus be desirable to provide a method and apparatus that more readily enables archival samples to be prepared, with a minimal risk of contamination.

It should also be noted that the manner in which samples are collected affects the usefulness of the samples for archival purposes. Archival samples are often employed to determine more information about an event occurring at a specific time. For example, archival data collected from a smokestack might be used to determine at what time higher emissions occurred. That time could then be applied to analyze the process and equipment utilizing the smokestack to isolate the factors causing the excess emissions, so that the problem can be corrected. If the archival sample is merely a single sample collected over a 24-hour period, rather than 24 samples collected each hour for 24 hours, then little information can be obtained about when the excess emissions actually occurred, making it more difficult to determine the cause of the excess emissions. It would be therefore be desirable to provide a method and apparatus capable of providing archival samples for successive relatively short sampling periods, and which include time indexing enabling a specific archival sample to be correlated with a specific time at which the sample was taken.

Accordingly, a need exists to develop a method and apparatus capable of providing time-indexed archival samples with minimal operator effort, and minimal chance of contamination. Such archival samples desirably should include a high concentration of particulates, so that the archival samples are compact and require minimal storage space. Preferably, a virtual impactor that efficiently separates particulates from a fluid stream might be employed to collect the particulates.

Yet another aspect of the collection of fluid-entrained particulates, especially with respect to particulates collected with an impact collector, relates to how the collected particulates are to be analyzed. Most analytical techniques require a liquid sample. Regardless of how effective impact collectors are at removing particulates from a fluid stream (such as air), the collected particulates generally cannot readily be analyzed while remaining deposited on the impact collection surface. It would be desirable to provide a method and apparatus for removing collected particulates from an impact collection surface, and to transfer such particulates to a container that can be utilized to prepare a liquid sample. It would be further be desirable to provide an integrated system capable of collecting particulates from a fluid stream using an impact collector, and then transferring the collected particulates from the impact collector to a container suitable for preparing a liquid sample.

It should be noted that when a liquid sample is prepared using collected particulates, the amount of liquid used to prepare the liquid sample plays a significant factor in determining the concentration of the liquid sample. Higher concentration samples are generally require less challenging analytical techniques to analyze and are thus preferred. Therefore, it would be desirable for the method and apparatus employed to transfer collected particulates from an impact collection surface to a suitable container utilizing little or no liquid to unduly dilute the sample.

The typical problem facing the aerosol field is that of collecting and characterizing airborne particles. Characterization of these airborne particles can be performed in situ (i.e., while the particles remain suspended in a gas), or in extractive techniques where particles are collected and then deposited onto a solid substrate or into a liquid for the purpose of subsequent physical or chemical analysis.

Identifying biological materials in situ has been attempted by detection of autofluorescence of airborne bacteria. While autofluorescent properties may be useful in detecting biological particles, their in situ measurement is challenging for a number of reasons. It is particularly difficult to measure fluorescent characteristics of minuscule particles in an airborne state. The particles are available for analysis quite briefly, thus making it difficult to determine several informative characteristics. In addition, the equipment required comprises expensive powerful lasers and sensitive fluorescence photodetectors or photon counters. The resulting devices are large and expensive, making this technology unlikely to be adopted for some applications, such as routine monitoring of civilian buildings.

In alternative approaches, extractive instruments such as jet impingers, jet impactors, cyclones, and filters deposit particles onto substrates, which may be liquids, surfaces such as greased slides or agar-coated plates, or filters. The content of extracted particles can then be analyzed by any desirable technique. While analysis of airborne particles may be performed more thoroughly with extractive rather than in situ techniques, extractive techniques require consumables such as deposit substrates and/or analysis reagents and/or human involvement in the analysis. Continuous use of consumables and/or labor can become problematical and prohibitively expensive. Therefore, monitoring systems based on extractive techniques are also of questionable value for routine, continuous use.

There is a current need for devices and methods to continuously detect airborne particles. Continuous monitoring of the largest possible number of populated premises seems the most desirable option in dealing with the unpredictability of airborne biohazards emergence. Widespread adoption of such devices would allow protection of a large number of potentially endangered persons. For widespread adoption, however, such devices should be fairly inexpensive and reliable. Operation of the device should be automatic, i.e. not requiring any user input. In addition, to be used routinely in a large number of buildings airborne biohazard detection devices should ideally be maintenance free and use no consumables.

SUMMARY OF INVENTION

The present invention is directed to a method and apparatus for concentrating, collecting, and depositing "spots" of particulates from a fluid onto a solid collection surface, and then transferring the collected particulates to a container than can be utilized to store a liquid sample. Such a liquid sample can be analyzed immediately, or at some future time. A plurality of such samples, each relating to a specific time period and/or location of collection, can be stored and later analyzed to quantitatively and/or qualitatively test for a specific particulate at a specific time. It is anticipated that such samples will be very useful in the study of potentially hazardous particulates, including but not limited to viruses, bacteria, bio-toxins, and pathogens. Those of ordinary skill in the art will readily recognize that such samples can be analyzed using a variety of known analytical techniques including, but not limited to, mass spectrophotometry.

In a simplest embodiment, the invention relates to method and means for removing concentrated spots of collected particulates from an impact collection surface, and transferring the removed particulates to a container suitable for a liquid sample. A jet of fluid can be utilized to remove and transfer the particulates to a container. When a liquid jet is employed, care should be taken to ensure that a minimal amount of liquid is utilized, to avoid unnecessarily diluting the resulting liquid sample. The fluid employed should be selected to be inert with respect to the collected particulates.

A mechanical scraper can alternatively be employed to remove and transfer the particulates to a suitable container. A small volume of liquid can be employed to rinse the scraper, again with the understanding that too much liquid would undesirably dilute the sample. It is contemplated that such a mechanical scraper can be vibrated to facilitate the removal of particulates from the scraper. Once transferred to a suitable container, the particulates can be stored dry (if no liquid has been employed in the removal and transfer processes), or a suitable (preferably small) volume of liquid can be used to prepare a liquid sample.

In some other embodiments, a portion of the collection surface containing a specific spot of particulates is removed and placed into a container. Again, once containerized, such a sample can be stored dry, or liquid can be added to the container to prepare a liquid sample.

Preferable containers are plastic, although glass, metal, and ceramic can also be employed. As with any sample container, exemplary containers will be inert and clean, so that no contaminants are introduced into the sample.

Other embodiments of the present invention relate to integrated systems, which include the impact collection surface as well. It is anticipated that the present invention will perform particularly effectively if fluid-entrained particulates (most often airborne particulates) are efficiently collected and concentrated, a task for which a virtual impactor, such as described in a commonly owned copending U.S. patent application Ser. No. 10/066,404 (issued on May 3, 2005 as U.S. Pat. No. 6,887,710) entitled "ROBUST SYSTEM FOR SCREENING MAIL FOR BIOLOGICAL AGENTS." It is also particularly useful to providing means for moving the collection surface relative to the concentrated stream of particulates over time, so that spots located on different portions of the surface correspond to specific different increments of time. Preferably, the individual spots are disposed sufficiently far apart such that each individual spot can be removed and transferred to a suitable container without disturbing other spots.

The surface onto which the concentrated particulates are collected can be selected or modified to enhance the deposition of the particulates onto the surface, as well as to facilitate the removal and transfer of these particulates to a container suitable for preparing a liquid sample. In one embodiment, the impact collection surface is coated with a dissolvable coating, which is then rinsed with an appropriate solvent to remove the dissolvable coating and the collected particulates. In another embodiment, substantially the entire impact collection surface is soluble, and the portion of the impact collection surface with the desired spot of particles is removed and placed in the container. When the appropriate liquid (solvent) is added to the container, the collection surface dissolves and releases the particulates.

In another embodiment, the material of the collection surface is selected because of its porous nature. The pore sizes are sufficiently large to allow the fluid in which the particulates are entrained to freely pass through the archival surface, yet sufficiently small to prevent the particulates themselves from passing through the archival surface. Thus, the particulates are "filtered" from the fluid stream by the collection surface. To enhance removal of the particles, a fluid back flush can be employed. If the container is under a partial vacuum, the back flushed particles will be drawn into the container. Note that if the fluid is a gas, the concern regarding the use of so much liquid so as to undesirably dilute the sample of particles is obviated. In one embodiment, a vacuum is placed in fluid communication with an opposing side of a porous collection surface, causing the particles to adhere to the collection surface. When the vacuum source is no longer in fluid communication with the collection surface, the particles are readily removed.

In another embodiment, the collection surface is coated with a material selected to enhance a deposition of the particulates onto the collection surface while the material is in a first state, and to release the particulates when the material is in a second state. Such materials generally promote adhesion via chemical attraction, (i.e., a hydrophobic-hydrophobic attraction, or a hydrophilic-hydrophilic attraction). Electrical attraction can also be employed (i.e., a positively charged surface for collecting negative particles, or vice versa).

In at least one embodiment, the virtual impactor includes a separation plate employed for separating a fluid stream into a major flow and a minor flow. The major flow includes a minor portion of particles that are above a predetermined size, and the minor flow includes a major portion of the particles that are above the predetermined size. The separation plate includes a block in which is defined a laterally extending passage having an inlet disposed on one edge of the block and an outlet disposed on an opposite edge of the block. This laterally extending passage has a lateral dimension that is substantially greater than a transverse dimension of the passage. Opposed surfaces of the passage between which the transverse dimension of the passage is defined generally converge toward each other within the block, so that the outlet has a substantially smaller cross-sectional area than the inlet. A transverse, laterally extending slot is defined within the block and is in fluid communication with a portion of the passage that has the substantially smaller cross-sectional area. A major flow outlet port is also defined in the block, in fluid communication with the transverse, laterally extending slot. The major flow enters the slot and exits the block through the major flow outlet port, while the minor flow exits the block through the outlet of the passage. The major flow carries the minor portion of the particles and the minor flow carries the major portion of the particles.

In one aspect the present invention relates to methods for continuously monitoring airborne particles. Continuous monitoring according to the invented methods is achieved through a plurality of cycles. The methods are suitable for monitoring a variety of airborne particles. In specific embodiments they are designed to monitor the presence or concentration of airborne hazards. Cycles according to the invented methods comprise a plurality of steps.

A step according to the present methods is depositing airborne particles on a collection surface. Accordingly, a spot is formed on the collection surface. Depositing airborne particles is preferably accomplished by impaction caused by directing an air stream at the collection surface. In a preferred embodiment, airborne particles in the 0.5-10 μm size range are retained in the spot, the airborne particles retained in the spot thus comprising biological particles. Some embodiments comprise the optional step of pre-concentrating airborne particles of a desirable size range, such as particles with sizes between about 0.5-10 μm, in the air stream prior to impaction on the collection surface. Some embodiments comprise the optional step of preconditioning the air stream by removing particles of an undesirably large size. For example, particles of sizes greater than 10 μm may be removed. In some embodiments, both preconditioning and pre-concentrating are performed, with the pre-conditioning preferably prior to the pre-concentrating step.

In some embodiments, a step prior to depositing airborne particles is moistening the collection surface. Many types of liquids may be used to moisten the collection surface including glycerol, alcohols, or medium weight hydrocarbons, such as octane. The precise volume of liquid used in each cycle depends on several different variables, but may be about 5 μl.

Another step of the invented methods comprises analyzing the spot. The type of analysis performed depends on the nature of the particles to be monitored. Preferably, analyzing is accomplished by measuring biological, chemical, and/or radiological properties of the spot. In some embodiments, a plurality of properties is measured for each collected spot. Appropriate measurements in various embodiments may be directed to fluorescence, infrared absorption, mass specter, Raman specter, gamma emission, alpha emission, or beta emission properties of the spot. In preferred embodiments, biological particles are monitored by measuring autofluorescence of the spot. In some embodiments, analyzing is preceded by an optional step of pre-treating the spot so as to enhance the measured signal. Thus, pre-treating may comprise adding to the spot a liquid comprising an analysis-enhancing compound, or plasma lysing. In some embodiments where analyzing is accomplished by Matrix Assisted Laser Desorption Ionization (MALDI) time-of-flight mass spectrometry, pre-treating may be performed by plasma lysing and adding matrix solution to the spot.

Another step of the invented methods comprises regenerating the collection surface. As a result of this step the spot is removed and the collection surface is made available for another cycle. Regeneration is achieved by any one or combination of steps. For example, in some embodiments, regeneration is accomplished by pressing a felt pad against the collection surface and moving the felt pad over the collection surface. In other embodiments a felt wheel is rotated while pressed against the collection surface. In other embodiments the collection surface is electrostatically charged as part of the regeneration step. In other embodiments regeneration is accomplished by brushing the collection surface with a brush. In other embodiments regeneration is accomplished by blowing an air jet at high velocity towards the collection surface. In other embodiments, regeneration is accomplished by scraping the collection surface with a blade. In other embodiments, regeneration is achieved with heat, electricity, lasers or other forms of energy directed at the regenerative surface.

In some embodiments all the cycles of the invented methods are identical, whereas in other embodiments cycles may comprise different steps. In some embodiments, the invented methods in at least a subset of cycles comprise verifying the regeneration of the surface. Accordingly, the collection surface is analyzed after regeneration (the regenerated collection surface) essentially by the same process of analyzing the spot. Thus a background signal level is obtained for the regenerated surface. For example, if analyzing the spot is by measuring its fluorescence properties, verifying may be by similarly measuring the fluorescence properties of the regenerated collection surface to obtain a background fluorescence level. The background signal level is then compared to predetermined criteria. If the background level is found to be higher than desirable, regeneration and verification is repeated until the background signal level meets predetermined criteria. Alternatively, verifying may employ a test different from that used in the analysis step.

In other aspects, the present invention relates to devices useful for continuously monitoring airborne particles. In different embodiments the devices serve to monitor of the presence and concentration of airborne hazards for example of a biological, chemical, or radiological nature. The devices comprise several components, which are present in different combinations in different embodiments.

One component of the invented devices is an impaction plate. One of its features is a collection surface, on which a spot of airborne particles gets collected when the devices are in operation. In some embodiments, the collection surface is smooth, and is therefore easily cleaned by a surface regenerator. In other embodiments, the collection surface comprises features that improve the collection efficiency of impacting airborne particles, such as pyramid-shaped structures of about 1-10 μm in height and width. In some embodiments, the impaction plate comprises more than one, i.e. a plurality of collection surfaces.

Another component of the invented devices is a spotting nozzle. The spotting nozzle directs an air stream towards the collection surface of the impaction plate. The resulting impact of the air stream produces a spot that contains airborne particles on the collection surface. In some embodiments a particle concentrator, such as a virtual impactor, is placed upstream of the spotting nozzle, which increases the concentration of airborne particles within a desirable size range. In some embodiments, a size selective inlet is placed upstream of the spotting nozzle, which eliminates airborne particles greater than a desirable size. In some embodiments, both a concentrator and a size selective inlet are present upstream of the spotting nozzle. In some embodiments the spotting nozzle is substantially vertical while the collection surface is substantially horizontal. In preferred embodiments the nozzle, impaction surface and air stream velocity are configured so that the spot is enriched in particles of about 0.5-10 μm sizes.

Another component of the invented devices is an analyzer, which can examine characteristics of the spot on the collection surface. In preferred embodiments the analyzer is a fluorescence detector that determines the intrinsic fluorescence characteristics of the spot. In other embodiments, the analyzer may be for example, an infrared absorbance detector, a mass spectrometer, a Raman spectrometer. Some embodiments comprise more than one analyzer. Thus, any means for analyzing the spot suitable for detecting a class of airborne particles may be employed.

In some embodiments, the invented devices comprise a pre-analysis spot preparation station. At this point the spot is prepared to enhance its characteristics measured by the analyzer. For example, the spot may be combined with compounds that affect measured properties of the airborne particles of interest by squirting a liquid containing the appropriate compound from an inkjet type of device. In one embodiment, the pre-analysis spot preparation station applies a plasma lysis pulse to the spot, which is then analyzed by MALDI mass spectrometry.

Another component of the present devices is a surface regenerator. This component removes the spot from the collection surface during operation of the devices, thus regenerating the surface. In some embodiments the regenerator is a felt pad that regenerates the collection surface by pressing against the collection surface while the pad and the collection surface move relative to each other. In some embodiments, the surface regenerator is a felt wheel that is pressed against the collection surface and simultaneously rotated by a coupled motor. In some embodiments the regenerator is a blade that regenerates the collection surface by scraping or wiping it. In some embodiments the surface regenerator is a brush that regenerates the surface by brushing or sweeping it. In some embodiments the surface regenerator is a regenerator nozzle that blows air at high velocity towards the collection surface, preferably at an angle. In some embodiments, the regenerator comprises means for electrostatically charging the collection surface, which loosens an attached spot. The regenerator may comprise any means for directing energy to the spot and/or collection surface. Useful energy forms include heat, electricity, or lasers. Some embodiments comprise more than one surface regenerator, which may be of similar or different types. Thus, any means for regenerating the collection surface may be employed.

Another component present in some embodiments is a liquid coating applicator. It moistens the collection surface prior to impaction of the airstream, and thus helps trapping airborne particles and enhances the collection efficiency. The liquid coating applicator may be, for example, a felt tip pen. It might alternatively be similar to inkjet printing devices. It comprises a reservoir of liquid to be applied to the collection surface. There are several types of liquids that may be used, including alcohol, glycerol, or a medium weight hydrocarbon such as octane.

Another component of the devices is a homing sensor. Its function is to operatively position the collection surface to the various device components present in different embodiments, including the liquid coating applicator if present, the spotting nozzle, the pre-analysis spot preparation station if present, the analyzer, and the surface regenerator. Thus, in operation the homing sensor can cyclically position the collection surface sequentially from the liquid coating applicator if present to the spotting nozzle to the analyzer, to the pre-analysis spot preparation station, and to the surface regenerator. In general, the invented devices may accomplish the function of positioning the collection surface to each present component by any means for translocating the collection surface relative to the other device components. For example, a prime mover may be coupled to a shaft to which the impaction plate is attached, and proper positioning of the collection surface is accomplished by rotation of the shaft at predefined angles.

The different components of the invented devices can take various shapes in specific embodiments. For example, the homing sensor may comprise a shaft attached to the impaction plate. A prime mover is coupled to the shaft, and the homing sensor functions by rotating the disk at predefined angles. Each rotation step operatively positions the collection surface to a component of the devices. In some embodiments, the impaction plate is a disk, and a shaft is positioned along the disk axis and bound to the disk. In another preferred embodiment, the impaction plate is a lobed cam, and the impaction surfaces on the side of the cam. The impaction surfaces are flat, and may be produced directly on the cam or created by flat inserts embedded in the cam. The preferred material for the insert is a material of high surface hardness, such as hard-anodized steel, quartz or sapphire.

In another aspect, the present invention relates to devices useful for detecting or measuring airborne biological particles. The devices may comprise a collection surface, typically a regenerative collection surface, which supports a spot of immobilized airborne particles. In many embodiments, the devices further comprise an inertial impactor that immobilizes the spot on the collection surface.

The invented devices comprise a detector that is capable of analyzing the content of the spot. Typically, the detector is capable of sensing a biological signature that is present in the spot. The biological signature is preferably autofluorescence of biomolecules, but any other known signature may be sensed, including various types of Raman, infrared absorption, or mass spectra. These biological signatures are detected with known devices such as fluorescence detectors, Raman spectrometers, Fourier transform infrared spectrometers, or MALDI mass spectrometers. In some embodiments, multiple detectors analyze the spot. As a result of analysis, the detector produces signals, typically electrical signals, which are indicative of the biological signature. Consequently, the detector may recognize the presence of specific biological materials or may measure the concentration of classes of biological materials.

Preferably, the detector is a fluorescence detector that measures the inherent fluorescence of biological particles. The fluorescence detector comprises an excitation light source, which emits an excitatory radiation towards the spot to be analyzed. Any available source of radiation may be used. In some embodiments, the excitation light source is a LED. The excitatory radiation is of wavelengths operative to excite biomolecules to produce fluorescence. In many embodiments, the excitatory radiation is substantially ultraviolet, and the fluorescence radiation may be substantially visible. For example, the excitatory wavelength may be within the 340-370 nm range, or it may be approximately 266 nm, or it may be approximately 400 nm.

Fluorescence detectors also comprise fluorescence photosensors, which measure the radiation emitted from the spot in response to excitation. Any available photosensor may be used. In some embodiments, the fluorescence photosensor is a photodiode. Fluorescence detectors may also comprise additional components, such as a dichroic mirror that substantially reflects excitatory radiation and is substantially transparent to fluorescence radiation. The dichroic mirror can be positioned to reflect the excitatory radiation towards the spot, and allow passage of the emission radiation to the photosensor. Other optical components may also be employed, such as an excitation filter positioned between the excitation light source and the dichroic mirror or spot, and an emission filter positioned between the dichroic mirror or spot and the fluorescence photosensor.

As mentioned above, the detector produces signals related to the biological signature detected. The signals are usually transmitted to a receiver, which may then relay the signals for further processing. The signals typically reach a processor, which may be a computer or a Neuron Chip®. The processor is capable to process or interpret the signals and thus establish or gauge the concentration of biological particles in the spot. Consequently, the processor is capable to establish when the concentration of biological particles in the spot exceeds a predetermined value. In such a case, the processor outputs an alarm signal that alerts users of the presence of potentially harmful levels of airborne biological particles.

In yet another aspect, the present invention is related to methods of detecting specific airborne particles or concentrations of airborne biologicals. The methods comprise a plurality of steps, which may be repeated cyclically to ensure continuous monitoring of environmental air. One step according to the invented methods is depositing airborne particles on a regenerative collection surface to form a spot, which may be accomplished by inertial impaction. Another step comprises measuring a biological signature present in the spot. Examples of biological signatures are provided above. Consequently the presence of concentration of airborne biological particles is determined from the measurement. Where the steps are preformed cyclically, each measurement generates a present value of the concentration of airborne biological particles. Values from preceding measurements may be at least temporarily stored and used in calculating the average value and the standard deviation from prior measurements. Thus, a defined number of prior values can be used calculating the average, for example eight, which are derived from measurements in the preceding cycles. The present value is then compared to the calculated average to determine if the present value exceeds the average to a significant extent. The standard deviation from the prior measurements can be used to establish if the present value is abnormally high. Thus, the present value may be compared to the average value plus a preset factor, for example between 3 and 8, multiplied by the standard deviation. If the present value does exceed the average value to a significant extent, then the processor outputs an alarm signal. Finally, another step is regenerating the collection surface.

In other aspects, the present invention comprises devices, systems such as for monitoring and controlling air quality, and networks such as control networks. Different facets of the invention relate to applications that improve, for example, buildings or public facilities, HVAC systems, airplanes, and generally result in overall safer premises. Sensors based on regenerative surface air samplers can be employed in monitoring airborne hazards. For example, biological, chemical, or radiological sensors can be set to continuously observe air quality. Sensors based on regenerative surface air samplers may be deployed as stand alone devices, but they may also be incorporated into smart or intelligent sensor networks.

The sensors communicate signals through a communication interface, which may be a transmitter in some embodiments. In other embodiments the communication interface is a transceiver. Signals are typically communicated over a control network such as a building automation system network. The communication interface or transceiver can communicate through a wired or wireless connection. In some embodiments, the transceiver communicates via an RF link to an RF link network.

In some embodiments, the sensor based on a regenerative sample may output a positive response that directly activates other devices, for example specific sensors capable of identification of specific chemical, biological, or radiological species or narrow classes of species, samplers capable of capturing and/or archiving samples of airborne particles, or other sensors that are not based on regenerative surfaces.

As mentioned above, the sensors preferably communicate to an automation system network, such as a LonWorks® automation system or a CEBus automation system. Preferably, a transceiver communicates through a standard protocol, such as the BACnet protocol or the LonTalk® protocol.

In many embodiments, a controller is communicatively coupled to the sensor. In some embodiments the controller is a Neuron® chip. Typically, the controller is also coupled to the transceiver. In some embodiments the controller is coupled to at least one actuator and capable of actuating at least one air management component in response to information received from the sensor. The controller may also be communicatively coupled to the air management component, and thus it may be able to receive and integrate information additional to that received from the sensor. Examples of air management components are air analysis devices such as sample capture devices, sample analysis devices, or particle counters, smoke or fire sensors, or air control devices such as air duct dampers.

In another aspect, the present invention relates to methods of constructing a sensors network. Accordingly, sensors based on a regenerative surface air sampler can be added into a network. The sensors may be of biological particles, or chemical or radiological sensors. The network may contain any number of additional components, such as smoke or fire sensors.

In yet another aspect the present invention relates to methods of controlling ambient air quality. According to the invented methods, ambient air is sampled with at least one sensor based on a regenerative surface air sampler. Sampling can take place continuously and automatically. If at one point sampling by the sensor indicates a probable threat, a responsive step is performed. The responsive step may comprise actuating at least one air management component, activating at least one specific sensor, issuing an alert signal. In case an alert signal is issued, it may be transmitted to one or several locations, such as facility management or a fire department or law enforcement agency creating a two-tier warning system.

BRIEF DESCRIPTION OF DRAWINGS

FIG. 5A is an isometric view of yet another alternative embodiment of a separation plate in accord with the present invention;

FIG. 5B is a cross-sectional view of the separation plate of FIG. 5A, showing additional separation plates arrayed on each side in phantom view;

FIG. 6A is an isometric view of still another alternative embodiment of a separation plate in accord with the present invention;

FIG. 6B is a cross-sectional view of the separation plate of FIG. 6A, showing additional separation plates arrayed on each side in phantom view;

FIG. 10 (prior art) is a schematic view of a fluid in which particulates are entrained, showing the particulates impacting an uncoated impact collection surface;

FIG. 11 is a schematic view of a fluid in which particulates are entrained, showing the particulates impacting a coated impact collection surface in accord with the present invention;

FIG. 12 is a schematic view of a flexible tape having a partially coated impact collection surface;

FIG. 13 is a schematic view of a flexible tape having a continuously coated impact collection surface;

FIG. 27 is a diagram of a method for continuous monitoring of airborne biological particles;

DETAILED DESCRIPTION OF PREFERRED EMBODIMENTS

Figure 1A:
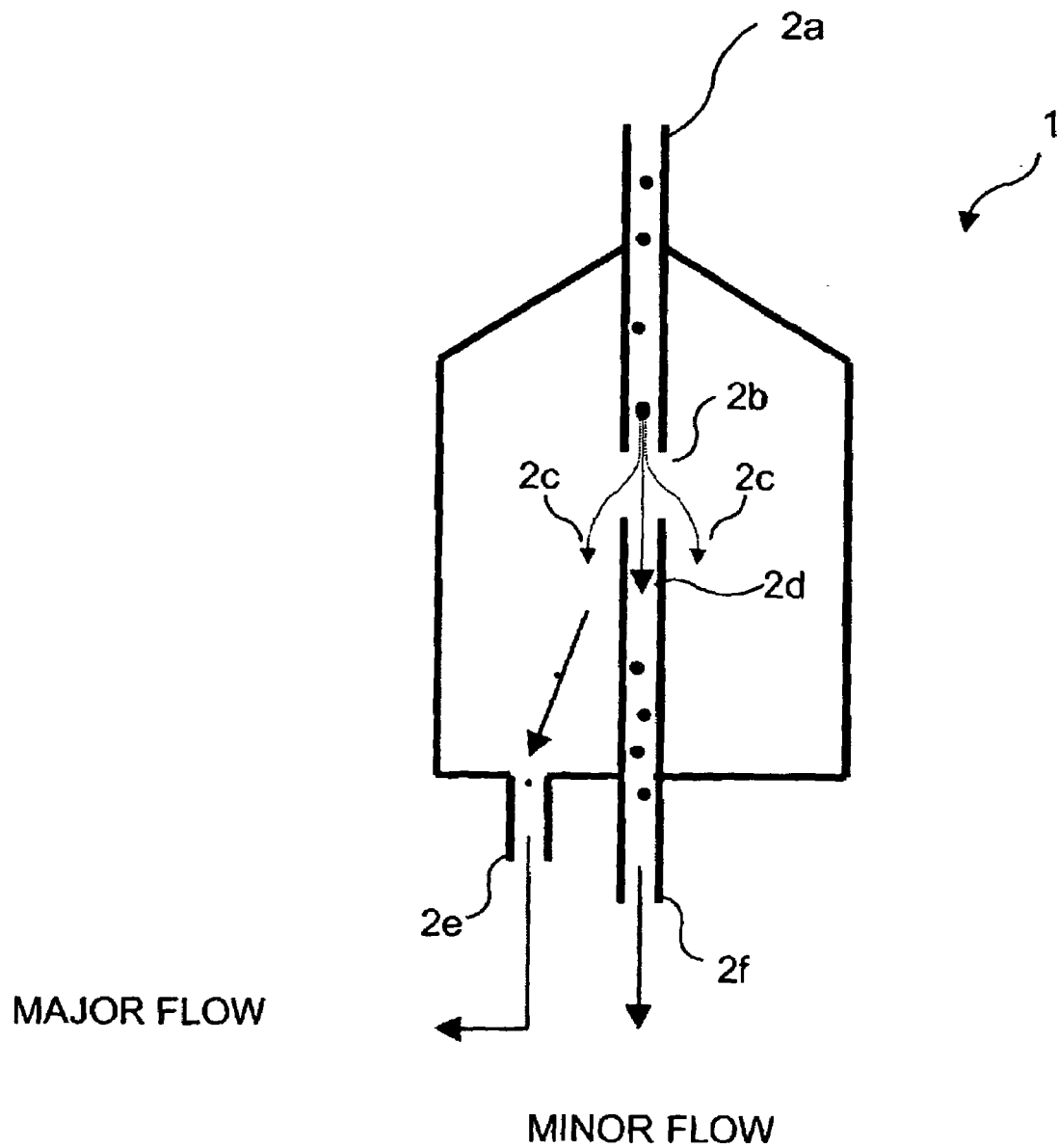
FIG. 1A is a schematic view of a virtual impactor.

The present invention is directed to a method and apparatus for removing concentrated samples or spots of collected particulates from an impact collection surface, and transferring the removed particulates to a container suitable for preparing a liquid sample. The sample can then be analyzed by any of a number of suitable techniques to identify the particulates that were collected. For example, such samples can be analyzed using mass spectrophotometry.

In a first embodiment, means are provided for removing and transferring the particulates from a collection surface into a sample container. This embodiment can be used with a variety of different impact collectors that collect the particulates on the collection surface.

Another embodiment includes elements for concentrating, collecting, and depositing "spots" of particulates from a fluid onto a collection surface, as well as the means for removing and transferring the particulates into a sample container.

Such an integrated system can be employed to collect particulates, and facilitate preparation of a liquid sample. As noted above, many different analytical techniques require a liquid sample. While an impact collection surface might be removed from a separate system adapted to collect particulates and introduced into a separate system that is designed to prepare such a liquid sample, an integrated system that facilitates collection of the particulates and preparation of the liquid sample without removing the collection surface is preferable.

In one embodiment of an integrated system, the collection surface is an archival quality medium, preferably capable of retaining collected particulates in a stable environment for a relatively long period of time. Such a surface will function as an archive on which are deposited many spots collected at known temporally spaced-apart times from a known site. The archive will likely be useful if it is necessary to investigate environmental conditions at a particular site at a future time. Archived particulates can include, but are not limited to, viruses, bacteria, bio-toxins, and pathogens. When one or more spots from such an archive require analysis, the integrated system facilitates removal and transfer of the particulates to a sample container to provide a sample for analysis.

Preferably, such an integrated system employs a virtual impactor to efficiently collect and concentrate airborne particulates. The minor flow from the virtual impactor is directed toward a suitable archival quality surface to deposit concentrated spots of particulates. The archival surface is moved relative to the concentrated stream of particulates from the virtual impactor over time, so that spots or samples of the particulates that have been collected on different portions of the archival surface correspond to different times at which the particulates were collected. Preferably, the invention includes means for associating a date and time with each spot for the purpose of accurately archiving the sample collected, so that a specific spot can be located and retrieved.

A preferred integrated system also includes a control unit, such as a computing device or hard-wired logic device that executes sample protocols to determine when the fluid is sampled to produce each of the spots. Sample protocols can be applied to determine when a particular spot should be transferred from the collection surface to a sample container.

Those of ordinary skill in the art will recognize that other embodiments of an integrated system are possible within the scope of the present invention. For example, while it is deemed preferable to use a virtual impactor in such an integrated system, other types of particulate collectors can alternatively be employed.

In the following description, the prefix "micro" is applied generally to components that have sub-millimeter-sized features. Micro-components are fabricated using micro-machining techniques known in the art, such as micro-milling, photolithography, deep ultraviolet (or x-ray) lithography, electro-deposition, electro-discharge machining (EDM), laser ablation, and reactive or non-reactive ion etching. It should be noted that micro-machined virtual impactors provide for increased collection efficiency and reduced pressure drops.

Also as used hereinafter, the following terms shall have the definitions set forth below:

Particulate—any separately identifiable solid, semi-solid, liquid, aerosol, or other component entrained in a fluid stream that has a greater mass than the fluid forming the fluid stream, and which is subject to separation from the fluid stream and collection for analysis. For the purposes of the present description, the mass density of particulates is assumed to be approximately 1 gm/cm.sup.3. It is contemplated that the particulates may arise from sampling almost any source, including but not limited to, air, water, soil, and surfaces, and may include inorganic or organic chemicals, or living materials, e.g., bacteria, cells, or spores.

Fluid—any fluid susceptible to fluid flow, which may comprise liquids or gases, and which may entrain foreign particulates in a flow thereof. Unless otherwise noted, fluid shall mean an ambient fluid containing unconcentrated particulates that are subject to collection, not the fluid into which the particulates are concentrated after collection or capture.

Spot—an aggregate of particulates deposited upon an archival surface in a relatively small area, so that the individually small particulates are aggregated together to form a larger spot, which can be more readily observed by magnification or by the naked eye.

The following description will first describe a preferred particulate collector and concentrator to be used in an integrated system. Then, archival surfaces for such an integrated system will be discussed, as well as suitable apparatus for moving the archival surface relative to the collector. Finally, suitable means for removing and transferring particulates from a collection surface to a container are discussed.

Particulate Concentrating

Because particulates of interest are often present in quite small concentrations in a volume of fluid, it is highly desirable to concentrate the mass of particulates into a smaller volume of fluid. Virtual impactors can achieve such a concentration without actually removing the particulates of interest from the flow of fluid. As a result, the particulate-laden fluid flow can be passed through a series of sequentially connected virtual impactors, so that a fluid flow exiting the final virtual impactor represents a concentration of particulates two to three orders of magnitude greater than in the original fluid flow. The concentrated particulates can then be more readily deposited on an archival surface.

A virtual impactor uses a particle's inertia to separate it from a fluid stream that is turned, and a basic virtual impactor can be fabricated from a pair of opposing nozzles. Within a virtual impactor, the intake fluid coming through the inlet flows out from a nozzle directly at a second opposed nozzle into which only a "minor flow" is allowed to enter. This concept is schematically illustrated by a virtual impactor 1 shown in FIG. 1A. Fluid carrying entrained particulates flows through a first nozzle 2a. The flow from nozzle 2a then passes through a void 2b that separates nozzle 2a from a nozzle 2f. It is in void 2b that the flow of fluid is divided into a major flow 2c, which contains most of the fluid (e.g., 90%) and particles smaller than a cut (predetermined) size, and a minor flow 2d. Minor flow 2d contains a small amount of fluid (e.g., 10%) in which particulates larger than the cut size are entrained. Thus the minor flow exits via nozzle 2f, and the major flow exits via an outlet 2e.

As a result of inertia, most of the particulates that are greater than the selected cut size are conveyed in this small minor flow and exit the virtual impactor. Most of the particulates smaller than the virtual impactor cut size are exhausted with the majority of the inlet air as the major flow. The stopping distance of a particle is an important parameter in impactor design. The cut point (the size at which about 50% of the particles impact a surface, i.e., flow into the second nozzle) is related to the stopping distance. A 3 micron particle has nine times the stopping distance of a 1 micron particle of similar density.

For the present invention, several types of virtual impactors and their variants are suitable for use in collecting samples as spots for archiving purposes. Because any particular design of the minor flow nozzle can be optimized for a particular size of particles, it is contemplated that at least some embodiments of the present invention may include multiple nozzles, each with a different geometry, so that multiple particle types can be efficiently collected.

In one preferred embodiment, two virtual impactors are aligned in series, such that a concentration of particulates entrained in the minor flow of fluid exiting the second virtual impactor is approximately 100 times the original concentration.

Figure 1B:
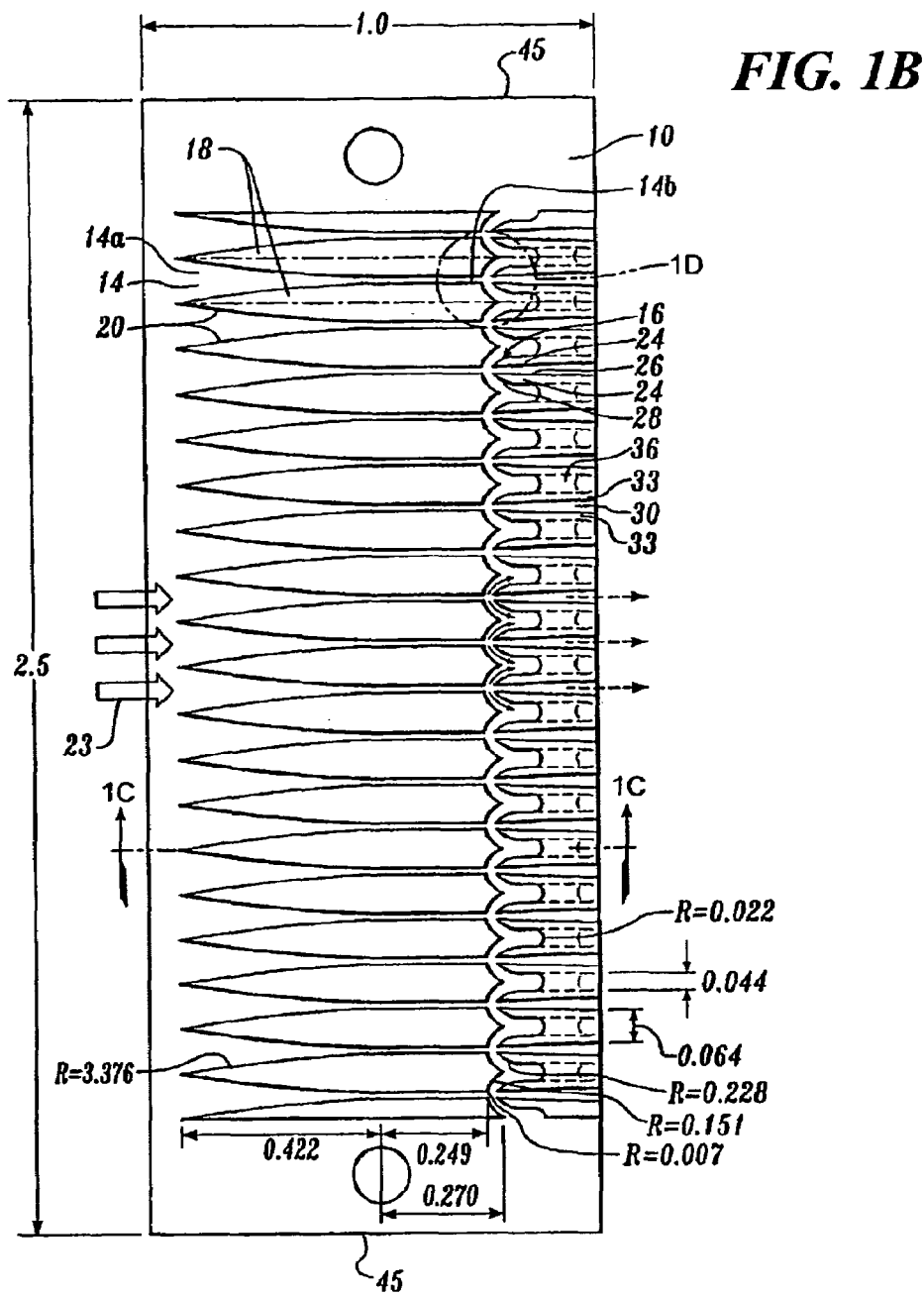
FIG. 1B is a plan view of a separation plate employed in the present invention.
Figure 1C:
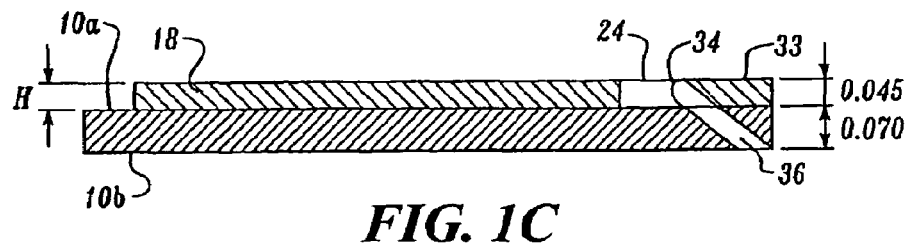
FIG. 1C is a cross-sectional view of the separation plate taken along line 1C-1C of FIG. 1B.
Figure 1D:
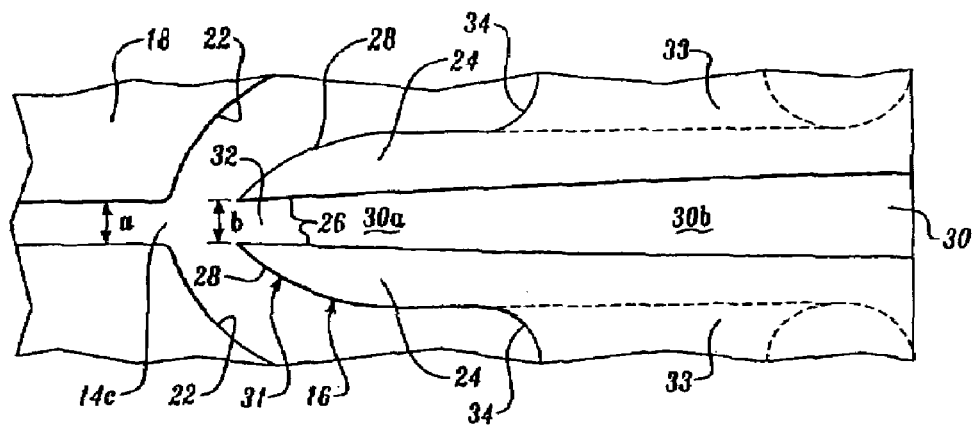
FIG. 1D is an enlarged view of a pair of a nozzle and a virtual impactor at section 1C of FIG. 1B.

FIGS. 1B, 1C, and 1D illustrate a first embodiment of a virtual impact separation plate 10 formed in accordance with the present invention. Separation plate 10 may be formed of various materials suitable for micro-machining, such as plastics and metals. The separation plate includes a first surface 10a and an opposing second surface 10b (FIG. 1C). The first surface 10a includes plural pairs of a nozzle 14 and a virtual impactor 16 (FIG. 1D). Each nozzle 14 includes an inlet end 14a and an outlet end 14b and is defined between adjacent nozzle projections 18 having a height "H" (see FIG. 1C). Two nozzle projections 18 cooperate to define one nozzle 14. Each nozzle projection 18 includes two side walls 20 that are configured to define one side of a nozzle 14, which comprise a telescoping design that generally tapers from inlet end 14a to outlet end 14b. Nozzle projection 18 further includes two generally concave walls 22 at its downstream end that are positioned to provide nozzle projection 18 with a tapered downstream "tail." In contrast to a tapered downstream tail, another of the embodiments described below that is actually more preferred includes stepped transitions that reduce the size of the passage at its outlet. Throughout the present description, the terms "upstream" and "downstream" are used to refer to the direction of a fluid stream 23 flowing through the separation plate of the present invention.

Each virtual impactor 16 comprises a pair of generally fin-shaped projections 24 having height "H." Each fin-shaped projection 24 includes an inner wall 26 and a generally convex outer wall 28. Inner walls 26 of fin-shaped projections 24 (for a pair) are spaced apart and face each other to define an upstream minor flow passage 30a there between. Convex outer walls 28 of the pair of fin-shaped projections 24 cooperatively present a generally convex surface 31 facing the fluid flow direction. Referring specifically to FIG. 1D, an inlet end 32 of upstream minor flow passage 30a defines a virtual impact void through convex surface 31, where "virtual" impaction occurs as more fully described below. A width of outlet end 14b of nozzle 14 is defined as "a," and a width of inlet end 32 of upstream minor flow passage 30a is defined as "b." First surface 10a of separation plate 10 may further include a plurality of virtual impactor bodies 33 extending downstream from the downstream ends of adjacent fin-shaped projections 24 of adjacent pairs of virtual impactors 16. Each virtual impactor body 33 includes opposing external walls that extend downstream from the downstream ends of inner walls 26. External walls of adjacent virtual impactor bodies 33 are spaced apart to define a downstream minor flow passage 30b there between. Upstream and downstream minor flow passages 30a and 30b are aligned and communicate with each other to form minor flow passage 30. As illustrated in FIGS. 1B, 1C, and 1D, fin-shaped projections 24 of adjacent virtual impactors 16 and virtual impactor body 33 may be integrally formed. Optionally, an orifice 34 may be defined through virtual impactor body 33 adjacent to the downstream ends of convex outer walls 28 of adjacent virtual impactors 16. Orifices 34 define terminal ends of passageways 36 that extend downwardly and downstream through separation plate 10 to second surfaces 10b. As more fully described below, orifices 34 and passageways 36 are provided merely as one example of a major flow outlet and, thus, may be replaced with any other suitable major flow outlet.

In operation, particulate-laden fluid stream 23 is caused to enter inlet ends 14a of nozzles 14. Nozzles 14 aerodynamically focus and accelerate particulates entrained in fluid stream 23. In this telescoping design, the aerodynamically focused fluid stream 23 exiting outlet ends 14b of nozzles 14 advances to convex surfaces 31 of virtual impactors 16. A major portion (at least 50%, and preferably, at least about 90%) of fluid stream 23 containing a minor portion (less than about 50%) of particulates above a certain particulate diameter size, or a cut size, hereinafter referred to as a "major flow," changes direction to avoid the obstruction presented by convex surfaces 31. Concave walls 22 of nozzle projections 18 and convex outer walls 28 of fin-shaped projections 24 cooperate to direct the major flow toward the upstream end of virtual impactor bodies 33. Bodies 33 prevent the major flow from continuing in its current direction. Orifices 34 are provided through bodies 33, so that the major flow enters orifices 34 and travels through passageways 36 to second surface 10b of separation plate 10, where it is exhausted or processed further. A minor portion (less than 50%, and preferably less than about 10%) of fluid stream 23 containing a major portion (at least about 50%) of particulates above the cut size, exits as the minor flow and is collected near a "dead" zone or a zone of nearly stagnant air created adjacent to the convex surfaces 31 of virtual impactors 16. The major portion of the particulates entrained in the minor flow "virtually" impacts the virtual impact voids at inlet ends 32 of upstream minor flow passages 30a and enters minor flow passages 30. The minor flow travels through and exits minor flow passages 30, enabling the particulates entrained therein to be collected for analysis and/or further processing.

Nozzles 14 contribute very little to particulate loss because they have a long telescoping profile, which prevents particulate deposition thereon. The long telescoping profile of the nozzles 14 also serves to align and accelerate particulates. Focusing the particulates before they enter the minor flow passage using the telescoping design may enhance the performance of the virtual impactor, since the particulates in the center of the nozzle are likely to remain entrained in the minor flow. Thus, as used herein, the term "aerodynamic focusing" refers to a geometry of a particulate separator that concentrates particulates toward the center of a central channel through the particulate separator. Because nozzles 14 aerodynamically focus and accelerate particulates in a fluid stream, virtual impactors 16 placed downstream of nozzles 14 are able to separate particulates very efficiently. By improving the particulate separation efficiency of each of virtual impactors 16, the present invention enables only one layer or row of virtual impactors 16 to carryout the particulate separation, which eliminates the chances of particulates being lost due to impact on surfaces of additional layers or rows of virtual impactors. The present invention further reduces particulate loss on inner surfaces of minor flow passages, by enabling minor flows to advance straight through the minor flow passages upon virtual impaction, without having to change their flow direction.

A separation plate 10 configured in accordance with the dimensions (all in inches) shown in FIGS. 1B and 1C is designed to have a cut size of about 1.0 microns at a flow rate of 35 liters per minute (lpm). It should be understood that those of ordinary skill in the art may readily optimize separation plate 10 of the present invention to meet a specific cut size requirement at a predefined flow rate. For example, the cut size of a separation plate may be modified by scaling up or down the various structures provided on the separation plate; larger nozzles with proportionally larger virtual impactors are useful in separating larger particulates, while conversely, smaller nozzles with proportionally smaller virtual impactors are useful in separating smaller particulates. The cut size of a separation plate may also be modified by adjusting a flow rate through the separation plate.

With reference to FIG. 1D, for particulates having 1 to 3 micron diameters, it has been found that making the dimension "a" greater than the dimension "b" generally reduces recirculation of a minor flow upon entering minor flow passage 30, which is preferable for efficiently separating a minor flow from a major flow. For larger particulates, it may be preferable to make "b" larger than "a" to reduce pressure drop.

Figure 1E:
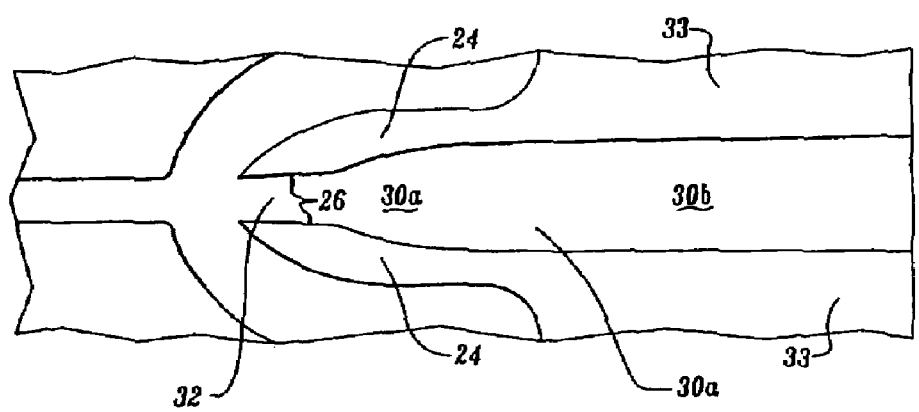
FIG. 1E is an enlarged view of another configuration of a pair of a nozzle and a virtual impactor.

FIG. 1E illustrates modified configurations of a nozzle 14 and a virtual impactor 16, wherein inner walls 26 of fin-shaped projections 24 include a generally concave surface. Accordingly, the width of upstream minor flow passage 30a expands from inlet end 32 toward downstream minor flow passage 30b, which is defined between the external walls of adjacent virtual impactor bodies 33. This configuration is advantageous in reducing particulate loss onto inner walls 26.

A separation plate of the present invention may be easily modified to process virtually any volume of fluid stream at any flow rate, by varying the number of nozzles 14 and virtual impactors 16 provided on the separation plate. Furthermore, the throughput of separation plate 10 may be almost indefinitely modifiable by increasing or decreasing height "H" of nozzles 14, virtual impactors 16, and virtual impactor bodies 33. It should be noted that height "H" of a separation plate of the invention could be freely increased without a significant increase in particulate loss. This capability is made possible by the design of this virtual impactor that allows minor flows to advance straight through without experiencing any deflected path.

Figure 2A:
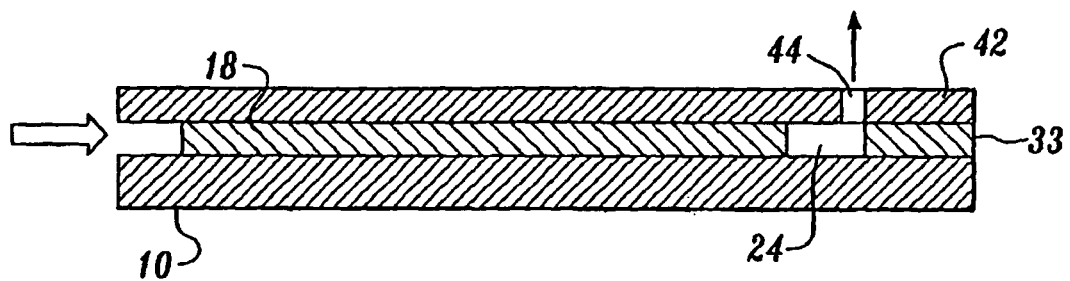
FIG. 2A is a schematic cross-sectional view of a virtual impact collector that includes another configuration of a separation plate in accord with the present invention.

Separation plate 10 of the present invention may be readily incorporated into various particulate separation/concentration apparatus. Referring to FIG. 2A, for example, a virtual impact collector may be formed by placing a cover plate 42 over projections 18, fin-shaped projections 24, and virtual impactor bodies 33 provided on first surface 10a. Cover plate 42 and first surface 10a cooperatively define a chamber. Inlet ends 14a of nozzles 14 provide an inlet through which a particulate-laden fluid stream may enter the chamber. Minor flow passages 30 provide an outlet through which a minor flow may exit the chamber; however, an outlet through which a major flow may exit the chamber may be provided in various other ways. For example, as in FIGS. 1B and 1C, the plurality of orifices 34 defining terminal ends of passageways 36 may be provided through virtual impactor bodies 33. Alternatively, as in FIG. 2A, cover plate 42 may include a plurality of orifices 44 that extend there through. Orifices 44 are configured and arranged so that when cover plate 42 is mated with separation plate 10, orifices 44 are disposed between virtual impactors 16 and adjacent to the upstream end of virtual impactor bodies 33, to exhaust major flows flowing around virtual impactors 16 that are blocked by bodies 33, as indicated by the arrow. It should be understood that, in operating the virtual impact collector as described above, those of ordinary skill in the art can provide a suitable flow subsystem for causing a fluid stream to flow through the chamber.

Figure 2B:
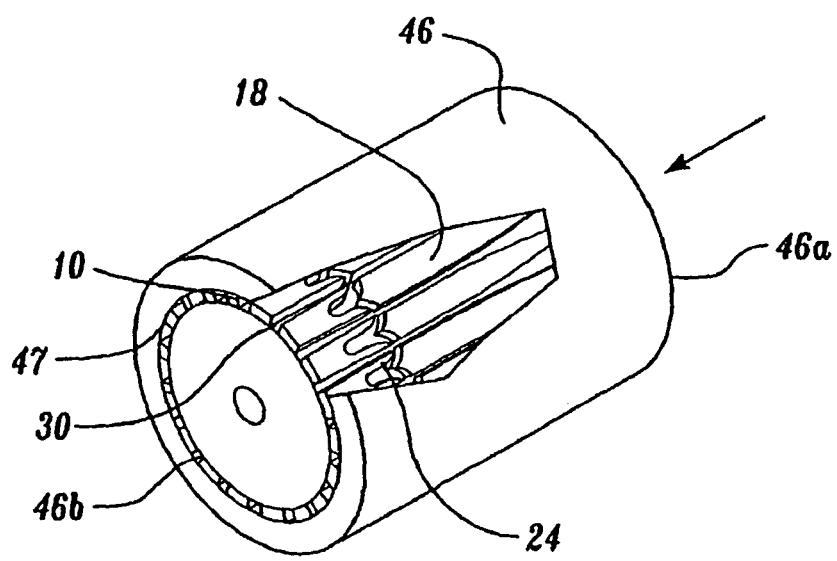
FIG. 2B is a schematic perspective view of an alternative configuration of a virtual impact collector in accord with the present invention.

A further example of a virtual impact collector formed in accordance with the present invention is schematically illustrated in FIG. 2B. In this embodiment, separation plate 10 of FIG. 1B is joined at its opposing edges 45 to form a cylinder. The second surface of separation plate 10 forms the inner surface of the cylinder. The cylindrical separation plate 10 is coaxially slid into a tube 46 having two open ends 46a and 46b to form an annular chamber 47 there between. As before, a suitable major flow outlet (not shown) is provided. In operation, particulate-laden fluid streams enter chamber 47 through the inlet ends of the nozzles defined between nozzle projections 18, adjacent to open end 46a. Minor flow passages 30 provide an outlet through which a minor flow exits chamber 47. A suitably provided major flow outlet deflects a major flow to either or both of the inner surfaces of the cylindrical separation plate 10 and/or the outer surface of tube 46.

Figure 3A:
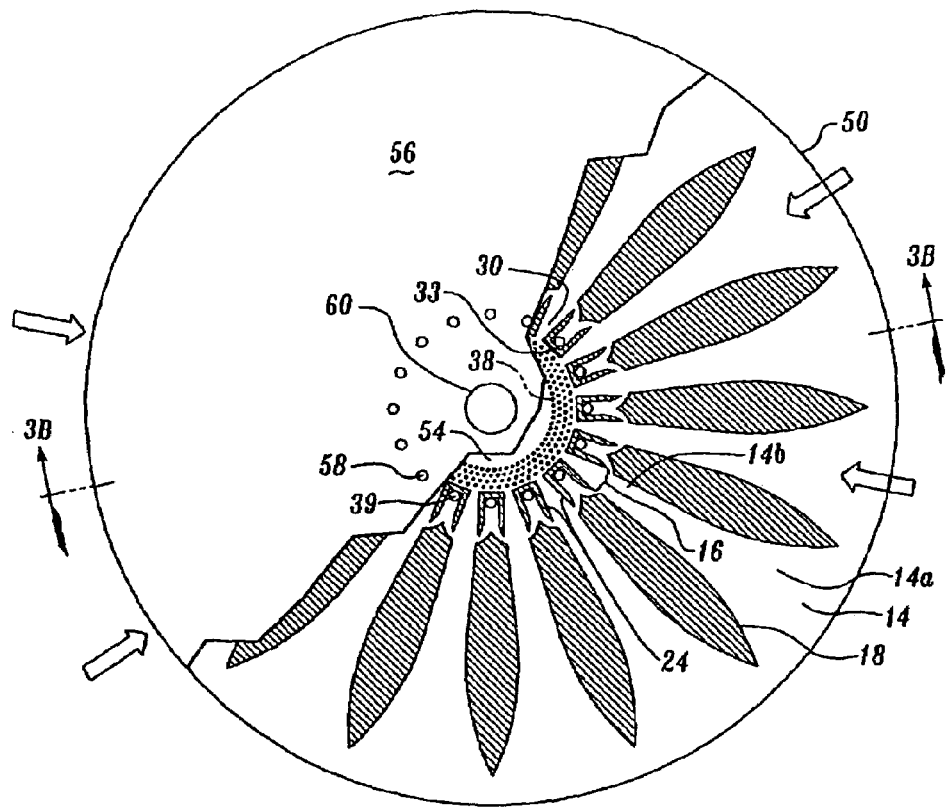
FIG. 3A is a plan view of a virtual impact collector incorporating plural pairs of a nozzle and a virtual impactor arranged radially.
Figure 3B:
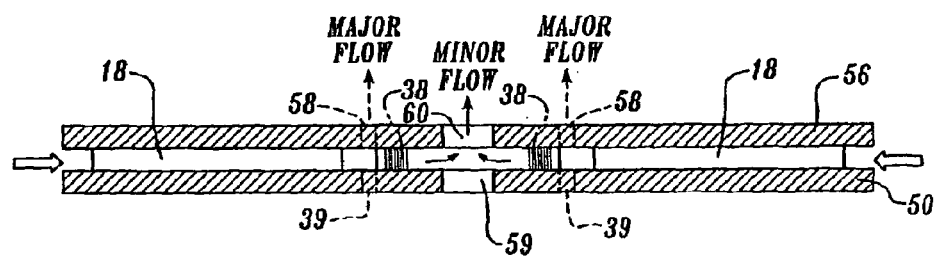
FIG. 3B is a cross-sectional view of the virtual impact collector taken along line 3B-3B of FIG. 3A.

FIGS. 3A and 3B schematically illustrate a radial virtual impact collector including a separation plate 50 and a cover plate 56, in accord with the present invention. Separation plate 50 includes plural pairs of nozzles 14 and virtual impactors 16; the virtual impactors are disposed radially inward of nozzles 14. As before, nozzle 14, which has an inlet end 14a and an outlet end 14b, is defined between adjacent nozzle projections 18. Virtual impactor 16 comprises a pair of fin-shaped projections 24 disposed downstream and radially inward of outlet end 14b of each nozzle 14. As before, fin-shaped projections 24 in each pair are spaced apart and define minor flow passage 30 there between. Also as before, a plurality of virtual impactor bodies 33 in the form of a wall extend between the downstream ends of fin-shaped projections 24 of adjacent virtual impactors 16. A plurality of orifices 39 are provided through separation plate 50 radially outward of virtual impactor bodies 33 and between fin-shaped projections 24 of adjacent virtual impactors 16. Virtual impactors 16 and bodies 33 together define a central minor flow collection portion 54. A plurality of impactor pillars 38 are disposed radially inward and downstream of minor flow passages 30, within central minor flow collection portion 54. Impactor pillars 38 are employed to receive a minor flow and to collect particulates thereon, as more fully described below. A minor flow outlet 59 is provided through separation plate 50 near the center of central minor flow collection portion 54. Separation plate 50, which is described above, may be combined with cover plate 56 to form the virtual impact collector. Cover plate 56 is configured to mate with separation plate 50 to define a chamber there between. Cover plate 56 optionally include holes 58 that are configured and arranged so that when separation plate 50 and cover plate 56 are combined, holes 58 are aligned to coincide with holes 39 defined through separation plate 50. Optionally, cover plate 56 may include a minor flow outlet 60 defined there through. Minor flow outlet 60 is configured so that when cover plate 56 and separation plate 50 are combined, minor flow outlet 60 of cover plate 56 aligns with minor flow outlet 59 of separation plate 50. Holes 39 of separation plate 50 and/or holes 58 of cover plate 56 provide a major flow outlet to the chamber. Minor flow outlet 59 of separation plate 50 and/or minor flow outlet 60 of cover plate 56 provide a minor flow exhaust to the chamber.

In operation, particulate-laden fluid streams enter nozzles 14 through inlet ends 14a and advance radially inward. When aerodynamically focused fluid streams advance toward virtual impactors 16, they are separated into a minor flow and a major flow, as described above. The major flow flows around virtual impactors 16, is redirected by bodies 33, and is exhausted through either or both of holes 39 in separation plate 50 and/or holes 58 in cover plate 56. The minor flow advances through minor flow passages 30 into central minor flow collection portion 54. When impactor pillars 38 are provided, some of the particulates entrained in the minor flow may impact and become deposited on impactors 38. The particulates collected on impactor pillars 38 may be subsequently collected, for example, by washing impactor pillars 38 with a small amount of liquid to capture the particulates therein. An example of impactors suitable for use in conjunction with the present invention can be found in copending U.S. patent application Ser. No. 09/191,979, filed Nov. 13, 1998, concurrently with the parent case hereof, and assigned to the same assignee, which is herein expressly incorporated by reference. The minor flow may be exhausted from central minor flow collection portion 54 through either or both of minor flow outlets 59 and 60.

When both minor flow outlets 59 and 60, and both holes 39 and 58 are provided, as illustrated in FIG. 3B, a plurality of the virtual impact collectors described above may be stacked together to process large amounts of fluid streams. The stacked virtual impact collectors include a common minor flow exhaust conduit comprising minor flow outlets 59 and 60, and a common major flow exhaust conduit comprising holes 39 and 58.

Figure 4A:
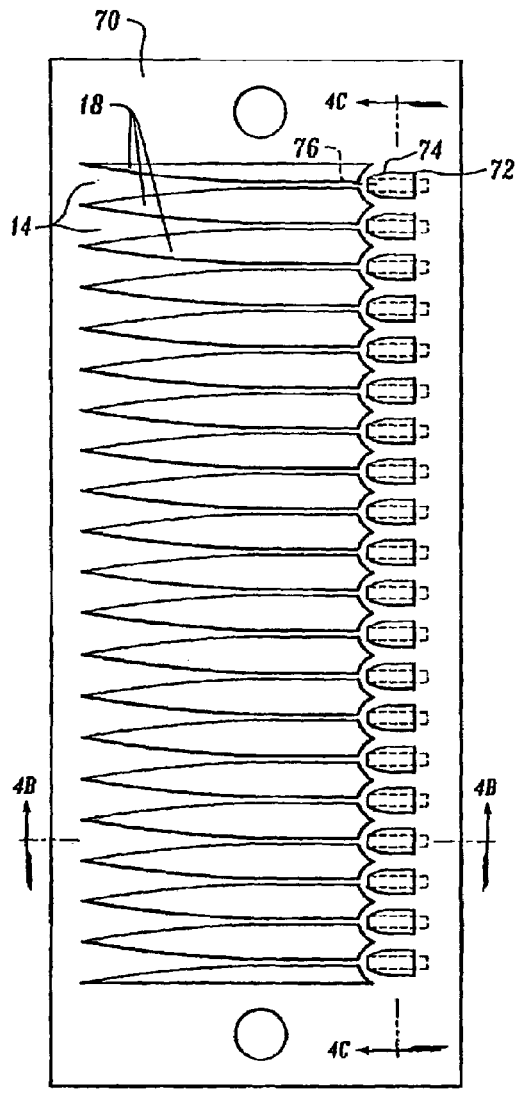
FIG. 4A is a plan view of another configuration of a separation plate in accordance with the present invention.
Figure 4C:
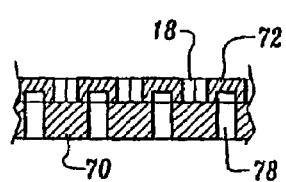
FIG. 4C is a cross-sectional view of the separation plate taken along line 4C-4C of FIG. 4A.
Figure 4B:
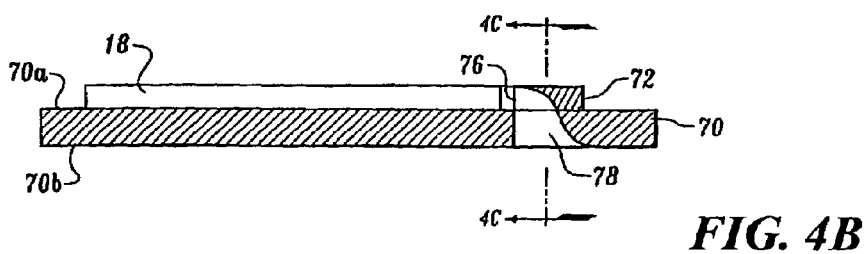
FIG. 4B is a cross-sectional view of the separation plate taken along line 4B-4B of FIG. 4A.

FIGS. 4A, 4B, and 4C illustrate another embodiment of a separation plate 70 in accordance with the present invention. As in the first embodiment, separation plate 70 includes a first surface 70a and an opposing second surface 70b. First surface 70a is provided with a plurality of nozzle projections 18 that define nozzles 14 there between. As before, nozzle 14 tapers from an inlet end 14a to an outlet end 14b. Downstream of each outlet end 14b, a generally haystack-shaped virtual impactor projection 72 is provided. Virtual impactor projection 72 includes a convex leading surface 74 facing the fluid flow. A virtual impact void 76 is provided through convex surface 74 near its apex. Virtual impact void 76 defines a terminal end of a minor flow passage 78 that extends down and through separation plate 70. Minor flow passage 78 and virtual impact void 76 may be formed by, for example, boring an end-mill through second surface 70b of separation plate 70. Alternatively, minor flow passage 78 and virtual impact void 76 may be formed by drilling a hole through separation plate 70. When drilling a hole, minor flow passage 78 preferably passes through separation plate 70 at an acute angle so that a minor flow containing a major portion of particulates will avoid sharp changes in direction upon entering virtual impact void 76. It should be noted that the longer minor flow passage 78, the more particulates may be deposited on the inner surfaces of minor flow passage 78. Therefore, while the angle of minor flow passage 78 should be as acute as possible, the length of minor flow passage 78 cannot be indefinitely long. The optimum combination of the angle and the length of minor flow passage 78 is to be determined based partly on the limitations imposed by the available micro-machining methods. An angle of between approximately 15.degree. and 45.degree., which is possible with currently available micro-machining methods, should provide satisfactory results.

In operation, particulate-laden fluid streams flow along first surface 10a through nozzles 14 and advance toward convex surfaces 74 of virtual impactor projections 72. Major flows continue around projections 72 to avoid obstruction presented by convex surfaces 74, and flow along first surface 10a. Minor flows are collected in a zone of stagnant fluid created near convex surfaces 74, and enter virtual impact voids 76 defined through convex surfaces 74. The minor flows travel through minor flow passages 78 to second surface 70b, where they can be collected, and analyzed or processed after being archived, as discussed below. Thus, unlike separation plates 10 and 50 of the previous embodiments, separation plate 70 of the present embodiment separates a particulate-laden fluid stream into a minor flow on the second surface, and a major flow on the first surface.

Another embodiment of a separation plate 100 is illustrated in FIGS. 5A and 5B. A separation plate 100 includes a central passage 102 that extends laterally across the length of the separation plate and through its width. The passage is defined between plates 104a and 104b and is machined within the facing surfaces of these two plates, which preferably comprise a metal such as steel, aluminum, or titanium, or a another suitable material such as plastic. Alternatively, the passage can be formed by molding or casting the plates from metal, or another suitable material, such as plastic. Passage 102 is readily formed in the surfaces of each of plates 104a and 104b by conventional machining techniques. Since the surfaces are fully exposed, the desired telescoping or converging configuration of the passage is readily formed. The passage extends from an inlet 108, which is substantially greater in cross-sectional area due to its greater height compared to that of an outlet 106. The outlet is disposed on the opposite side of the separation plate from the inlet. Inlet 108 tapers to a convergent nozzle 110, which further tapers to the opening into a minor flow portion 112 of passage 102.

In this preferred embodiment of separation plate 100, one-half of the thickness of passage 102 is formed in plate 104a, and the other half of the thickness of the passage is formed in plate 104b. However, it is also contemplated that the portions of the passage defined in each of plates 104a and 104b need not be symmetrical or identical, since a desired configuration for passage 102 can be asymmetric relative to the facing opposed surfaces of the two plates.

Immediately distal of the point where minor flow portion 112 of passage 102 begins, slots 115a and 115b are defined and extend transversely into the plates relative to the direction between the inlet and the outlet of passage 102 and extend laterally across separation plate 100 between the sides of the passage. Slots 115a and 115b respectively open into major flow outlet ports 114a and 114b in the ends of plates 104a and 104b, as shown in FIG. 5A. Threaded fastener holes 116 are disposed on opposite sides of each of major flow outlet ports 114a and 114b and are used for connecting a major flow manifold (not shown) that receives the major flow of fluid in which the minor portion of the particulates greater than the cut size is entrained.

Fastener holes 118a are formed through plate 104b adjacent to its four corners and do not include threads. Threaded fasteners (not shown) are intended to be inserted through holes 118a and threaded into holes 118b, which are formed at corresponding corner positions on plate 104a. The threaded fasteners thus couple edge seals 120 on the two plates together, sealing the edges of passage 102 and connecting plates 104a and 104b to form separation plate 100. Although not shown, a manifold may also be connected to the back surface of separation plate 100 overlying outlet 106 to collect the minor flow of fluid in which the major portion of particulates exceeding the cut size is entrained. In FIG. 5A, the flow of fluid entering inlet 108 of passage 102 is indicated by the large arrow, the major flow exiting major flow ports 114a and 114b is indicated by the solid line arrows, and the minor flow exiting outlet 106 of passage 102 is indicated by the dash line arrow. The cross-sectional profile of passage 102 as shown in FIG. 5B focuses the particulate-laden fluid flow entering inlet 106 for delivery to the receiving nozzle and thus performs in much the same way as the profile used in the previous embodiments of virtual impactors.

The desired flow through the separation plate will determine the width of passage 102, as measured along the longitudinal axis of the separation plate, between sealed edges 120. Additional fluid flow can also be accommodated by providing a plurality of the separation plates in an array, which will also avoid using extremely long and thin structures that may not fit within an available space. FIG. 5B illustrates two such additional separation plates 100' and 100", stacked on each side of separation plate 100, so that the fluid enters the inlets of the stacked separation plates and is separated in the major flow and the minor flow exiting the separation plates, as described above.

FIGS. 6A and 6B illustrate still another embodiment of a separation plate 200 that is similar to separation plate 100, which was discussed above in regard to FIGS. 5A and 5B. Separation plate 200 differs from separation plate 100 in at least two significant ways, as will be apparent from the following discussion. To simplify the following explanation of separation plate 200, the reference numbers applied to its elements that are similar in function to those of separation plate 100 are greater by 100. Thus, like central passage 102 in separation plate 100, separation plate 200 includes a central passage 202 that extends laterally across the length of the separation plate and through its width. The passage is defined between plates 204a and 204b and is machined within the facing surfaces of these two plates, which also preferably comprise a metal such as steel, aluminum, or titanium formed by machining or by molding the plates from metal, or another suitable material, such as a plastic. The passage extends from an inlet 208, which is substantially greater in cross-sectional area due to its greater height, to an outlet 206 disposed on the opposite side of the separation plate from the inlet. Unlike inlet 108 of the previous embodiment, which tapers to a convergent nozzle 110 and then to a minor flow portion 112 of passage 102, the central passage in separation plate 200 does not taper to smaller cross-sectional sizes. Instead, the central passage in separation plate 200 changes abruptly to a smaller cross-sectional size at a step 222, continuing through a section 210, and then again decrease abruptly to a smaller minor flow outlet 212, at a step 224. At each of steps 222 and 224, a swirling flow or vortex 226 of the fluid is produced. It has been empirically determined that these vortexes tend to focus the particulates toward the center of the passage, thereby providing a substantial improvement in the efficiency with which the particulates smaller than the cut size are separated from the particulates larger than the cut size.

In this preferred embodiment of separation plate 200, one-half the thickness of passage 202 is formed in plate 204a, and the other half of the thickness of the passage is formed in plate 204b, just as in the previous embodiment. Again, it is contemplated that the portions of the passage defined in each of plates 204a and 204b need not be symmetrical or identical, since a desired configuration for passage 202 can be asymmetric relative to the facing opposed surfaces of the two plates.

Immediately distal of the point where minor flow portion 212 of passage 202 begins, slots 215a and 215b are defined and extend transversely into the plates relative to the direction between the inlet and the outlet of passage 202 and extend laterally across separation plate 200 between the sides of the passage, just as in separation plate 100. Slots 215a and 215b respectively open into major flow outlet ports 217a and 217b, which are open to the ends and outer surfaces of plates 204a and 204b, as shown in FIG. 6A. In this embodiment, separation plate 200 is designed to be stacked with other similar separation plates 200' and 200", as shown in FIG. 6B, so that adjacent separation plates cooperate in forming the passage for conveying the major flow into an overlying major flow manifold (not shown). It is also contemplated that separation plate 100 can be configured to include major flow outlet ports similar to those in separation plate 200. The last plate disposed at the top and bottom of a stack of separation plates configured like those in FIG. 6B would include major flow outlet ports 114a and 114b, respectively. Threaded fastener holes 216 are disposed on opposite sides of each of major flow outlet ports 217a and 217b and are used for connecting a major flow manifold (not shown) that receives the major flow of fluid in which the minor portion of the particulates greater than the cut size is entrained.

Fastener holes 218a are formed through plate 204b adjacent to its four corners and do not include threads. Threaded fasteners (not shown) are intended to be inserted through holes 218a and threaded into holes 218b, which are formed at corresponding corner positions on plate 204a. The threaded fasteners thus couple edge seals 220 on the two plates together, sealing the edges of passage 202 and connecting plates 204a and 204b to form separation plate 200. Although not shown, a manifold may also be connected to the back surface of separation plate 200 overlying outlet 206 to collect the minor flow of fluid in which the major portion of particulates exceeding the cut size is entrained, for use in creating an archive of the samples thus collected as explained below. In FIG. 6A, the flow of fluid entering inlet 208 of passage 202 is indicated by the large arrow, the major flow exiting major flow outlet ports 217a and 217b is indicated by the solid line arrows, and the minor flow exiting outlet 206 of passage 202 is indicated by the dash line arrow.

Separation plates 100 and 200 costs less to manufacture than the other embodiments discussed above. As was the case with separation plate 100, the desired flow through the separation plate will determine the width of passage 202 along the longitudinal axis of the separation plate, between sealed edges 220, and additional fluid flow can also be accommodated by providing a plurality of the separation plates in an array configured to fit within an available space. FIG. 6B illustrates two additional separation plates 200' and 200", stacked on opposite sides of separation plate 200, so that the fluid enters the inlets of the stacked separation plates and is separated in the major flow and the minor flow exiting the separations plates, as described above.

Figure 7:
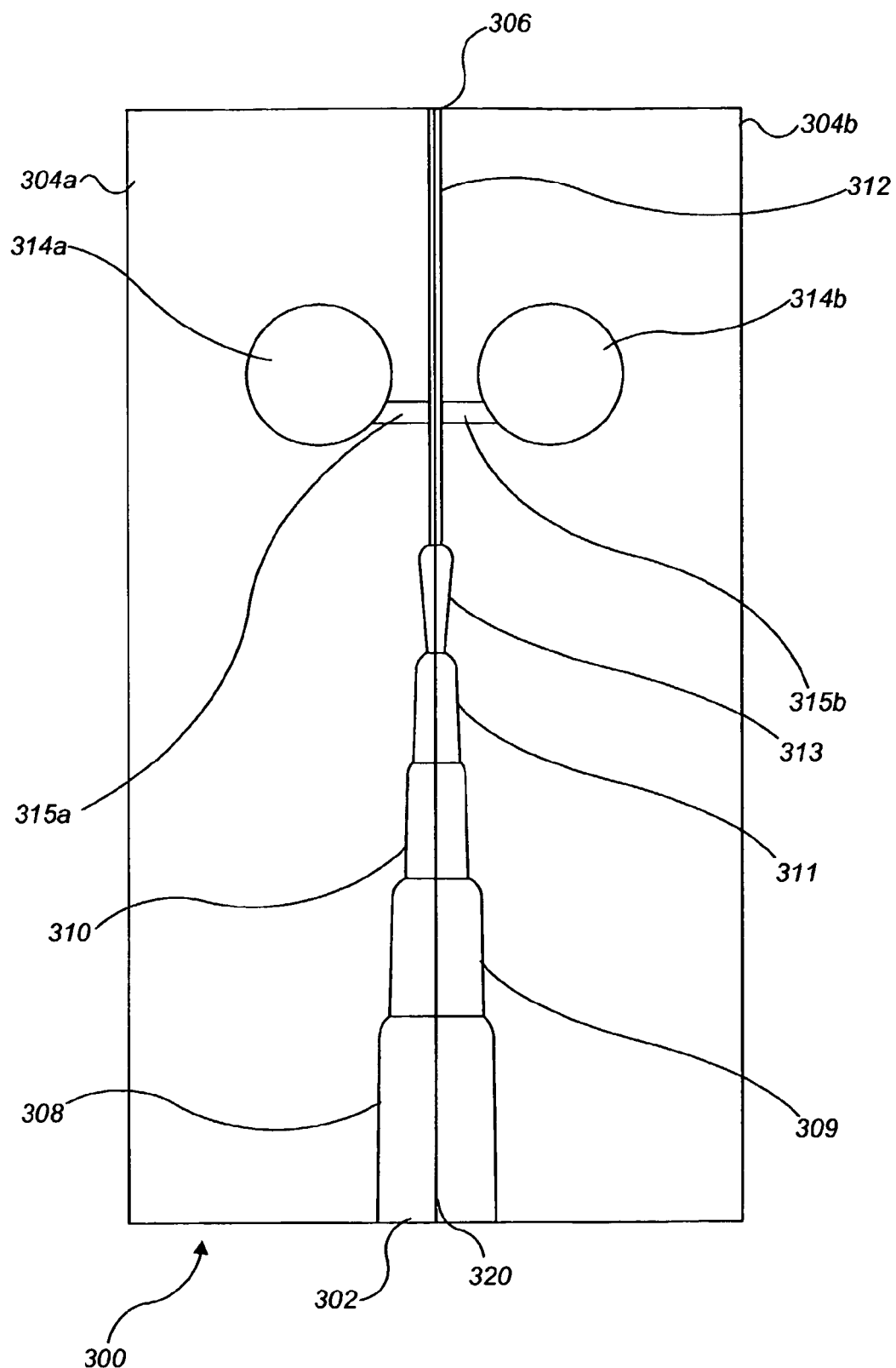
FIG. 7 is a cross-sectional view of a separation plate like that shown in FIGS. 5A and 5B, but having a slightly modified passage through which the fluid flows to optimize the efficiency of separation over a broader range of particulate sizes.
Figure 8:
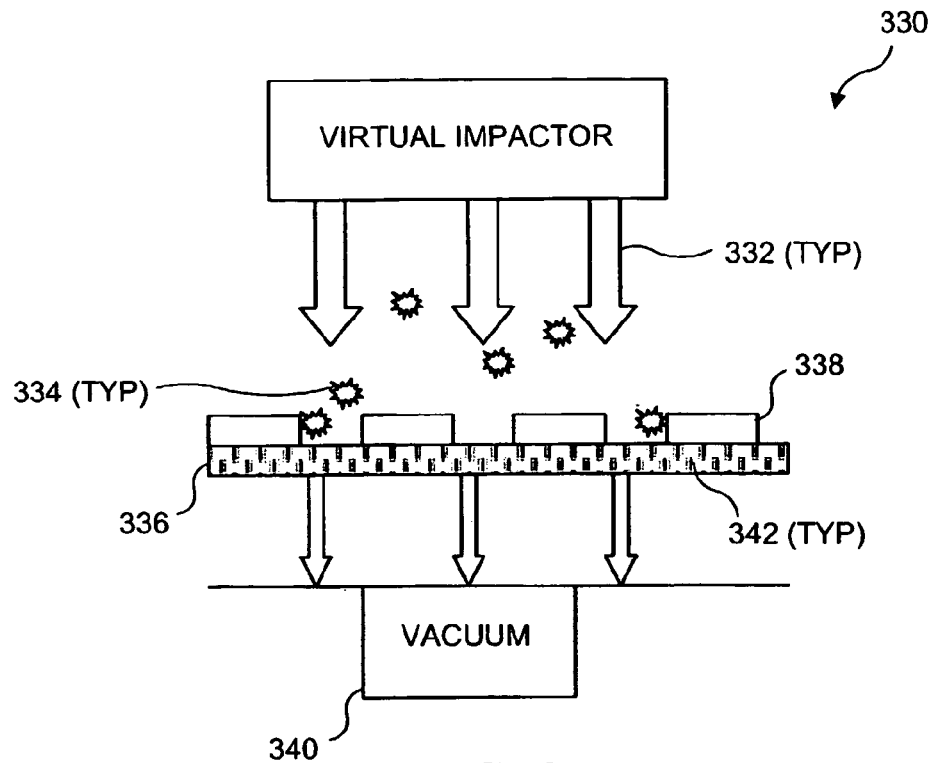
FIG. 8 is a schematic view of a porous archival impaction surface in accord with one embodiment of the present invention.
Figure 9:
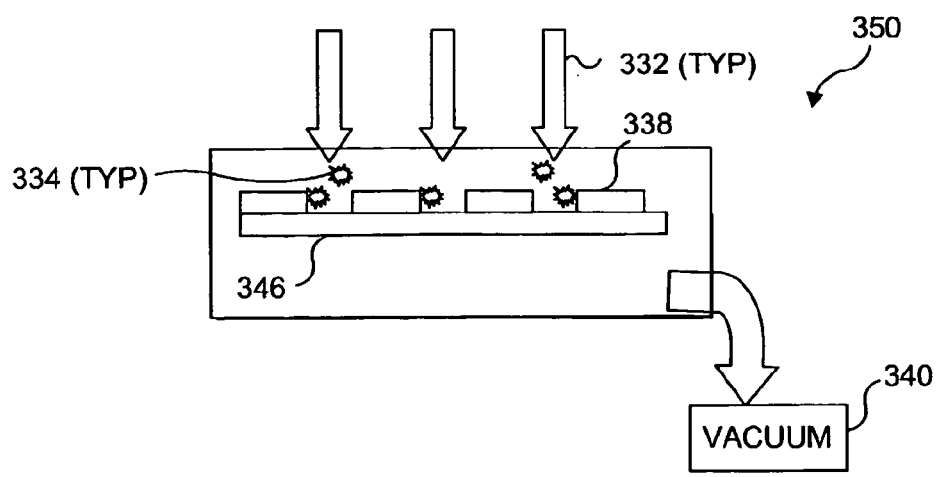
FIG. 9 is a schematic view of a non-porous archival impaction surface in accord with another embodiment of the present invention.

Finally, yet another embodiment of the present invention, a separation plate 300 is illustrated in FIG. 7. Separation plate 300 is also similar to separation plate 100, which is shown in FIGS. 5A and 5B, but includes a central passage 302 that differs from central passage 102 in separation plate 100. Again, to simplify the following explanation, reference numbers applied to the elements of separation plate 300 that are similar in function to those of separation plate 100 are greater by 200. It will thus be apparent that central passage 102 in separation plate 100 corresponds to central passage 302 in separation plate 300 and that central passage 302 extends laterally across the length of separation plate 300 and through its width. The passage is defined between plates 304a and 304b and is machined within the facing surfaces of these two plates, preferably from a metal such as steel, aluminum, or titanium formed by machining, or by molding the plates from metal, or another suitable material, such as a plastic. The passage extends from an inlet 308, which is substantially greater in cross-sectional area due to its greater height, to an outlet 306 disposed on the opposite side of the separation plate from the inlet. Central passage 302 comprises a telescoping section that performs aerodynamic focusing of the particulates so as to achieve a further optimization in maximizing the efficiency of the separation plate over a wider range of particulates sizes, compared to the other embodiments. The focusing is accomplished in this embodiment by using a combination of contracting and diverging sections. Specifically, an inlet 308 tapers slightly at its distal end to a more convergent section 309, which again tapers to a convergent nozzle 310, which further tapers at its distal end to another convergent section 311. The distal end of convergent section 311 tapers into the proximal end of a divergent section 313, and its distal end then tapers into a minor flow portion 312 of central passage 302. Distal of the point where minor flow portion 312 of central passage 302 begins, slots 315a and 315b are defined and extend transversely into the plates relative to the direction between the inlet and the outlet of central passage 302 and extend laterally across separation plate 300 between the sides of the passage. Major flow outlet ports 314a and 314b can be used for connecting to a major flow manifold (not shown) that receives the major flow of fluid in which the minor portion of the particulates greater than the cut size is entrained.

As will be apparent from the preceding description, a number of gentler steps are used in the central passage of separation plate 300 than in the preceding embodiments of FIGS. 5A and 5B, and 6A and 6B, to improve the efficiency of separating larger particulates (i.e., approximately 5.mu. to 10.mu. in size); larger particulates tend to have greater wall losses due to impaction on the "steps" of the telescoping profile. The gentler steps will not focus the small particulates as well as in the other embodiments, however, so the outward expansion provided by diverging section 313, followed by a final steep step into minor flow passage 312 to focus the small particulates seems to improve the efficiency of the separation (at least in simulations). The flow of larger particulates does not expand out much in diverging section 313, and is thus less likely to impact on the final step into minor flow passage 312.

In all other respects, separation plate 300 operates like separation plate 100, and can be modified to collect the major flow like separation plate 200. It will also be apparent that a plurality of separation plates 300 can be stacked, just as in the previous embodiments, to increase the volume of fluid processed.

Particulate Collection

Once the particulate concentration of the fluid stream has been enhanced by the use of a virtual impactor as described above, collection of the concentrated particulates can be effected. It should be noted that impact based collectors (as opposed to the virtual impact collectors described above) can also achieve significant particulate concentrations. However, the impact surface portion of such impact collectors is generally an integral portion of the impact collector, and it is not practical to archive the impact collector itself. The collection surface of impact collectors is generally rinsed with a fluid to obtain the collected particulates for analysis. While such particulates collected in that fashion could also be archived, the volume of fluid required to rinse the collected particulates from the impact collector significantly increases the volume of material that must be archived. Furthermore, the steps of rinsing, collecting, and storing the rinsate add significant time and effort (and thus cost) to archiving particulates. The use of a virtual impactor enables an archival surface to be employed that is a separate component. Such a separate component can be readily removed from the virtual impactor and replaced with a fresh surface for collecting particulate samples. The archival surface on which the sample have been collected can then be stored without significant additional processing until needed.

Any surface material amenable to spot deposition can be used. The present invention contemplates several different deposition methods. A first method involves directing the minor flow described above toward a filter through which the fluid in the minor flow can pass and upon which the particulates are deposited. In a different embodiment, the particulates are directed toward an impaction surface that is enveloped in a vacuum system. The archival (impaction) surface can also be coated with a material that aids in the deposition and retention of particulates that have impacted on the surface.

FIG. 8 schematically illustrates an archival collection system 330 that uses a porous hydrophilic filter medium 336 as the deposition surface. Preferably a hydrophobic material 338 would be deposited on top of porous hydrophilic filter medium 336. Openings 342 in hydrophobic material 338 direct particulates 334 entrained in a minor flow 332 toward locations on porous hydrophilic filter medium 336 that particulates will be collected upon. The fluid in which the particulates are entrained passes through the porous hydrophilic filter medium 336, leaving the particulates deposited on the surface. A vacuum source 340 can be beneficially employed to ensure that the minor flow fluid passes through the porous filter, rather than being diverted around sides of the porous filter.

Preferably the area between the introduction of the minor flow and the filter is sealed, so the particulates will not be lost prior to impact. The sealing preferably extends between the bottom of the porous filter and vacuum source 340. While not readily apparent from FIG. 8, it should be understood that porous hydrophilic filter medium 336 moves relative to the position of the minor flow, so that particulates collected from the minor flow at different times are associated with different (and known) locations on the porous filter. In general, it is anticipated that it will be simpler to move the archival surface than the virtual impactor, although movement of either the virtual impactor or the archival surface will enable particulates to be deposited on specific spaced-apart portions of the archival surface as a function of time. Regardless of which component is moved, preferably any sealing system employed should be capable of accommodating the required movement.

As shown in FIGS. 8 and 9, the minor flow is directed towards the archival surface as three separate streams. It should be understood that either few or more than three minor flow streams could alternatively be employed as well. The benefit of employing multiple minor flows is that, as described above, individual virtual impactors can be fabricated to selectively direct particulates of a desired size into the minor flow. Thus, by employing a plurality of virtual impactors, each concentrating a different particulate size into their respective minor flows, particulates of different sizes can be directed onto different locations of an archival surface. Alternately, particulates of the same size can be deposited in different locations, permitting duplication of sampling to occur, to facilitate multiple testing, perhaps at different times.

FIG. 9 schematically illustrates an archival collection system 350 that uses a non-porous archival surface 346 as the deposition surface. In archival collection system 350, the particulate-laden fluid is accelerated through a minor flow outlet nozzle of a virtual impactor to impact the surface. Preventing particulates from bouncing off of non-porous archival surface 346 is a key aspect of this approach.

Note that in both FIGS. 8 and 9, a surface coating or layer has been applied on top of the archival surface to define receptacles for spots. Such a coating (hydrophobic material 338) is not required, but is a useful addition. Regardless of whether a porous or non-porous archival surface is employed, several different surface treatments may be useful in increasing the efficiency of spot formation. For example, a common problem with surface impaction is that particles bounce off the surface, return to the fluid stream, and are swept away. It is preferable to coat the surface to promote particle adhesion. Such surface coatings include, but are not limited to, charged chemical species, proteins, and viscous substances that increase the impact force required to enable the particulates to bounce away from the archival surface. Details of exemplary coatings that can be beneficially employed in the present invention are described below. It should be noted that a person skilled in the art will recognize that many other coatings, having other physical and chemical properties, can be beneficially employed to aid in the collection of specific types of particulates. In at least one embodiment, the coating is on the order of 100 microns thick, while the archival surface itself is in the order of 100 millimeters thick.

It should be noted that the archival surface, with or without a coating, need not be flat. Preferentially, a surface with portions raised significantly above the bulk of the surface can also be used to collect spots of particulates. For example, a textured surface with portions raised substantially above a background portion of the surface can be used to collect spots of particulates. Such textured surfaces are disclosed in commonly assigned U.S. Pat. No. 6,110,247, the disclosure and drawings of which are hereby specifically incorporated herein by reference. Such surfaces reduce the tendency of particles to bounce and therefore increase spot formation efficiency.

Archival Surface Coatings

FIGS. 10 and 11 schematically illustrate how coating an impact collection surface, such as an archival surface, with a material can substantially enhance the efficiency of that surface. FIG. 10 shows a fluid 410 in which particulates 414 are entrained, moving relative to a (prior art) impact collection surface 412 that is not coated. Particulates 414 are separated from the fluid by striking against impact collection surface 412. FIG. 11 shows fluid 410 moving toward a coated impact collection surface 416, which has been coated with a material that retains substantially more of the particulates entrained in fluid 410 than would an uncoated surface. By comparing FIGS. 10 and 11, it will be apparent that substantially more particulates 414 are collected on coated impact collection surface 416 than on impact collection surface 412.

The relatively greater density of particulates 414 evident on coated impact collection surface 416, compared to impact collection surface 412, is due to a characteristic of the coating that causes it to better retain particulates and thus more efficiently separate the particulates from the fluid in which they are entrained, compared to the prior art impact collection surface that is not coated. In the embodiment of the present invention shown in FIG. 11, the geometry of impact collection surface 416 is generally irrelevant. The coating of the present invention can be applied to the impact collection surfaces in almost any impact collector or virtual impact collector. Simply by coating surfaces on which a stream of particles impacts with one of the materials described below, a substantial increase in the efficiency with which the particulates are separated from a fluid and collected is achieved.

FIG. 12 schematically illustrates an embodiment of the present invention in which a plurality of coated areas 418 are applied to an upper exposed surface of an elongate tape 420. As illustrated in this Figure, tape 420 is advanced from left to right, i.e., in the direction indicated by an arrow 422. Tape 420 thus moves past a stream 421 of fluid 410 in which particulates 414 are entrained. Stream 421 is directed toward the upper surface of the tape. As the tape advances, fresh coated areas 418 are exposed to impact by particulates 414. The particulates that impact on these coated areas are at least initially retained thereon, as shown in coated areas 418a. In the embodiment illustrated in FIG. 12, coated areas 418 and 418a are not contiguous, but instead are discrete patches disposed in spaced-apart array along the longitudinal axis of tape 420. Various types of material described below can be used to produce coated areas 418.

In an alternative embodiment shown in FIG. 13, a continuous coated impact collection surface 423 extends longitudinally along the center of a tape 420'. As tape 420' advances in the direction indicated by arrow 422, stream 421 of fluid 410 with entrained particulates 414 is directed toward the upper surface of the tape. Particulates 414 are retained by the coating, as shown in a coated impact collection surface 423a. As tape 420' advances in direction 422, coated impact collection surface 423 is exposed to impact by particulates 414 carried in stream 421. In the embodiment that is illustrated, the coating does not cover the entire upper surface of tape 420'. However, it should be understood that any portion or the entire upper surface of tape 420' can be covered with the coating.

The material used for producing coated impact collection surface 423 and other coated areas or surfaces employed in this description for collecting particulates in accord with the present invention is selected because of certain characteristics of the material that increase the efficiency with which the particulates are separated from the fluid in which they are entrained. Each material used for a coating has certain advantages that may make it preferable compared to other materials for separating a specific type of particulate from a specific type of fluid. For example, for use in collecting particulates in a dry air or other dry fluid, a material called TETRAGLYME can be used to for the coating. This material is hydrophilic until it is exposed to water and when dry, is relatively very sticky, tending to readily retain particulates that impact it. However, once water is sprayed onto the TETRAGLYME coated surface so that it is wetted, the coating becomes hydrophobic. When hydrophobic, the TETRAGLYME coated surface is no longer sticky or tacky, and in fact, readily releases the particulates that previously were retained by it. The water (or other liquid containing water) easily washes the particulates away from the coated impact collection surface. TETRAGLYME, which is available from chemical supply houses, is bis(2-[methoxyethoxy]ethyl) ether tetraethylene glycol dimethyl ether dimethoxy tetraethylene glycol and has the formula: $CH_3OCH_2$ $(CH_2OCH_2)_3CH_2OCH_3$ $CH_3$—O—$CH_2$—$CH_2$—O—$CH_2$—$CH_2$—O—$CH_2$—$CH_2$—O—$CH_2$—$CH_2$—O—$CH_3$. Tests have shown that TETRAGLYME coating can collect more than three times as many particulates as an uncoated surface. Water molecules are retained by the molecule by links to the oxygen atoms, as shown below.

$$O:H_2O:O$$

A second type of material usable for a coated particulate collection surface is PARYLENE, which is a tetrafluoromore manufactured and sold by DuPont Chemical Company under the trademark INSUL-COTE.™., Type N. The PARYLENE material is characterized by a relatively low coefficient of friction, causing it to be extremely slippery and not sticky. Accordingly, particulates impacting against a coated surface comprising PARYLENE are initially separated from the fluid in which they are carried by the impact with the coated surface and are initially retained by the coated surface. However, these particulates are readily washed away from the PARYLENE coated surface by water or other liquid sprayed onto the coating. The particulates retained by a PARYLENE coated surface on tape 420' are readily washed away from the coating by water or other liquid spray.

The TETRAGLYME material is an example of a class of materials that has two distinct states related to particulate collection. When dry and hydrophilic, the TETRAGLYME material is in a first state, in which it is sticky and is very efficient at separating particulates from the fluid in which they are entrained, compared to an uncoated surface. However, when wetted, the TETRAGLYME material changes to its second state, in which it readily releases the particulates.

Figure 14:
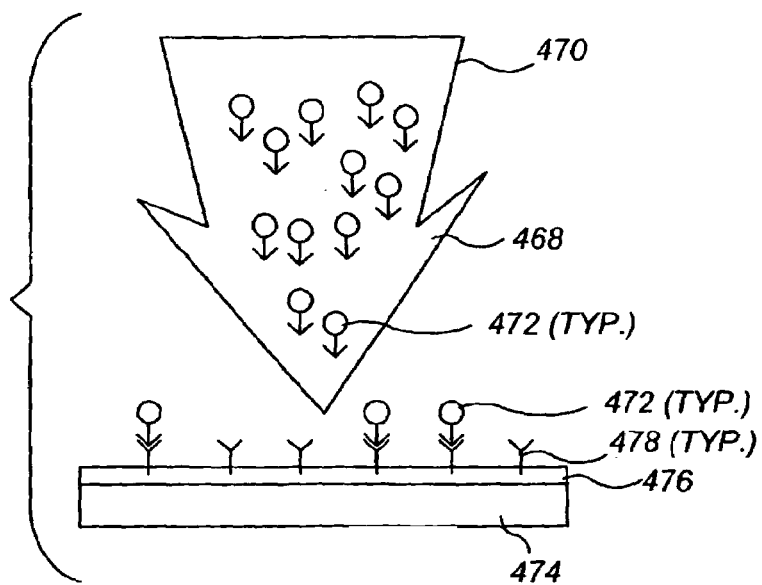
FIG. 14 is a schematic illustration illustrating an impact collection surface coated with a material that includes antibodies selected to link with an antigen on a specific biological particulate.

As shown in FIG. 14, a mono-layer material 476 can be applied to a surface 474 of a particulate collector to separate specific biological particulates 472 from a fluid 468 such as air or a liquid in which they are entrained. It is contemplated that the fluid conveying the biological particulates may also include blood. A stream 470 of the biological particulates is directed at material 476, so that the biological particulates impact thereon. Mono-layer material 476 comprises a plurality of antibodies 478 that are selected to link with the antigens on biological particulates 472. For example, if biological particulates 472 comprise anthrax spores, and antibodies 478 are selected that are specific to anthrax spores, the anthrax spores will be readily separated and retained by linking with the antibodies on the coating. These anthrax spores may then be identified based upon an appropriate analysis. The type of analysis employed is outside the scope of this disclosure. Those of ordinary skill in the art will recognize that based on the nature of the targeted particulates, a specific analytical procedure may be more or less appropriate.

Figure 15A:
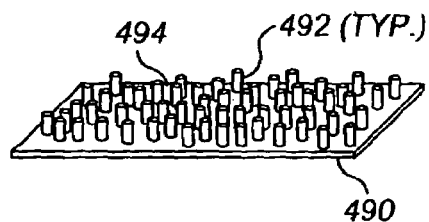
FIGS. 15A and 15B illustrate two embodiments in which outwardly projecting structures are provided on an impact collection surface to enhance particulate collection.
Figure 15B:
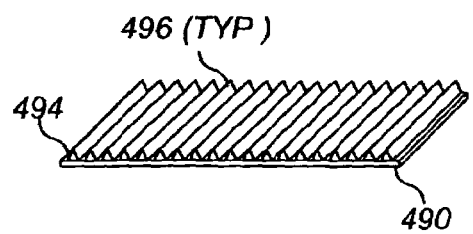

It is also contemplated that the coated impact collection surface need not be planar. Indeed, it is likely that enhanced particulate collection efficiency can be achieved by using a non-planar coated surface to collect particulates. FIG. 15A illustrates an enlarged view of a portion of one preferred embodiment for a textured particulate collection surface 490 having a plurality of outwardly projecting rods 492 distributed thereon. The outwardly projecting rods increase the surface area of particulate collection surface 490, which is provided with a coating 494 of one of the coating materials discussed above, and also increase the "roughness" of the surface to further enhance the collection efficiency of the coating. Coating 494 may be applied over rods 492 or applied before the rods are attached. Alternatively, other projecting structures such as ribs 496 may be employed on textured particulate collection surface 490, as shown in FIG. 15B.

In at least one embodiment, the archival surface incorporates a material that helps maintain the particulates deposited on the archival surface in good condition, without substantial degradation. For some particles, such as living cells, this material may be a liquid that contains nutrients. Applying a hydrogel or equivalent coating on the archival surface would allow localization of water. The water can be used to deliver salts, sugars, proteins, and other nutrients to enable the cells to survive on the archival surface during the time interval between deposition on the archival surface and subsequent analysis of the collected samples of particulates.

Figure 18A:
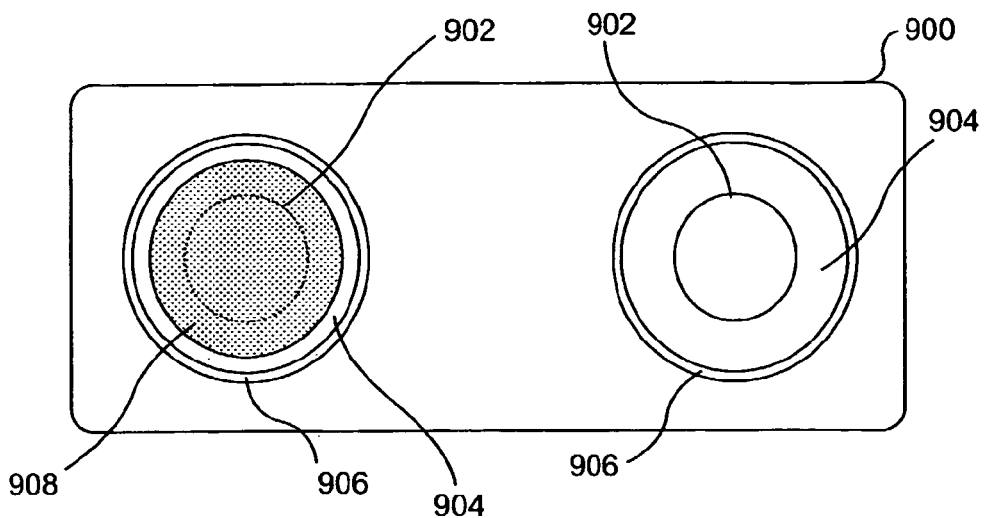
FIG. 18A is a plan view of an exemplary ticket including two collection areas for use in an exemplary particle collection system.
Figure 18B:
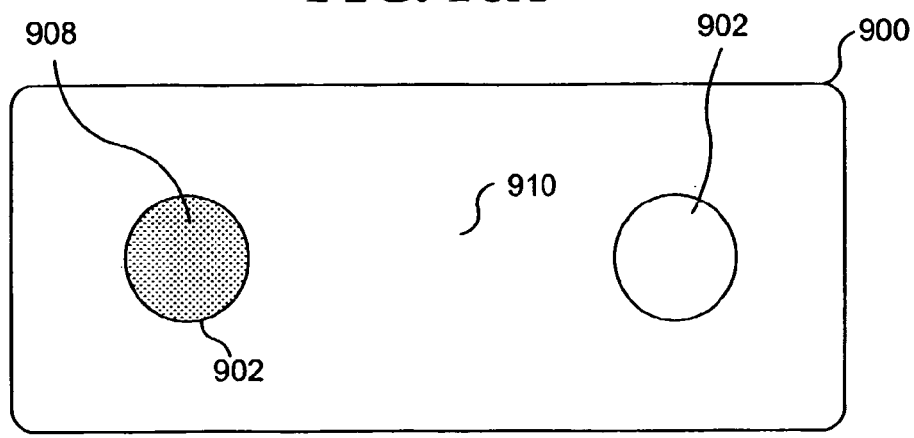
FIG. 18B is a bottom view of the ticket of FIG. 18A.
Figure 18C:
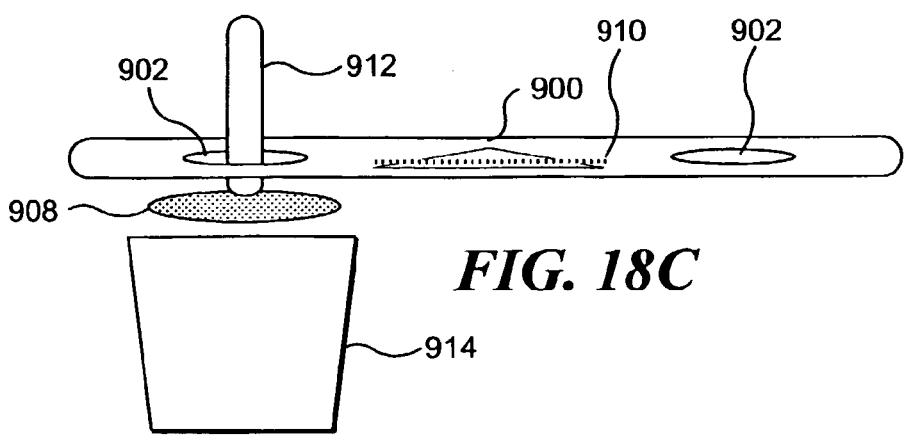
FIG. 18C is a side view of the ticket of FIGS. 18A-B, illustrating a punch being used to remove a disposable collection surface.

For all of the above surfaces, some portion of the analysis/detection scheme could be included as part of the surface. For example, if the analysis employed to detect a specific particulate involves incubating the collected particulates (some of which are likely to be bioparticles) with a reagent, the reagent can be incorporated onto the surface so that the incubation period is initiated upon deposition.

Orientation of Archival Surface Relative to Virtual Impactor

As noted above, because the location of a "spot" of particulates deposited on the archival surface is indicative of a time the particulates were collected, it is preferable to move the archival surface relative to the virtual impactor, at least at spaced-apart times to form spots of particulates (or continually to form streaks of particulates). Moving the archival surface at successive time intervals permits multiple sample spots to be deposited on a single archival surface without commingling the spots. The time at which each spot is deposited is associated with the spot. Alternatively, time can be linear in its association with a position in a streak of particles that are deposited continuously.

One embodiment providing for intermittent relative motion between the archival surface and the adjacent stream of particulates is shown in FIG. 16, in which a virtual impactor 510 is fixedly mounted over a movable archival surface that is formed in the shape of a disk 516. The minor flow of particulates is S directed at the disk. A major flow 512 containing particulates of non target size exits virtual impactor 510 orthogonally with respect to the minor flow, to prevent particulates entrained in the major flow from being deposited on disk 516. While not shown, it should be understood that disk 516 could be further separated from major flow 512 by a protective housing.

The nozzles directing the minor flow toward disk 516 cannot be seen in FIG. 16, but virtual impactor 510 includes three minor flow outlets, all of which are oriented to direct particulates towards spot deposition areas 514*a*-514*c*. As disk 516 rotates beneath virtual impactor 510, the minor flow nozzles of virtual impactor 510 direct particulates to a new deposition area. Note that disk 516 shows three concentric rings of spaced-apart spots in three different annular deposition areas, area 514*a* defining the inner ring of spots, area 514*b* defining a middle ring of spots, and areas 514*c* defining an outer ring of spots. Disk 516 is preferably indexed (not shown) so that the spots are defined at discrete predetermined positions around the deposition areas, that enable the position of each spot to be associated with a specific time, and enable the particulates to be accurately directed toward the disposition of each spot on the disk. It should be understood from FIG. 16, and the preceding description, that deposition areas 514*a*-514*c* preferably each include a plurality of depressions formed into disk 516, either as openings in a coating on disk 516, or depressions formed into the surface of disk 516, where each spot of particulates is to be deposited. However, while such openings/depressions are anticipated to increase collection efficiency, they are not required.

Disk 516 can be moved using an appropriate prime mover 520, such as a stepping motor. As shown, one such means includes a shaft 518 detachably coupled to disk 516 and driven by prime mover 520. It is anticipated that disk 516 will remain stationary for a desired time interval, and then will be rotated a sufficient amount to align another set of depressions in the deposition areas with the minor flow nozzles of virtual impactor 510, so that the spots of particulates can be deposited within the depressions, if depressions are indeed provided. The virtual impactor can be cycled on and off during the movement if desired.

As noted above, is also possible to deposit streaks of particulates instead of spots. In a more elaborate embodiment, the archival surface is continually moved at a fixed rate, resulting in annular rings defined by streaks of particles on the archival surface, instead of discrete spots. The use of streaks somewhat simplifies the operation of the collector, in that it can operate continuously, rather than being cycled on and off.

Note that more or fewer minor flow nozzles can be incorporated into a virtual impactor. Preferably, each virtual impactor minor flow nozzle will be directed to a different location on the archival surface. It should also be noted that different configurations of archival surfaces can be employed (i.e., shapes other than disks), and that different configurations of spots can be deposited on archival surfaces (i.e., configurations other than streaks or concentric rings of spots). FIG. 17A shows a quadrilateral shaped archival surface on which deposition areas 514*d* are oriented in an array extending orthogonally in two directions. FIG. 17B shows a second disk-shaped archival surface, on which deposition areas 514*e* are oriented in a spiral array. It should be understood that any of deposition array 514*a*-514*e* illustrated and discussed above can be one or more of: (1) a depression on the archival surface; (2) an opening in a coating on an archival surface; (3) an aggregate of particulates deposited in a spot; and (4) an area in which an aggregate of particulates are to be deposited without regard to the shape of the deposit.

Exemplary Archival Collection System with Employing Dual Ticket Magazines

One preferred embodiment of an automated system that automatically changes collection surfaces when triggered to do so (or according to a pre-programmed schedule) includes a plurality of tickets. This Indexed Particle Collection System (IPCS) allows multiple samples to be taken without user intervention. Unused collection tickets are stored in a "magazine." When a new sample is needed, the indexed system automatically removes a new collection ticket from the fresh magazine and places it in position for sample collection. When the sample is complete, the collected sample is moved into a spent magazine and a fresh ticket is placed into positioned for collection of the next sample. In a prototype unit up to 24 sample tickets fit in a magazine. Samples can be changed on a pre-programmed time interval or by a trigger signal.

FIG. 18A shows a plan view of an exemplary ticket 900, which preferably includes two collection areas, defined by raised lips 906. In a prototype unit, ticket 900 was fabricated from metal, although other durable materials, such as polymers, can be employed. If tickets are to be reused, they should be fabricated from a material that is easy to sterilize, to avoid cross contamination. Inside each lip 906 is a generally flat surface 904. Generally in the center of each flat surface 904 is an opening 902. A disposable impact surface 908 is placed inside each raised lip 906. In FIGS. 18A-18C, only one impact surface 908 is shown, however, it should be understood that preferably each ticket includes two impact surfaces. While both impact surfaces can be analyzed, it is anticipated that a useful sampling protocol will call for one impact surface to undergo analysis and one impact surface to be archived. As has been generally discussed above, each impact surface is disposed in fluid communication with a minor flow path from a virtual impact collector. As each ticket includes two collection areas, ticket 900 is designed to be employed in a system whose virtual impactor provides two minor flows, spaced apart so that each minor flow is generally directed toward flat surfaces 904, upon which an impact surface will be placed. Also as discussed above, the minor flow is preferably configured to deposit small spots of particles on the impact surfaces.

FIG. 18B is a bottom view of exemplary ticket 900, again showing only a single impact surface 908. Lips 906 are not present on the bottom of the ticket. A logo 910 is included, to provide a reference to ensure that tickets are loaded in the proper orientation. FIG. 18C is a side view of exemplary ticket 900, again showing only a single impact surface 908. One or both of the impact surfaces are removed from the ticket and placed in a sample container 914. A punch 912 or rod can be employed to facilitate the removal of impact surface 908 from ticket 900. Note openings 902 provide access to push the collection surface out of the ticket into the vial to recover the sample. The ticket design gives two parallel samples that can be removed separately, allowing one to be analyzed and one kept in reserve, or allowing parallel analysis to be done.

Figure 18D:
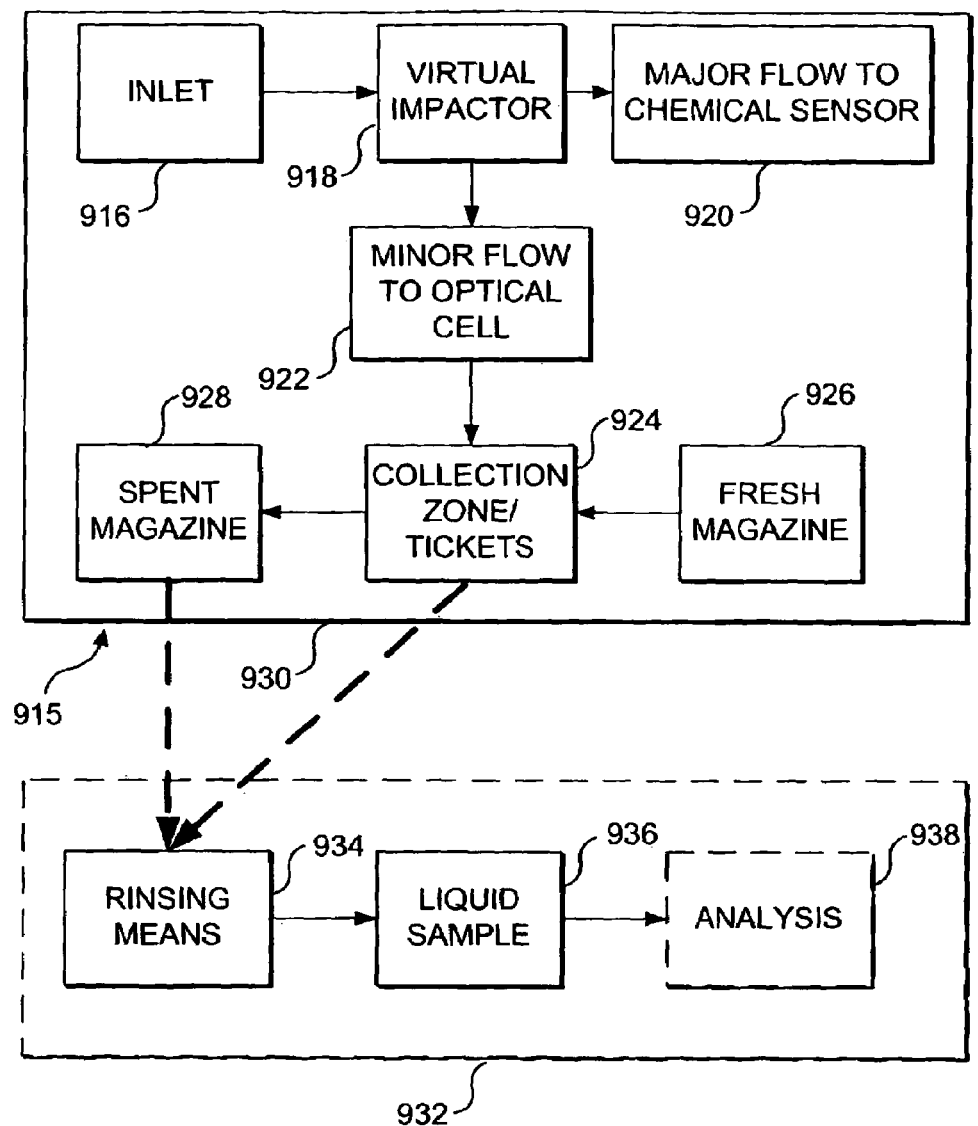
FIG. 18D is a block diagram of the components of an exemplary particle collection system utilizing the ticket of FIGS. 18A-C.

FIG. 18D illustrates a prototype system for using tickets 900. System 915 includes a fluid inlet 916 that diverts a portion of a flow of fluid into system 915. Not separately shown is a fan, which is preferably included to force fluid through system 915. As generally described above, the virtual impactors used in the present invention separate a flow of fluid into minor and major flows. A virtual impactor 918 separates the fluid into a major flow 920 that is preferably directed to a chemical sensor, and a minor flow 922 that preferably passes through an optical cell. The optical cell in the prototype employed a laser based particle counter, that triggered sample collection when the level of particles in the minor flow reached a predefined threshold. It should be understood that other parameters, such as elapsed time, could also be used to trigger a sample collection.

To collect a sample, a ticket is loaded into a collection zone 924 from a fresh magazine 926. Once the sample is collected, the ticked is moved to a spent magazine 928, and a new ticket is placed into the collection zone from fresh magazine 924. While not separately shown, it should be understood that a prime mover is employed to move the tickets from the fresh magazine to the collection zone, and then to the spent magazine. Each impact surface 908 of the tickets can incorporate any of the coatings discussed above, or no coating. Preferably each impact surface on a ticket is provided with the same coating, particularly if one impact surface will be archived. Of course, in some collections strategies, such as comparing one coating to another, different coating can be employed. Note that system 915 does not incorporate any rinsing of the sample to produce a liquid sample, but rather is intended for use in applications where the samples would be returned to a laboratory for analysis.

General Rinse System Concept

While system 915 and is quite useful for collecting dry samples for later analysis or archiving, many analytical techniques require samples in liquid forms. It would be desirable for a sample collection system to provide a liquid sample, not only to eliminate the requirement of generating such a liquid sample at the laboratory, but most importantly if analytical instrumentation requiring liquid samples is integrated into the collection system. One way to include such functionality would be to provide a rinsing module as a separate, add on module to a sampling system, as is indicated by module 932 in FIG. 18D. Such a module could interface with system 915 in a minimal way, such that when a liquid sample is required, the corresponding ticket is transferred from the either the collection zone or the spent magazine to a rinse means 934 in the rinse module. Such rinse means are described in more detail below. Such a modular system enables design improvements to be made incrementally to either the collection system or the rinse system, without affecting the other module. Another option would be to integrate the sample collection and rinsing into a single unit. Rinse means 934 will produce a liquid sample 936, which can then be taken to a laboratory, or more preferably, be analyzed in an onboard analytical unit 938.

The basic steps of the rinsing preferably include: 1) receiving a signal to rinse a collected sample; 2) removing the appropriate ticket from either the collection zone or the spent magazine; 3) delivering the appropriate ticket to the rinse module; 4) applying a rinse liquid to the ticket; 5) agitating or otherwise performing steps to facilitate removal of material from the ticket; 6) delivering the liquid sample to a sample vial; and 7) delivering the required liquid sample volume from the sample vial to the analysis system.

One variation would be to include the step of removing only the portion of the collection surface on the ticket that contains the spot of impacted particles. This will minimize the rinse volume required to remove the particles. Such minimal removal may correspond to a physical removal (or "punching out") of the impaction spot. Conversely, such minimal removal can be achieved using means (such as a sample tube that is brought in contact with, or immediately adjacent to, the surface of the ticket) that isolates the spot and minimizes the rinse area to be rinsed.

It is anticipated that a target rinse volume would result in the collection of 1 millimeter or less of fluid sample. It is also anticipated that not all samples collected in the field will need to be rinsed in the field. The rinsing will preferably be performed based on a predefined trigger event, an external input, or based on some predefined schedule. Most often, such a trigger event will cause the system to collect a liquid sample from the ticket in the collection zone. However, it would be useful to include the ability to collect a liquid sample from a previously used ticket stored in the spent magazine. Such an ability would be useful, but not required. Arrows in FIG. 18D indicate the ticket is obtained from either the collection zone or the spent magazine.

There are a number of technological features and techniques that can be utilized to improve both the efficiency of the particle impaction process as well as the efficiency of particle removal after impaction. These features include:

Use of a porous impaction surface: in traditional impactors, the surface is solid, causing the air directed towards the surface to diverge tangentially. The air retains some portion of particles, meaning that this fraction fails to impact on the surface. If the impactor surface contains very small pores, some or all of the airflow passes directly through the surface, retaining those particles that would otherwise be lost in a traditional impactor. To be effective, the pores must either be smaller than the desired particle size, or the material must contain some other means for capturing the particles as the pass by (such as an electrostatic charge).

Use of a dissolvable impaction surface: after particles are impacted, their collection can be assisted by use of a dissolvable impaction surface. Ideally, the surface is comprised of a substance that is tolerable in the resultant liquid sample, or can be easily removed from the liquid sample. An example of a tolerable substance is cellulose, which can be formed into an impaction surface and then dissolved by exposure to the enzyme cellulase. Whether any particular substance is tolerable or easily removable depends on the specific particles of interest, as well as intended methods of analysis. The surface structures illustrated in FIGS. 15A and 15B could be formed out of a soluble material. Such an impact collection surface could be fabricated into a long strip, which is moved into place for collection, then moved to the next position for rinsing (by dissolving the structures or a coating on the structures). Chitosan (which breaks down in the presence of a specific solution) and aerogels are examples of such materials, as well as the materials discussed in greater detail above.

Dissolution of surface by other methods: it is also possible to use surfaces or surface layers that lose structural integrity when exposed to other conditions, such as ultraviolet light (e.g. depolymerization), heat, acoustics, magnetic fields, electric fields, or other phenomena. For example, a collection surface could be charged to include an electrostatic field, thereby collecting particles having an opposing charge. Reversing the polarity of the applied field would repel the collected particles. Polonium or other materials can be used to apply a charge to the particles before they, impact the collection surface to facilitate such electrostatic collection/repulsion. Depending on the ambient temperatures where the system is to be used, the collection surface could be a frozen or semi-frozen impaction surface that is melted to obtain the sample. Similarly, a material having a relatively low melting point could be used either as the entire impact surface, or a coating on the impact surface. Upon the application of heat, the surface or coating would melt and flow into a sample vial, along with the sample. Such a material must be either readily removable from the sample, or must not interfere with the analysis to be employed. Filters or absorbents can be used to remove some types of unwanted material.

Use of a removable surface coating: the particles may also be efficiently rinsed if a layer on top of the surface is removable. The simplest such example is a dissolvable coating, such as a sugar layer. Another possibility is a surface coating that is held initially by a chemical bond that is later broken. One such example is a layer of streptavidin that is chemically bonded to a layer of biotin, which is covalently attached to the surface. If the rinse fluid contains excess biotin, the streptavidin will release from the surface. Many other such scenarios are possible. A viscous coating can be used, which when heated or cut with a thinner flows easily, enabling the coating to be poured into a sample container.

Continuous surface rinse: use of a continuous process that immediately removes impacted particles. One example is a liquid jet directed at the impaction region. A different example involves use of a continuous layer of water run across the impaction surface. In another embodiment, the surface itself can be rotated or translated such that newly-impacted particles become wetted and rinsed, perhaps with the aid of ultrasonics, vibration, or dissolving coatings. A number of other scenarios are possible. One preferred waterfall approach involves continually pumping fluid over a surface toward which a fluid jet is directed. In such continually rinsing embodiments, the rinse fluid can be continuously collected and re-circulated.

Use of an impaction surface with protrusions or roughness: use of surface roughness, such as impaction microstructures, will enhance the collection efficiency of particle impaction by providing an additional filtering effect. In addition, the surface features may be removable or dissolvable in order to aid in particle recovery. As noted above, FIGS. 15A and 15B are exemplary of such microstructures.

Use of a live impaction surface: use of a surface that can be deformed, flexed, twisted or vibrated to facilitate the removal of a sample. This can be done either in conjunction with a rinse fluid, or in the absence of a rinse fluid. One variation on such a live impaction surface involves a "balloon" type impaction surface, which is inflated such that the surface area of the balloon increases for sample collection, and then decreases as the balloon is deflated for rinsing. Note the deflated balloon has a smaller surface area, so that less fluid is required for rinsing, and the bond between the impacted particles and the balloon's surface is disturbed, requiring less force to remove the particles. An inflated balloon could be coated with a material that tends to flake off when the balloon is deflated. Such a material coating would preferably be relatively inflexible, such that the change in the balloon's size caused the coating to fracture. Sugar based coatings, and other materials that tend to form crystalline lattice structures (such as salts) are useful in such an application.

Use of extended collection times: the time the impact surface is exposed to the minor flow can be extended, thereby accumulating larger spots that would tend to agglomerate into particles, making them larger and stickier, and thus easier to collect.

Soaking or dipping the collection surface: use of a bath of rinse fluid that the collection surface, or a portion thereof, is repeatedly dipped into, or placed into for an extended period. This could be particularly useful if the collection surface includes a plurality of structures. Consider a plurality of elongate, "flagellating" strips whipping around in the minor flow to collect sample, which are then dissolved into or rinsed off by placing them into a fluid bath (like rinsing a mop).

Incorporating analytical reagents into collection surface: use of a test strip as the collection surface. Such test strips generally include one or more reagents, which must be exposed to a "developing" solution to complete the analysis. Instead of rinsing such a collection surface to obtain a sample, the collection surface is exposed to the developer, and the collection surface itself provides an indication (generally a color change) as to whether a suspected particulate is present.

Use of an inert rinse fluid: preferably the rinse fluid will be inert, unless a specific rinse fluid is required to dissolve a coating, or required for some other functionality described above. Jets of fluid can be used to remove the impacted particles.

Manipulate the orientation of the collection surface to the minor flow: in general, the collection surface (i.e. the impact surface) will be disposed substantially normal (i.e. perpendicular) to the direction of the minor flow. Orienting the minor flow to be parallel to a collection surface would result in the particles entrained in the minor flow settling out onto the collection surface as a function of the mass of the particles. Such a surface could be periodically rinsed, and sub portions of the surface relating to specific particle masses, or a range of particle masses, could be individually rinsed.

Use of a wiper blade: either in conjunction with the use of a rinse fluid, or alone, a blade can be used to remove collected particulates. A "windshield wiper" approach corresponds to the use of a liquid sprayed onto the collection surface and a physical blade being used to wipe off the particles.

Use of a large volume rinse: a large volume of rinse fluid can be used to remove the particles, and collected into a sample container. The large volume of fluid can be subsequently reduced (such as by evaporation), or the sample container can include binding targets, to which specific particles will bind to (such as the antibody/antigen binding discussed in conjunction with FIG. 14).

Incorporation of colormetric detection: Colormetric detection can be incorporated into many of the above scenarios, such that the presence of a target particle will be indicated by a color change. While such color changes are primarily qualitative, they provide a rapidly recognizable means to indicate which fluid samples include some level of target particles.

Combination of a movable collection surface (or minor flow nozzle) and a fluid rinse or bath: The nozzle of the minor flow could impact onto a disk shaped impact collection surface, which would slowly rotate so that the impact collection surface is dunked into a bath where soaking, vibration, dissolvable coatings or an individual one of, or a combination of the above disclosed techniques is employed to procure a liquid sample. This could be implemented as a continually rotating/rinsing embodiment or as a batch rinse approach. Instead of a disk, a strip of material could be used with a "reel to reel" type configuration where the strip is fed into a collection area, then through a rinse chamber, and then onto a "take up reel".

Note it is contemplated that some embodiments of rinsing systems will beneficially incorporate combinations of the various methods discussed above. Having now discussed rinsing in general, specific examples will be provided, along with other sample retrieval techniques (i.e. non-liquid based retrieval).

Exemplary Archival Collection System with Means for Removing and Transferring Particulates from a Collection Surface to a Container FIG. 18E illustrates an exemplary archival system 530, for collecting and archiving particulates entrained in a flow of fluid. Such particulates can include chemical and biological compounds. System 530 includes a fluid inlet 531 that diverts a portion of a flow of fluid into system 530. A fan 533, which can be centrifugal fan or an axial fan driven by a motor or other prime mover, forces fluid through system 530. It should be noted that the virtual impactors used in the present invention to separate a flow of fluid into minor and major flows function best when the fluid passes through the virtual impactor at about a predefined velocity. While a source of some fluid streams may have sufficient velocity to pass through a virtual impactor without requiring a fan to drive them through the virtual impactor, it is contemplated that many applications of system 530 (such as collecting particulates from a smokestack) will require fan 533. While as shown, fan 533 forces a fluid into system 530, those of ordinary skill in the art will recognize that the fan could alternatively be positioned to draw fluid through system 530, so that the major flow through system 530 is drawn through and exhaust 535 and the fluid comprising the minor flow (after the particulates are deposited on the archival surface), exit through another port (not shown).

System 530 also includes a virtual impactor 532 adapted to separate the fluid into a major flow and a minor flow that includes particulates of a desired size range that are directed onto an archival surface 534. Virtual impactor 532 can one of the virtual impactors described above, although it is also contemplated that other designs of virtual impactors might also be used. A fluid is forced into virtual impactor 532 by fan 533, and as described above that fluid is separated into both a major flow and a minor flow. The major flow is directed to exhaust 535, while the minor flow is directed to an archival surface 534.

Archival surface 534 can incorporate any of the coating discussed above, or no coating. The configuration of archival surface 534 can include, but is not limited to, a plate, a disk, or an elongate tape. Preferably, archival surface 534 can be readily removed and replaced with a new archival surface either when the original archival surface is full, or particulates deposited on the archival surface require analysis.

Means 546 is employed to remove particulates collected on surface 534, and to transfer those particulates to a sample container 547. Specific examples of means 546 are described in greater detail below. Means 546 is operatively coupled to a control 538, which is also discussed in greater detail below.

Preferably, archival surface 534 is coupled to a prime mover 536 that moves the archival surface relative to virtual impactor 532 over time, so that particulates collected at different times are deposited on different portions of archival surface 534. It should be noted that prime mover 536 can instead optionally move virtual impactor 532, instead of, or in addition to, moving archival surface 534.

With respect to embodiments in which prime mover 536 is drivingly coupled to archival surface 534, several different types of motion are contemplated. If archival surface 534 is a disk, prime mover 536 will likely be used to rotate the disk. If archival surface 534 is an elongate tape, then prime mover 536 will likely be used to cause one or both of a take-up wheel or a drive wheel (not shown) to be moved, to cause a corresponding movement in the elongate tape. Note that archival surface 534 is a consumable component, which when full, will be replaced with a fresh archival surface.

Prime mover 536 is controllably coupled to a control 538. The purpose of control 536 is to control the movement of prime mover 536 to achieve the desired movement of either virtual impactor 532 or archival surface 534, and to actuate means 546 when a sample of particulates is to be transferred from surface 534 to container 547. Means 546 can be actuated based on the occurrence of a predefined condition (such as a sensor indicating that a triggering event has occurred), based on an affirmative user command, or according to a predefined sampling protocol. For example, an integrated system can be designed to deposit a plurality of spots during a given time period, where some of the spots are to remain on the archival surface, and others of the spots are to be transferred to a sample container.

It is anticipated that control 538 can be one of a computing device, an application specific integrated circuit (ASIC), a hardwired logic circuit, or a simple timing circuit. In at least one embodiment, software is executed to control the operation of the device, and the control includes memory and a microprocessor. This software preferably includes a program that determines the positioning of the archival surface relative to the minor flow. The software may also include a program that controls the schedule for taking environmental samples at predetermined times, thereby producing a spot on the surface at specific spaced-apart times. In addition, the invention may execute logic that modifies the sampling schedule in accordance with algorithms that are responsive to onboard sensors 540. Finally, the software can monitor the particulate collection, generating a log of the actual time when each sample is taken in association with the disposition of the spot deposited on an archival surface at that time. This log facilitates correlating a specific sample (i.e., a specific spot) with a particular moment in time at which the spot was deposited. Control 538 is shown as being controllably coupled to fan 533. According to one sampling protocol, fan 533 will operate continuously. According to another sampling protocol, fan 533 will operate for a predefined period of time while a spot is being deposited on the archival surface, and then will be de-energized by the control. It is preferable that the flow of fluid into the system be interrupted between the deposition of samples that deposited as spots, and when the archival surface is being replaced.

Empirical tests of a prototype device, functionally similar to system 530, and employing a polymeric tape as an archival surface, has confirmed the ability of a virtual impactor to deposit spots of particulates on a movable archival surface.

As noted above, in some embodiments, system 530 may beneficially include sensors 540, which communicate with control 538 to cause a sample to be collected in response to an event that is detected by the sensors (i.e., one or more sensors). For example, an archival system may be mounted in a smokestack of a manufacturing facility, to generate an archival record of emissions from the smokestack. Such a system might be equipped with a carbon monoxide monitor, and when levels of carbon monoxide achieve a predetermined level, controller 538 (based on sensor data from sensors 540) can be programmed to initiate a sampling event, to deposit particulates on the archival surface for later analysis in response to the sensor readings. Such sensors can be used to measure relevant environmental factors that include, but are not limited to, pressure, humidity, temperature, particulate count, and presence of a particular target bio-molecule (such as particular cell types, pathogens, and toxins). Based on the detection of a specific environmental factor by such a sensor, or in accord with a sampling protocol programmed into control 538, one or more of the following functions can be executed by control 538:

generate a record of the environmental conditions at the time of spotting;

control the operation of any system components whose performance depends on a measured environmental parameters;

manipulate a programmed sampling protocol based on measured environmental factors;

actuate means 546 to transfer collected particulates to a sample container; and produce an alert signal (for example, by a radio transmission or a hard-wired signal transmission) to notify an operator of an important change in the environmental conditions (as determined by programmed control parameters).

Figure 18E:
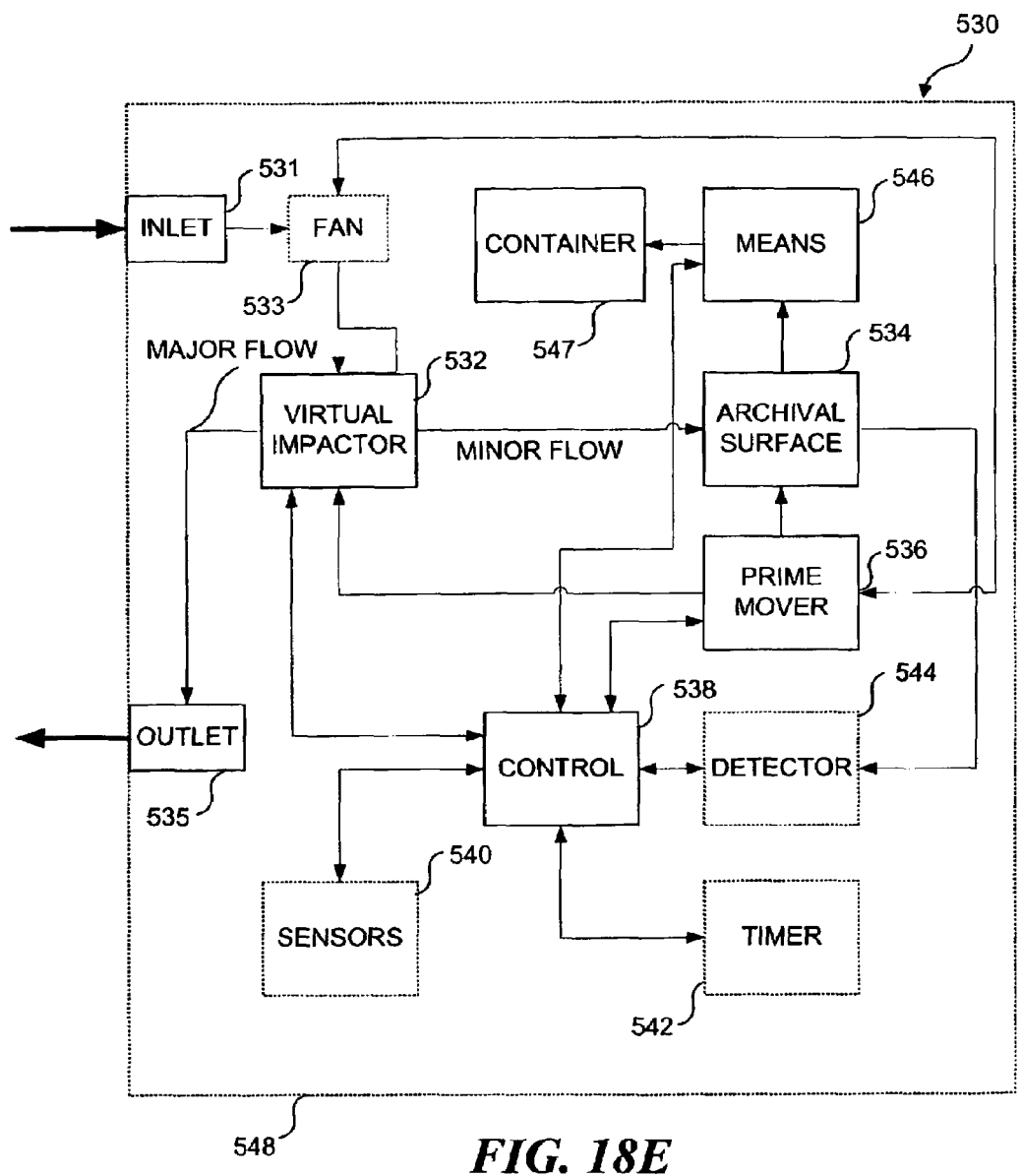
FIG. 18E is a block diagram of the components of an exemplary archival spot collection system.

Referring once again to FIG. 18E, a timer 542 is optionally included to provide a timing signal to control 538. Depending on the type of computing device (or logical circuit) employed for control 538, timer 542 may not be required. Many computing devices do not require a separate timer, and in its simplest form, control 538 may itself comprise a timer or timing integrated circuit.

One or more optional detectors 544 can be included, to analyze particulates deposited on the archival surface. It is expected however, that the archival surface will most often be removed from the system before any of the particulates (i.e. spots) are analyzed. By using a separate detector, the cost of system 530 can be reduced, as detectors are often sophisticated and expensive. Furthermore, many detection methods require particulates comprising the spots to be removed from the archival surface before being analyzed. If detector 544 requires the particulates comprising the spots to be removed from the archival surface prior to analysis, a particulate removal system (generally a liquid rinse directed at a specific spot) must also be incorporated. Particulates comprising the spots can also be removed by scraping, and other means.

Preferably system 530 will often be used in a fixed (permanent) location to monitor a specific geographical location over a long period of time. Spent archival surfaces will be removed for storage and or analysis, and new archival surfaces will be inserted in system 530. It is anticipated that system 530 can also be used as a survey instrument that is moved from one location to another, to sample different geographic regions. Such a survey instrument can be used to obtain samples (spots) from many locations within a region on a single archival surface. This feature has utility in determining the source of a particular contaminant and monitoring a number of locations when the spots on the archival surface are subsequently analyzed.

While not specifically shown, it is further contemplated that system 530 can beneficially incorporate the ability to communicate with a control system at a remote location, to send and receive control signals and other data.

In many applications, it will be important that the system be able to sample a large volume of air (>300 lpm), but it is also desirable that the sample collected be deposited in a small area (i.e., as spots 1 mm in diameter). To achieve these goals, it will be important to achieve the separation of particulates from a large air volume and their concentration in a relatively smaller air volume (i.e., the minor flow). In such applications, it is contemplated that two in-line stages of virtual impaction may be preferable. In the first stage, 90% of the inlet fluid is discarded, and the remaining 10% of the fluid (first stage minor flow) contains the desired particles. This first stage minor flow then enters a second virtual impactor stage with 90% of fluid that enters the second stage being exhausted. Therefore, the two stages have the combined effect of concentrating the outlet minor fluid volume to $\frac{1}{100}$.sup.th of the initial inlet flow volume. This relatively small minor flow should then be in the correct range for depositing the concentration of particulates as spots onto a small surface area. Preferably, the spot density on the surface will be as high as possible, without cross-sample contamination occurring, in order to minimize the required area of the archival surface.

Means for Transferring Particles from a Collection Surface to a Container

Figure 19:
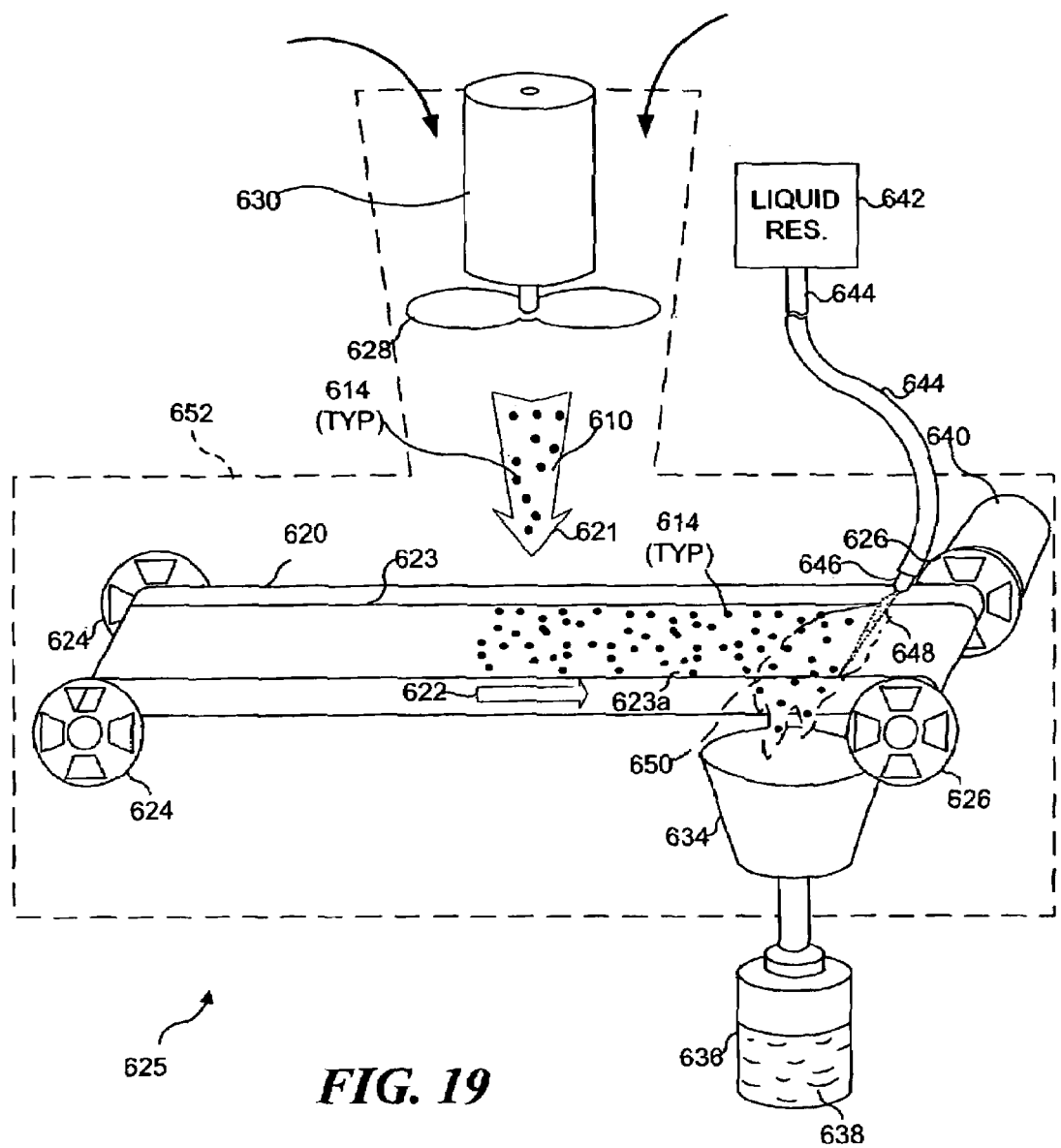
FIG. 19 is a schematic view of an integrated system using a liquid rinse to collect a sample of particles from a collection surface.

In several embodiments of the present invention, a fluid is used to remove and transfer the particulates from collection surface to a container. Depending upon the collector employed, the fluid can be a liquid or a gas. FIG. 19 schematically illustrates a particle impact collector 621 that includes tape 620' having coated impact collection surface 623. As noted above, an integrated system made in accord with the present invention can also include means for transferring collected particulates to a container. Tape 620' advances from a supply reel 624 onto a take-up reel 626. An electric motor coupled to take-up reel 626 rotates the take-up reel at a selected speed so that the tape passes under stream 621 of fluid 610. Particulates 614 impact on the coated impact collection surface of the tape and are carried toward the take-up reel by the moving tape.

Other elements of particle impact collector 621 include a fan 628, which is rotatably driven by an electric motor 630. Fan 628 impels fluid 610 in stream 621 toward coated impact collection surface 623. Other types of fans or impellers can alternatively be used. For example, a centrifugal fan (not shown) can be employed to move the fluid. If the fluid in which the particulates are entrained is a liquid, a pump (not shown) would be used instead of fan 628 to move fluid 610 toward coated impact collection surface 623.

To obtain a concentrated sample of particulates 614 from those collected on coated impact collection surface 623a, particle impact collector 621 preferably includes a specimen container 636 that is filled with a collected sample through a funnel 634. A liquid 638 that is rich in the particulates collected on the coated impact collection surface partially fills sample container 636. Liquid 638 is obtained by washing the particulates from the tape. A reservoir 642 is included to supply the liquid for this purpose. The liquid from the reservoir is conveyed through a fluid line 644 and sprayed toward tape 610 through a nozzle 646, which creates a fan-shaped spray 648 that washes the particulates from the tape. If necessary, a pump, e.g., a centrifugal or a peristaltic pump (not shown) may be used to force the liquid through nozzle 646 under sufficient pressure to wash away the particulates retained by the coated impact collection surface. These particulates are carried by a stream 650 of the liquid into funnel 634 and thus are conveyed into sample container 636. Preferably, a relatively small volume of liquid is employed, so as to avoid unnecessarily diluting the sample.

The material used for producing coated impact collection surface 623 and other coated areas or surfaces employed in other embodiments discussed herein for collecting particulates in accord with the present invention is selected because of certain characteristics of the material that increase the efficiency with which the particulates are separated from the fluid in which they are entrained, and to enhance the removal of the particulates so that they may be transferred to a sample container. Each material used for a coating has certain advantages that may make it useful for separating a specific type of particulate from a specific type of fluid. For example, for use in particle impact collector 621, the TETRAGLYME.™. material described above can be used for the coating. As noted above, this material is hydrophilic until it is exposed to water and when dry, is relatively tacky, tending to readily retain particulates that impact it, yet once water is sprayed onto the TETRAGLYME coated surface, such particulates readily released.

Figure 20A:
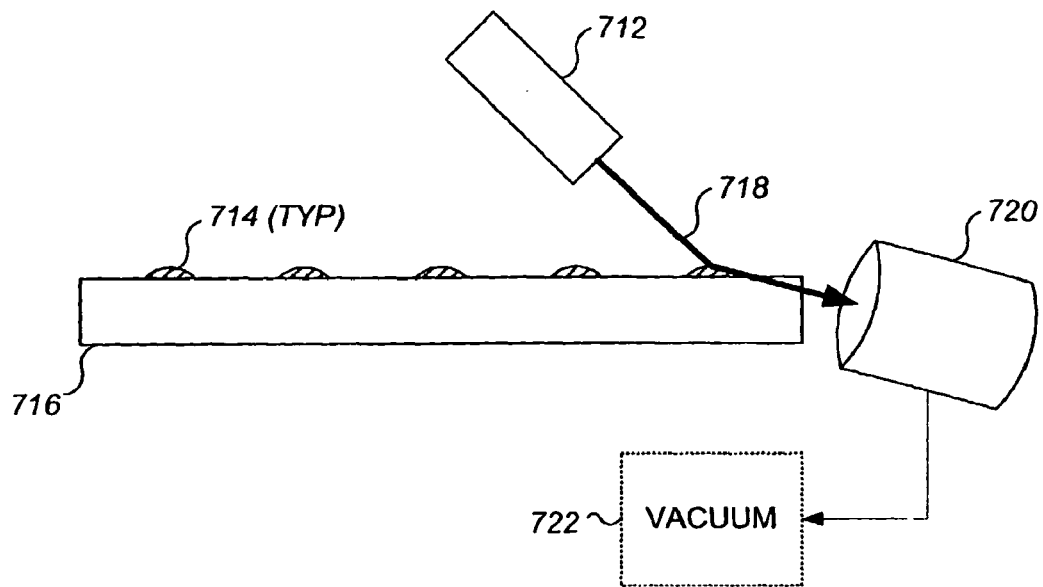
FIG. 20A is a block diagram of an embodiment in which a fluid jet is used to collect a sample of particles from a collection surface in accord with the present invention.
Figure 20B:
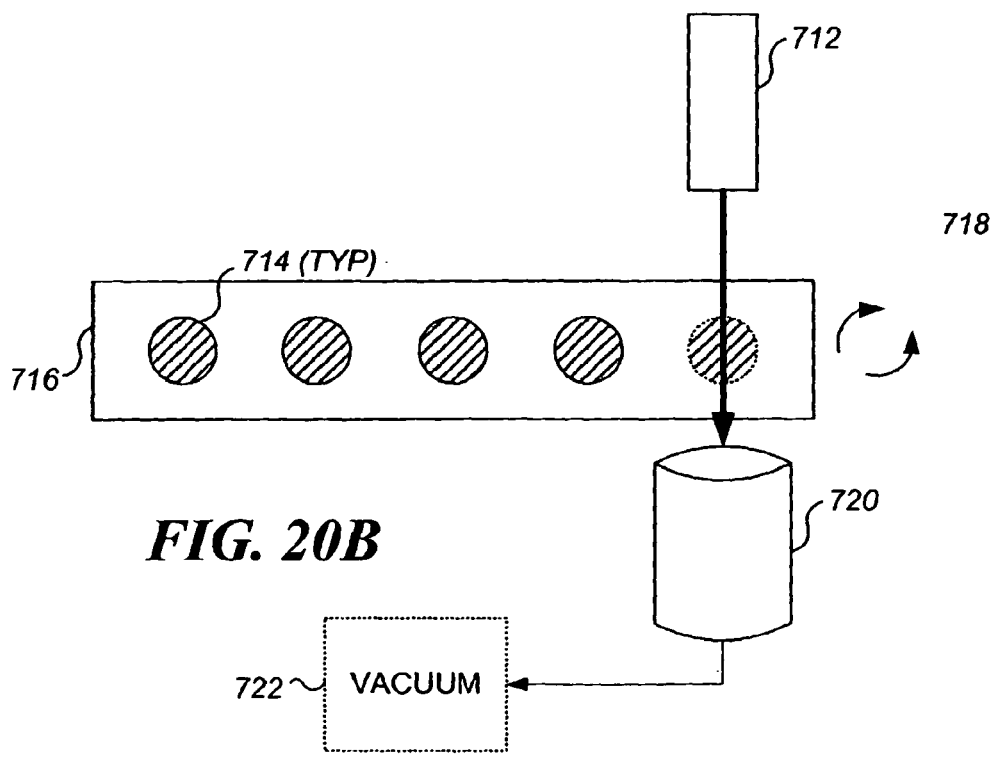
FIG. 20B is a block diagram of an embodiment in which the collection surface can be rotated 90 degrees to enable a fluid jet to be used to collect a sample of particles.

FIGS. 20A and 20B illustrate a fluid jet directed onto a collection surface, which may or may not be coated. The fluid may be a liquid (such as water) or a gas (such as air). Note that the difference between a liquid rinse and a gaseous jet is that the gaseous jet has significantly more kinetic energy than a liquid rinse. In a liquid rinse, the liquid is just acting as a carrier, picking particles up from the collection surface and rinsing them away. In contrast, use of a gaseous jet having substantially greater kinetic energy, there is a real mechanical action, where heat and friction created by the impinging high-velocity gas stream facilitate detachment of the particles from the surface. In a sense, the liquid rinse relies primarily on reduction of surface tension, and to a lesser extent, on the solvent power of the rinse liquid. The gaseous jet essentially blasts the particles off the collection surface and into a sample container.

FIG. 20A illustrates the use of a gaseous jet 718 to remove particles 714 from collection surface 716, and to transfer those particles into a sample container 720. Note that how the particles are deposited on the collection surface is not important in this Figure, since the Figure simply illustrates how such particles can be transferred to a sample container after they are collected. Source 712 of gaseous jet 718 may be directional, so that the gaseous jet is able to be directed at a particular deposit of particles on collection surface 716. It is also contemplated that source 712 can instead be fixed in position, and that instead, collection surface 716 can be moved relative to the fixed source to selectively impinge the gaseous jet on a particular group of particles.

Figure 16:
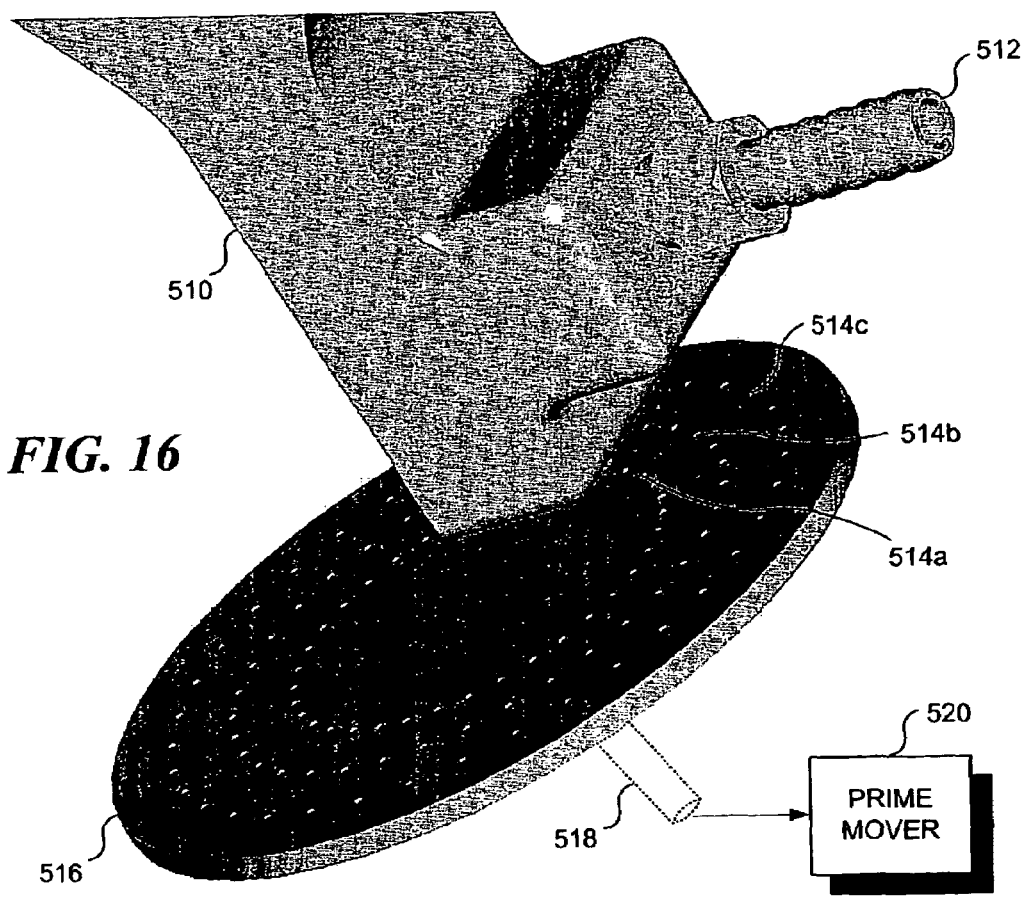
FIG. 16 is an isometric view of a virtual impactor and an archival surface in accord with the present invention.
Figure 17A:
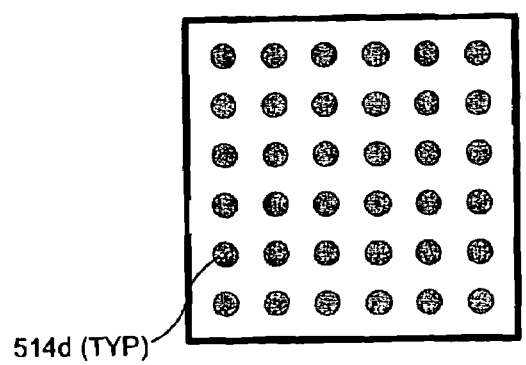
FIGS. 17A and 17B illustrate two embodiments of archival surfaces, each having a different pattern of archival spots.
Figure 17B:
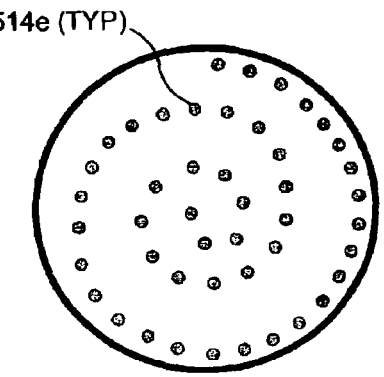

FIG. 16 and the integrated system embodiment of the present invention that are discussed above provide details indicating how a collection surface can be moved. Note that it will generally be preferable that source 712 and the inlet used for directing particles toward the collection surface for collection not be disposed in substantially the same position. However, if both the inlet and source 712 are not operated simultaneously, such a configuration should not be a problem.

The fluid jet is directed at a selected group (or spot) of particles, which are "blasted" off the collection surface and into container 720. Container 720 should be properly positioned so that substantially all of the particles blasted from the collection surface are directed into the container. If desired, container 720 can be coupled in fluid communication with a vacuum source 722, so that particles are affirmatively drawn into container 720. Such a configuration reduces the likelihood of particles being dispersed in directions other than toward the sample container. Of course, a suitable filter must be employed to prevent the particles from escaping container 720 through the line that couples the vacuum source to the container. The angle at which fluid jet 718 is directed toward the collection surface should be selected to direct the blasted particles into the collection container.

When fluid jet 718 comprises a gas, the particles are transferred into the sample container without the use of any liquid, and no dilution of the sample has taken place. A further benefit of using a gas for the jet is that container 720 can be sealed and stored dry, so that a liquid is added only immediately before analysis of the sample stored in the sample container. This approach also reduces the weight of the sample, which can be important, particularly in an integrated system embodiment in which many samples are taken, since use of dry samples can significantly reduce the total weight of the samples. The gas selected for the fluid jet should be inert with respect to the particles collected, so that no undesired reactions occur between the sample particles and the gas. Preferred gases include compressed air, compressed nitrogen, compressed carbon dioxide, and inert gases such as argon.

When fluid jet 718 comprises a liquid, care should be taken not to use too much liquid, so that the sample of particles in not unduly diluted. Because of the energetic nature of the fluid jet, even a small amount of liquid is expected to be effective in transferring the particles from the collection surface and into the sample container.

FIG. 20B illustrates an embodiment in which the collection surface can be rotated by 90 degrees, so that source 712 can be disposed above particles 714, while container 720 is disposed below the particles. Fluid jet 718 is applied to cause the particles to fall directly into container 720. Once the particles are collected, the collection surface can be rotated by 90 degrees such that collection surface 716 is properly positioned to collect particles moving in the same direction as fluid jet 718. It should also be understood that the fluid stream into which the particles are originally entrained could be directed toward an impact collection surface that is not oriented horizontally, such that particles impact on an upper portion, but vertically, such that particles impact a side surface. In such an orientation, the collection surface would not need to be rotated by 90 degrees to enable the transfer of particles into a sample container as shown in FIG. 20B to be achieved. As noted above, container 720 can be placed in fluid communication with a vacuum 722.

Figure 21A:
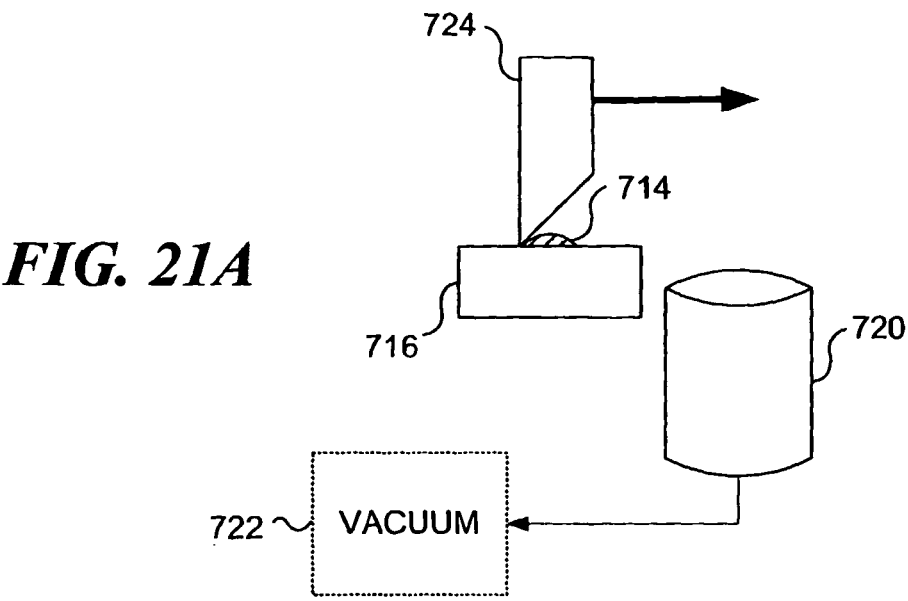
FIG. 21A is a side view of an embodiment in which a mechanical blade is used to collect a sample of particles from a collection surface in accord with the present invention.
Figure 21B:
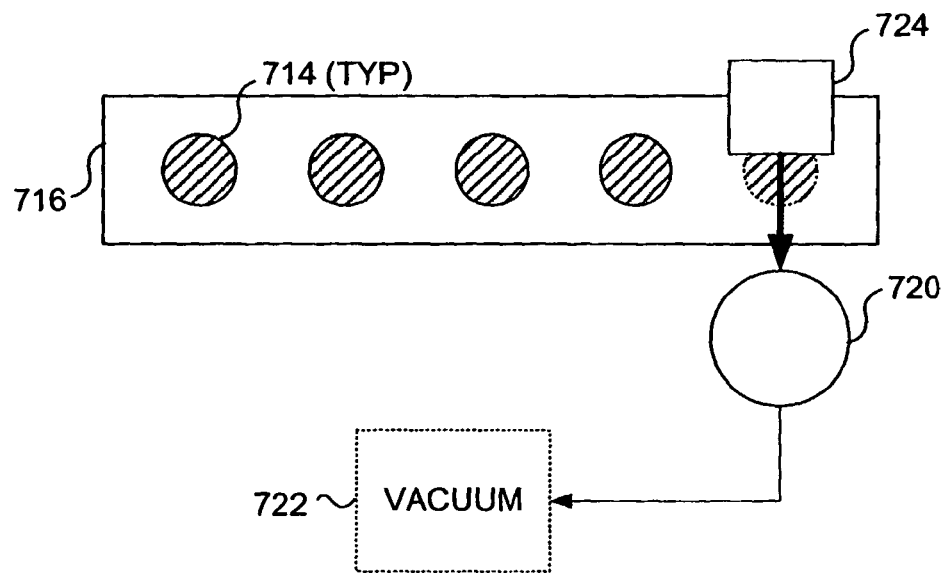
FIG. 21B is a plan view of an embodiment in which a mechanical blade is used to collect a sample of particles from a collection surface in accord with the present invention.
Figure 22:
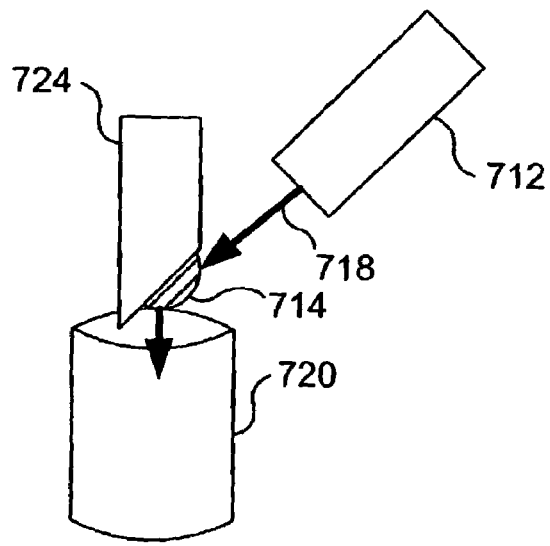
FIG. 22 is a block diagram illustrating an embodiment in which a mechanical blade is rinsed to remove particles from the blade.

A mechanical scraper 724 can be employed to remove and transfer selected particles 714 to container 720, as shown in the end view of FIG. 21A and plan view of FIG. 21B. A small volume of liquid can also be employed to rinse scraper 724, as shown in FIG. 22. As discussed above, the use of too much liquid should be avoided. Note that if scraper 724 is placed into container 720, then a gas jet can be employed to direct the particles into the container, enabling a dry sample to be collected. Particularly when container 720 is coupled in fluid communication with a vacuum, and a filter or trap is employed to prevent the particles from escaping the container, the use of a gas jet is not likely to result in dispersing the particles in undesired directions.

Figure 23:
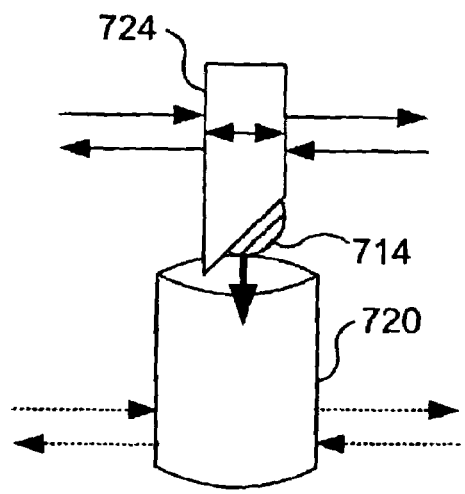
FIG. 23 is a block diagram of an embodiment in which a mechanical blade is vibrated to remove particles from the blade.

Another method of removing particles from scraper 724 without the use of a liquid rinse is to place the scraper in or immediately adjacent to container 720, and then to rapidly vibrate scraper 724, as is shown in FIG. 23. The vibrating action will tend to disperse any particles clinging to the scraper, and such particles will then fall into the container. As noted above, container 720 can be placed in fluid communication with a vacuum 722. Note that instead of, or in addition to vibrating scraper 724, the container itself can be vibrated. When container 720 contains a liquid, such vibrations will enhance the removal of particulates from the scraper.

Figure 24A:
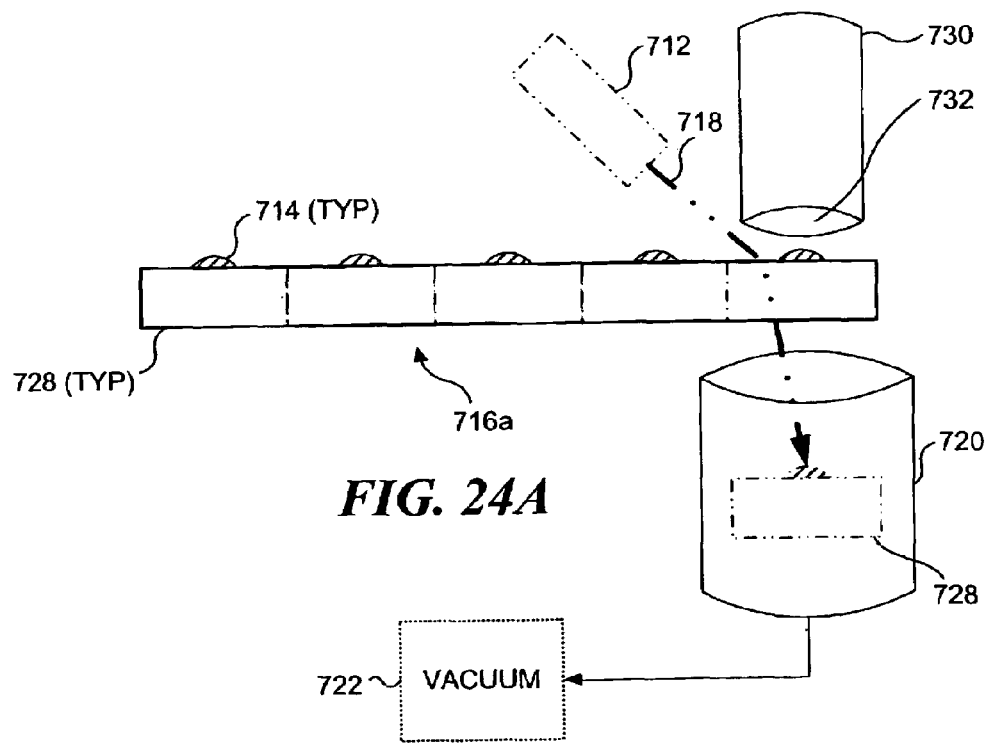
FIG. 24A is a block diagram of an embodiment in which a portion of a collection surface on which particles have been collected is removed and placed into a sample container.
Figure 24B:
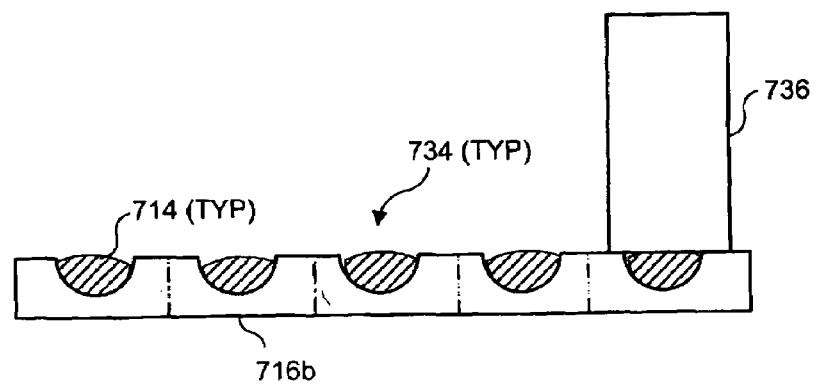
FIG. 24B is a block diagram of an embodiment in which a portion of a collection surface that includes surface features into which particles have been collected is removed and placed into a sample container.
Figure 25:
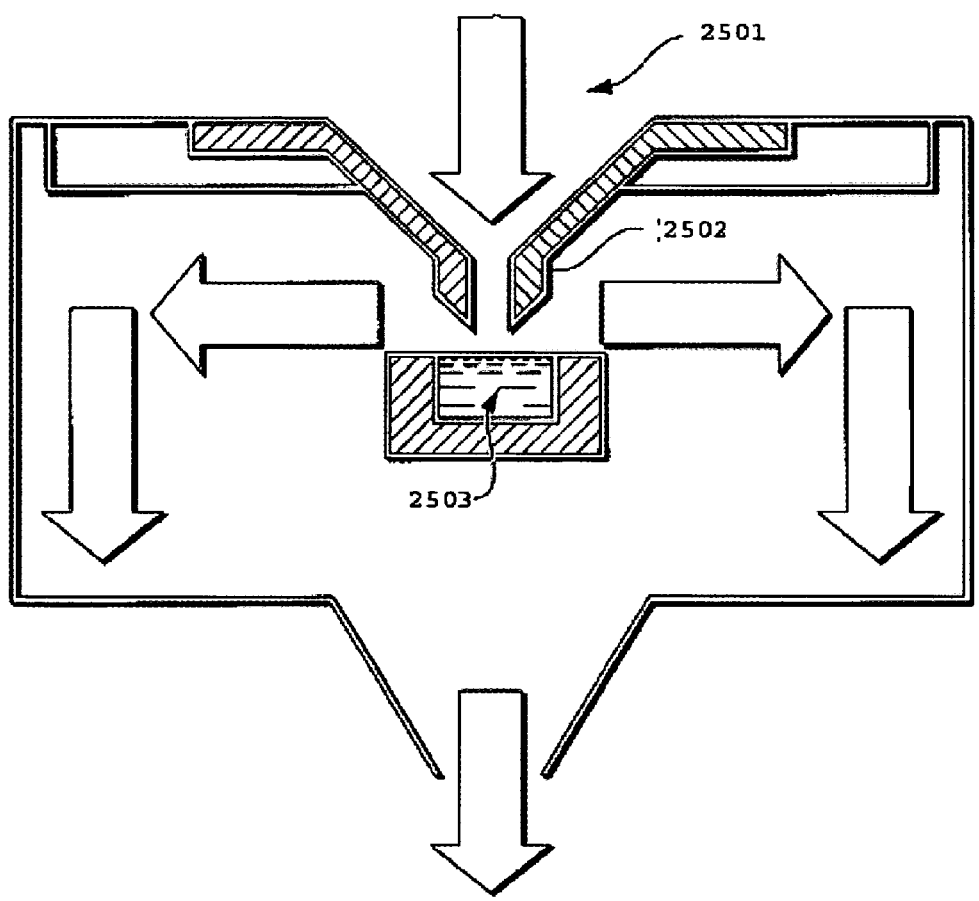
FIG. 25 is a diagram of a prior art inertial impactor.

Instead of removing the particles from the collection surface, in some embodiments, the portion of the collection surface containing a specific spot of particulates is removed and placed into a container. In a first such embodiment, shown in FIG. 24A, collection surface 716a is pre-scored into individual sections 728, enabling sections of the collection surface to be easily removed. Preferably the pre-scored sections are larger than the spot sizes, and smaller than the container. The pre-scored section is simply removed and placed in the container. No liquid is yet required, and the sample can be stored dry. Of course, the container can be filled with a desired quantity of liquid after, or even before, the portion of the surface is placed into the container. A punch 730 with a raised inner portion 732 enables the pre-scored portion to be removed without dislodging any of the particulates. In one embodiment, the punch will be disposed above the surface, and the container below the collection surface. Preferably, either the collection surface, or the container and punch can be repositioned to select a desired portion of the collection surface to remove.

If the collection surface is easily cut (such as a thin fiber or plastic material), then pre-scoring is not required. Particularly if the outer periphery of the punch is sharp, the punch will be able to remove unscored portions of such a thin collection surface. Note that the punch, or other member used to remove a portion of the collection surface, should not disturb the spot of particles on the collection surface.

Preferably the "punched" portion of the collection surface will fall into the container due to gravity. However, it may be useful for the container to be in fluid communication with a vacuum source as described above, to draw the removed portion into the container. A fluid jet 718 (preferably air) can be directed toward the cut portion of the collection surface to drive that portion into the container, however, such a jet has the potential to direct the particles in the spot in undesired directions (i.e. away from, rather than into, the container).

Note that a collection surface can be fabricated from a soluble material, such as starches or gelatin. When a portion of such a surface is placed into a container and a suitable liquid is added, the collection surface will dissolve, enabling the particles to freely disperse within the sample container. This can be quite beneficial, particularly in cases in which the presence of a portion of a collection surface in a liquid sample is not compatible with a particular analytical method.

It is anticipated that combinations of the above techniques can be useful. For example, a collection surface can be coated with a dissolvable coating, so that when a liquid jet is directed at that portion of the collection surface (see FIGS. 20A and 20B), the coating is dissolved and particles are readily removed. Another variation is to use a pre-scored collection surface coated with a dissolvable coating. After the pre-scored portion is placed in a container, and a liquid has been added to the container to dissolve the coating, the remaining portion of the collection surface can then be removed from the container.

Yet another variation, shown in FIG. 24B, is to employ a pre-scored collection surface **716*b* with a plurality of surface indentations 734. The particles are directed into the indentations, and then a normal punch 736** can be employed to remove the scored portions without disturbing the particles disposed in the indentation.

Preferable containers are plastic, although glass, metal, and ceramic can alternatively be employed. As with any sample container used to collect a sample for analysis, containers should be inert and clean, so that contaminants are not introduced into the sample.

In one aspect, the invention relates to an apparatus or device for continuous monitoring of the concentration and content of airborne particles. One embodiment is diagramed in FIG. 2. Some components of the device are a spotting nozzle, an impaction plate, a detector, and a regenerator. Additional components are present in some embodiments, such as a virtual impactor and/or a liquid coating applicator.

The spotting nozzle accelerates air from an inlet onto the impaction plate where airborne particles are collected. By spotting nozzle is meant a jet through which a gas sample is passed and which increases the mean velocity of the gas sample to a value sufficient to impart enough momentum to particles above a specific size that the particles are able to impact on an impaction plate as described herein. For example, a gas sample may be sucked through a nozzle having a reduced cross-sectional area relative to a source of gas using a downstream vacuum pump. An acceleration nozzle may be of any shape, such as round or slit-shaped. A round acceleration nozzle or jet has a round opening through which gas exits. The nozzle body may be cylindrical. A slit-shaped acceleration nozzle or jet has a rectangular opening, including narrow and nearly square-shaped openings, through which gas exits.

Acceptable spotting nozzles have been used in inertial impactors. An exemplary inertial impactor is shown in FIG. 25. Accordingly, an air sample (2501) is drawn through the inlet (2502). The sample of air is drawn over the surface of the substrate (2503), which collects particles having an inertia too great to follow the curved path of the air stream. The substrate, or impaction plate, according to the present invention is described below.

An inertial impactor typically refers to a single unit comprising of an air inlet, a spotting or acceleration nozzle, and an impaction plate. At the acceleration nozzle exit, the airstreams turns sharply and particles larger than a certain diameter (referred to as the impactor's cut-off size) impinge on the collection surface of the impaction plate due to inertial forces. Exemplary inertial impactors are discussed in U.S. Pat. Nos. 6,435,043, 5,553,795, 5,437,198, 4,926,679, 4,796,475, 4,321,822, and 4,133,202.

The physical principles of operation of an inertial impactor is similar to that of a virtual impactor referred to below. A jet of particle-laden air is deflected abruptly by an impaction plate, which causes an abrupt deflection of the air streamlines. Particles larger than a critical size (the so-called cutpoint of the impactor) cross the air streamlines and are collected on the impaction plate, while particles smaller than the critical size follow the deflected streamlines. The cutpoint of an impactor is determined by several parameters through the Stokes number.

$$St = \frac{\rho_p d_p^2 U C_c}{9\eta D_j}$$

where $\rho_p$ is the particle density, $d_p$ is the particle diameter, U is the impactor jet velocity, $\eta$ is the gas viscosity, and $D_j$ is the diameter of the impactor jet (Hinds, "Aerosol Technology", 1982, John Wiley & Sons, Inc.). The slip correction factor, $C_c$, corrects for the reduced drag on small particles as they approach the mean free path of the gas. The collection efficiency for an impactor is often characterized by its D50, the diameter at which 50% of the input particles are collected.

The slip correction factor is given by the following equation:

$$C_c = 1 + \frac{2}{Pd_p}(6.32 + 2.01^{-0.1095 Pd_p})$$

where P is the absolute pressure in Cm Hg and $d_p$ is the particle diameter in μm.

The preferred air velocity is greater than 10 m/s and less than 100 m/s, and more preferably greater than 20 m/s and less than 30 m/s. The nozzle diameter is preferably greater than 0.25 mm and less than 2.5 mm, and more preferably greater than 0.5 mm and less than 1 mm. The nozzle is preferably located a distance from the impaction surface greater than 0.1 mm and less than 2 mm, and more preferably, a distance greater than 0.25 mm and less than 0.5 mm.

Inertial impactors and impaction substrates used for collection of ambient particles are known to sometimes exhibit low particle collection efficiency. Low particle collection efficiency is a result of at least two factors: particles of high momentum impact the substrate and bounce off, and particles which have been previously collected are displaced from the substrate and re-entrained in the airstream (Sehmel, G. A., Environ. Intern., 4, 107-127 (1980); Wall, S., John, W., Wang, H. C. and Coren, S. L., Areosl. Sci. Technol., 12, 926-946 (1990); John, W., Fritter, D. N. and Winklmayr, W., J. Aerosol. Sci., 22, 723-736 (1991); John, W. and Sethi, V., Aerosol Sci. Technol., 19, 57-68 (1993)). In addition, because these two processes typically depend on particle size, the size distribution of the collected particles can be distorted.

Such problems, however, are not of significant concern for the invented devices. Precise knowledge of collection efficiency is not crucial for the present invention. The only requirement for the collection efficiency is that it does not vary widely or unpredictably with the concentration of airborne particles. Thus, under otherwise similar operating conditions, a larger number of particles should be collected into a spot from an air sample with a higher concentration of airborne particles. A spot is an aggregate of particulates deposited upon a surface in a relatively small area, so that the individually small particulates are aggregated together to form a larger spot. Moreover, as described below, the present invention provides for continuous monitoring of air samples. As a result, it is often detection of changes in the concentration and/or composition of airborne particles in air samples that is of interest. Detection of such changes is unaffected by a relatively low collection efficiency. Thus, the continuous monitoring feature of the present invention circumvents some of the shortcomings usually associated with inertial impactors.

For the same reason, variability of collection efficiency for particle of various sizes does not negatively impact the operation of the present invention. In a preferred embodiment, the inertial impactor is configured for optimum collection of particles in the 0.5-10 μm diameter, more preferably in the 1-5 μm range. Airborne particles in this range are the most likely to represent an inhalation hazards to humans. Within this range bacteria would be captured, as well as potentially noxious viruses or protein aggregates. However, the inertial impactor may be configured for optimal collection of particles of other size ranges in different applications.

In some embodiments, the intake of the spotting nozzle is downstream of a virtual impactor. By downstream it is mean that the second component (the spotting nozzle in this case) and the first component (the virtual impactor) are arranged so that the gas or air sample passes sequentially through the first and then the second component of the system. A virtual impactor is an apparatus that increases the concentration of airborne particles of a desirable size range. It separates an airflow into a minor and a major component, wherein the minor component carries a majority of airborne particles above a certain size. Examples of virtual impactors can be found in U.S. patent application Ser. No. 09/955,481, or in U.S. Pat. Nos. 3,901,798; 4,670,135; 4,767,524; 5,425,802; and 5,533,406. Thus, the spotting nozzle can be downstream of the minor flow of a virtual impactor. It is preferable that the virtual impactor increases the concentration of particles above 1 μm. In some embodiments, more than one virtual impactor is placed upstream of the spotting nozzle. Impacting air with higher concentration of airborne particles in the desired range increases the collection pace and thus the efficiency or sensitivity of the invented device.

Additionally, some embodiments contain a size selective inlet for preconditioning the air sample by removing particles above a desirable size. A "size-selective inlet" removes particles above a certain size (aerodynamic diameter) from a stream or sample of gas. By "remove" is meant that at a predetermined particle size, 50% of the particles are removed from the gas sample and 50% pass through the size selective inlet. For particles of smaller sizes than the predetermined size, most, or almost all, particles pass through the inlet, while for particles of larger sizes, most, or almost all, particles are removed. The substrate of a size-selective inlet collects the removed particles. In certain preferred embodiments a size selective inlet comprises an inertial impactor. The size of the particles removed is determined, in part, by the velocity of the gas sample as it comes out of the acceleration nozzle. The higher the velocity, the smaller the size of the particles removed. Thus, by selecting the appropriate acceleration nozzle, a predetermined upper size of particles can be removed from a gas sample. In certain embodiments, a size-selective inlet comprises a filter, an elutriator, or any other device capable of removing particles greater than a predetermined size. Preferably, the size selective inlet removes particles above 10 μm, but may be set to remove particles above other sizes, for example 12 μm, 15 μm, 20 μm, or 25 μm. In those embodiments where a virtual impactor is present, the size selective inlet may be placed either upstream or downstream of the virtual impactor. Removal of large airborne particles eliminates potential sources of interference with the analyzer discussed below.

The spotting nozzle directs the air stream towards a collection surface of an impaction plate, thus depositing airborne particles on the collection surface of the impaction plate. The collection surface according to the present invention can be regenerated. Regeneration occurs by the action of a surface regenerator as described below. Regeneration of the collection surface enables continuous and automatic reuse of the device. Thus, unlike other inertial impactors, the present invention does not require a consumable impaction plate.

The impaction plate may take a variety of shapes, but the collection surface is typically flat. In some embodiments, the impaction plate is a disk, i.e. flat, thin, and circular. A disk axis is perpendicularly on the center of the two parallel circular surfaces of the disk. In these embodiments, the collection surface is on one of the two planar parallel surfaces of the disk, preferably at some distance from the center of the disk axis. In other embodiments the impaction plate is a lobed cam. One or several substantially planar surfaces are parallel to the cam axis and function as collection surfaces. A cam shaft along the cam axis is part of the homing sensor as described below.

The impaction plate is preferably made substantially of a homogenous material, although it is possible to embed a collection surface of one material on an impaction plate made of a different material. The plate, or at least its collection surface, is made of a material sufficiently durable to withstand repeated action of the surface regenerator without incurring any damage. Many materials are suitable, including glass, quartz, ceramic, silicon wafers metal or plastic. In addition, coatings can be deposited on one of the above materials to increase the hardness and/or resistance to abrasion. In a preferred embodiment the plate is made entirely of UV transparent material, for example fused silica pure silica, or sapphire (Edmond Scientific).

In a preferred embodiment the collection surface is essentially smooth. A smooth surface is preferred as it is easiest to clean by the surface regenerator. On the other hand, particles tend to bounce off smooth surfaces easier, thus decreasing collection efficiency. Consequently, in other embodiments, the collection surface has outwardly projecting structures, such as rods (FIG. 15A) or ribs (FIG. 15B). For example, the surface is micromachined to have pyramid-shaped structures of approximately 1-10 μm in height and width. In these embodiments, particle loss is minimized, but relatively harsher surface regenerators are used.

One function of the impaction plate is to support the collection surface for the accumulation of the sample of airborne particles during impaction. Accordingly, at one point in the cycle of operation of the device, the collection surface is under the spotting nozzle. Typically, the collection surface is horizontal while the spotting nozzle is vertical.

In a preferred embodiment, the impaction plate also functions as part of the homing sensor, as discussed below. The spot on the collection surface is subject to analysis by the analyzer, and the collection surface is regenerated by the surface regenerator (i.e. the surface regenerator cleans the spot from the collection surface).

For example, the impaction plate may less than 150 mm in diameter, and more preferably less than 80 mm in diameter but greater than 20 mm in diamter. The collection surface is preferably less than 25 mm in diameter, and more preferably less than 15 mm but greater than 5 mm in diameter.

Another component of the invented devices is an analyzer for charactering the content of the spot. Analyzers may take a wide variety of forms, depending on the type of airborne particles to be monitored in different applications. For example, analyzers may detect biological particles, specific chemical compounds, or radioactive particles. Detection may be achieved by any one or combination of available techniques, such as mass spectrometry, infrared spectroscopy, fluorescence measurements, or Raman spectroscopy, gamma emission, alpha particle emission, or beta emissions. Monitoring of biological particles is described in some detail below. Useful chemical monitoring may be, for example, of nonvolatile toxic chemicals such as VX chemical warfare agent or mercury containing particulate emitted from coal-fired power plants.

In some embodiments, the invented devices comprise a pre-analysis spot preparation station. At this point the spot is prepared to enhance its characteristics measured by the analyzer. The spot may be combined with compounds that affect measured properties of the airborne particles of interest by squirting a liquid containing the appropriate compound from an inkjet type of device. For example, the liquid may contain matrix solution used in a Matrix Assisted Laser Desorption Ionization (MALDI) mass spectrometer, or a DNA stain that becomes fluorescent when it is bound with DNA, such as ethidium bromide.

It is preferable that any amount of consumable reagents be kept at a minimum to ensure prolonged maintenance free operation of the devices. In one embodiment, the pre-analysis spot preparation station applies a plasma lysis pulse to the spot to expose the contents of any microbes (see for example U.S. Pat. No. 5,989,824)

Another component of the invented devices is a surface regenerator. The purpose of the surface regenerator is to regenerate the surface, i.e. to remove the deposit from the collection surface after analysis, and thus to make the collection surface available for collecting another spot. The surface regenerator must remove substantially all the spot from the collection surface, so prior use of the collection surface does not interfere with analysis of subsequently gathered spots.

In some embodiments, especially where a smooth collection surface is used, a surface regenerator may be felt or cloth pad that is pressed against a moving collection surface as it slides towards the nozzle. By "felt" is meant a porous fibrous structure, typically unwoven, created by interlocking fibers using heat, moisture or pressure. Suitable fibers include, but are not limited to, polyester, polyurethane, polypropylene, and other synthetic and natural fibers. By "cloth" is meant material that is made by weaving, felting, knitting, knotting, or bonding natural or synthetic fibers or filaments. Of course, movement of a pad relative to the collection surface while pressed on it may be achieved by many other known means. Alternatively, a felt or cloth wheel may be used, and a motor spins the wheel when it is in contact with the spot, thus regenerating the collection surface. In other embodiments, the surface regenerator is a brush or blade that remove the spot, for example with a sweeping motion. When the collection surface is not smooth, one or more brushes are desirable, and their sweeping motion may be performed in multiple directions. In yet other embodiments, surface regeneration is achieved by blowing a stream of air at an angle at the spot, i.e. the surface regenerator comprises a nozzle oriented an angle towards the collection surface, which blows a stream of air at high velocity towards the collection surface. In some embodiments, regeneration is aided by electrostatically charging the spot either before or during the action of any regenerator. The collection surface may be temporarily imparted a positive charge, a negative charge, or alternative positive and negative charges. In some embodiments, the regenerator comprises at least in part heaters or lasers capable of transferring energy to the surface spot/collection surface. In some embodiments, multiple regenerators are present and they are either used sequentially in each cycle of the device, or some of them are activated only when necessary, for example in periodic "deep cleaning" cycles, or in response to sensing incomplete regeneration of the collection surface.

In some embodiments, another component of the invented devices is a liquid coating applicator. The function of the liquid coating applicator is to spread a droplet of liquid over the collection surface or a portion thereof before impaction of the air sample. The amount of liquid is typically minuscule, and so essentially all of the applied liquid evaporates during the subsequent air impaction with the collection surface. The purpose of the liquid is to reduce particle bounce from the collection surface, at least at the initial stages of gathering the spot. Thus, a spot nucleus forms which reduces particle bounce during the remaining time of acquisition of the spot and improving collection efficiency. In these embodiments, a consumable (the liquid) is necessary, but it is used up in minute amounts. A relatively small liquid reservoir thus can contain and make available liquid for a very large number of cycles. For example, a 500 ml reservoir might suffice for 10,000 cycles. Accordingly, replenishing the consumable is required quite rarely.

Any liquid capable of trapping impacting particles may be used, such as water, alcohols such as ethanol or methanol, glycerol, a mineral oil, or medium weight hydrocarbons such as octane. It is important that the liquid does not affect the collected spot so as to interfere with its subsequent analysis.

The amount of liquid necessary may vary with the nature of the liquid and other features and dimensions of the device. Usually, the volume of liquid for each application is from 0.5 μl to 50 μl, and may be, for example, 0.5, 1, 2, 3, 4, 5, 6, 7, 8, 9, 10, 15, 20, 25, 30, 35, 40, 45, or 50 μl. It is preferred that an identical volume of liquid is applied in each cycle of operation.

Any device capable of spreading a liquid droplet on a surface may be used as an applicator in the present invention. In a preferred embodiment, the applicator is a felt tip pen.

Another component of the invented devices is a homing sensor. The function of the homing sensor is to move the collection surface between the spotting nozzle, the analyzer, the regenerator, and, in some embodiments, the liquid coating applicator. Thus, each component of the invented device can perform their respective function on the collection surface.

The homing sensor is a mechanical device that alters the position of the collection surface with respect to the other components. Thus, the homing sensor is not a sensor in the usual meaning of the term, although in some embodiments one or more sensors may be present and capable to detect and communicate the position of the collection surface within the functional cycle. Many types of mechanisms can be used as homing sensors. In one embodiment, the spotting nozzle, analyzer, regenerator, and liquid coating applicator if present, have fixed positions. The collection surface is on a face of a disk. On the opposite face a shaft is attached down the axis of the disk, the shaft being coupled to a prime mover. The disk can thus be rotated at predetermined angles to position the collection surface sequentially for each component. In another embodiment, the impaction plate is a lobed cam having a shaft. There is at least one planar collection surface essentially parallel to the shaft. In these embodiments, the homing sensor comprises the impaction plate, shaft and prime mover. Those of skill in the art will recognize that other mechanical structures can accomplish the function of the homing sensor. Thus, the collection surface may be moved substantially linearly, or the collection surface may be retained in a fixed location while other components are repositioned with respect to the collection surface. Accordingly, any known means of translocationg the collection surface relative to other components may be used.

In operation, an air stream is pulled through the air inlet of the spotting nozzle. The air stream is a sample of environmental air. The sample is pre-concentrated in some embodiments by the action of a virtual impactor upstream of the air inlet of the spotting nozzle, so that the air stream is enriched in particles of the 1-10 μm range. The air sample is also preconditioned in some embodiments by the action of a size selective inlet upstream of the spotting nozzle to eliminate particles above a desired size, such as 10 μm, to improve the desired air composition.

The air stream emerging from the spotting nozzle impacts on the collection surface of the impaction plate. As a result, a spot forms that consists mainly of particles in the desired size range, which is preferably of an aerodynamic diameter of 1-10 μm. The collection efficiency of the collection surface may be low as long as it is roughly consistent for different particle concentrations. By collection efficiency is meant the proportion of particles in the desired size range in the air sample that is trapped on the collection surface as a result of impaction.

In some embodiments, prior to impaction of the air stream by the spotting nozzle, the collection surface of the impaction plate is coated with a liquid by the action of a liquid coating applicator. The liquid coating improves the collection efficiency of the collection surface.

The position of the collection surface relative to other components of the invented devices changes through the action of a homing sensor. Thus, the homing sensor automatically positions the collection surface sequentially from the liquid coating applicator, if one is present, to the spotting nozzle, to the analyzer, and to the regenerator or regenerators. In some embodiments, the homing sensor may be able to vary the order of repositioning the collection surface in certain circumstances. For example, the homing sensor could be able to move the collection surface from the regenerator to the analyzer if or when it is desirable to ensure proper regeneration of the collection surface.

After a spot accumulates on the collection surface by the action of the spotting nozzle, movement of air through the spotting nozzle usually ceases and the collection surface with the spot moves to the analyzer. In some embodiments, a first step at this stage is preparing the sample for analysis at the pre-analysis spot preparation station. The analyzer then detects the presence and/or measures the concentration specific airborne particles or constituents thereof.

Following analysis, the collection surface is moved by the homing sensor to the surface regenerator, which acts to clean the collection surface and thus regenerate it for another cycle of operation. The regenerator may act by one or several mechanisms to regenerate the collection surface. Thus, the regenerator could act by a mechanical brushing or wiping of the surface, by blowing an air stream at high velocity towards the spot, preferably at an angle, and/or by electrostatically charging the spot. Following the action of the regenerator, the collection surface is used again in another cycle of collection, analysis, and regeneration. The number of cycles that a device can perform automatically without any need for service is very large, preferably in the thousands.

In another aspect, the present invention relates to methods for continuously monitoring airborne particles (see FIG. 27). The airborne particles being monitored are preferably biological particles, although specific chemicals or radioisotopes may also be monitored, and monitoring implies detection of their presence, their concentration and/or possibly their nature. Continuous detection refers to repeated sampling of environmental air. By continuous it is not meant that necessarily air samples are uninterruptedly being evaluated, but rather air samples may be evaluated at repeated time intervals. Thus, detection of airborne particles occurs in cycles that comprise at least some identical steps. The main steps of each cycle are immobilizing airborne particles on a collection surface, analyzing the immobilized airborne particles, and regenerating the collection surface. Additional steps are performed in some embodiments.

A step according to the present methods is depositing airborne particles on a collection surface (2740). At this step, airborne particles are extracted from ambient air. Any known extraction methods may be used if it results in depositing airborne particles on a collection surface. In a preferred embodiment, however, depositing airborne particles is achieved by inertial impaction.

As a result of depositing airborne particles, a spot forms on the collection surface. The spot contains extracted or immobilized airborne particles from the ambient air sample. However, not every particle in the original ambient air sample needs to be deposited on the collection surface at this step. It is envisioned that particles of a desirable size range may be enriched in the spot. In fact, in some embodiments particles of undesirable size ranges may be actively excluded. The precise size range differs as required by specific applications. In preferred embodiments, particles of 1-10 μm comprise the desirable size range. Particles in this size range may be inhaled and may include dangerous biologicals.

In some embodiments, airborne particles of a desirable size range are concentrated in a step preceding depositing airborne particles on the collection surface (2720). Concentration may be achieved, for example, by the action of a virtual impactor. This concentration of particles allows quick sampling of large volumes of air, which decreases the time required for performing each cycle of the invented methods, and therefore improves the performance and ultimately the safety of the air.

In some embodiments the sampled air is preconditioned prior to depositing airborne particles on the collection surface (2710). By preconditioned it is meant that particles greater than a desirable size are removed from the sample. This may be accomplished with a size selective inlet as discussed above. Particles greater than the desired size range may be first removed from the air, and thus such particles do not end up in the spot. Consequently, they cannot interfere with the analysis of the spot described below. Preconditioning may remove, for example, particles greater than 10 μm, but may remove only particles greater than other sizes, for example 5 μm, 7 μm, 8 μm, 12 μm, 15 μm, 20 μm, or 25 μm. In some embodiments, both preconditioning and concentration are performed prior to depositing particles on the surface.

In some embodiments, another step that may be performed prior to depositing airborne particles is moistening the collection surface (2730). Many types of liquids may be used to moisten the collection surface including glycerol, alcohols, or medium weight hydrocarbons, such as octane, as mentioned above in describing the liquid coating applicator. The precise volume of liquid used in each cycle depends on several different variables, and may be about 0.5, 1, 2, 3, 4, 5, 6, 7, 8, 9, 10, 15, 20, 25, 30, 35, 40, 45, or 50 μl.

Another step of the invented methods comprises analysis of the spot (2750). The type of analysis performed depends on the nature of the particles to be monitored. Appropriate analyses of spots for biological materials are described in some detail below. Chemical, radiological, or any other type of analysis may be performed according to any known suitable test. In some embodiments, analyzing comprises an optional step of pre-treating the spot so as to enhance the measured signal. Thus, pre-treating may comprise adding to the spot a liquid comprising an analysis-enhancing compound. In some embodiments where analyzing is accomplished by MALDI mass spectrometry, pre-treating may be performed by plasma lysing.

Another step of the invented methods comprises regenerating the collection surface (2760). The precise nature of the physical act that accomplishes regeneration depends on many variables such as the application that employs the methods, the expected average air characteristics, or the type of collection surface used. Regeneration may be achieved by any one or combination of steps. For example, in some embodiments, regeneration is accomplished by pressing a felt pad against the collection surface and moving the felt pad over the collection surface. In other embodiments a felt wheel is rotated while pressed against the collection surface. In other embodiments the collection surface is electrostatically charged as part of the regeneration step. In other embodiments regeneration is accomplished by brushing the collection surface with a brush. In other embodiments regeneration is accomplished by blowing an air jet at high velocity towards the collection surface. In other embodiments, regeneration is accomplished by scraping or wiping the collection surface with a blade. Regenerating the surface may be achieved by one or more acts. When more than one act is used, the acts may be similar or identical, or they may be different. In some embodiments, specific regeneration acts are not necessarily performed in each cycle.

In some embodiments all the cycles of the invented methods are identical. In other embodiments, some cycles may comprise different steps from other cycles.

In some embodiments, the invented methods in at least a subset of cycles comprise verifying the regeneration of the surface (2770). Accordingly, the collection surface is analyzed again after regeneration. This analysis may be performed essentially by the same process or test that was used for analyzing the spot. Thus a background signal level is obtained for the regenerated surface. The background signal level is then compared to predetermined criteria. If the background level is found to be higher than desirable, regeneration and verification is repeated until the background signal level meets predetermined criteria. Alternatively, a test may be employed in assessing if regeneration was acceptably accomplished that is different from the sample analysis test.

Each cycle of the invented methods may be considered to start with depositing airborne particles on the collection surface to form the spot (2740). In those embodiments that comprise preconditioning (2710) and/or concentrating (2720) the air sample from which particles are extracted, the additional step(s) can occur essentially simultaneously with the step of depositing particles on the surface. In those embodiments where the methods comprise moistening the collection surface (2730), this step may be seen as the first step of each cycle. Of course, given the cyclical nature of the invented methods, the selection of any step as the first is arbitrary.

After completion of the depositing step, each cycle comprises the step of analyzing the spot present on the collection surface (2750). During analysis, data regarding properties of the sample is gathered and transmitted. This way, the methods are useful in acquiring and conveying information about the presence and quantity of airborne particles of interest such as biological particles.

After analysis the next step is regenerating the collection surface (2760). The surface is regenerated by any one or more feasible means. In some embodiments, proper regeneration is verified in at least a subset of cycles (2770). Thus, the collection surface may be re-analyzed.

After regeneration, the next cycle proceeds with depositing airborne particles from another air sample, which is preceded in some embodiments by moistening the collection surface.

In another aspect, the present invention relates generally to devices useful for monitoring airborne biological particles. The devices can analyze the content of extracted particles deposited as a spot on a collection surface, preferably a regenerative. By regenerative collection surface it is meant a collection surface on which a spot of airborne particles can be deposited or immobilized for a period of time, and then the spot can be removed thus regenerating or refreshing the surface. The regenerated collection surface has similar characteristics to the collection surface prior to the previous spot immobilization. The surface refreshing need not necessarily achieve virtually identical characteristics. Rather, the surface must be sufficiently regenerated that the next signal resulting from any residue will be insignificant relative to the signal resulting by the sample spot. Thus, the regenerative collection surface can be used in numerous similar cycles of spot immobilization and regeneration. Regenerative collection surfaces are described in more detail above.

The devices also comprise in some embodiments the means of extracting particles from ambient air and depositing or immobilizing them on the surface, such as an inertial impactor. Thus, the airborne particles are immobilized on a collection surface as a spot.

The invented devices comprise a detector that is capable of analyzing the content of the spot. The detector determines the presence of a property inherent to biological particles, thus determining the presence and/or concentration of airborne biological materials, which may include biohazards. Biological materials may be bacteria and/or viral and/or protein aggregates. As bacteria can clump together, the term "particle" as used herein is understood to include inert particles, a single biological entity or biological (typically 0.5-2 μm), or an aggregate of these small biologicals (aggregates of about 2-10 μm).

Any known property inherent to biological particles or to specific subsets of biological particles may be subject to analysis. There are many examples of such properties, sometimes called biological signatures, and they may be detected by optical or non-optical methods. Examples of known useful properties include fluorescence that may be characterized by single or multi-wavelength excitation and/or emission and/or fluorescence lifetime, IR absorption, Raman scattering, mass specters, or terahertz specters. Examples of useful analytical techniques include fluorescence spectroscopy, Fourier-transform infrared spectroscopy, laser induced breakdown spectroscopy or aerosol time-of-flight mass spectrometry, MALDI mass spectrometry, surface enhanced Raman spectroscopy, planar optical waveguide sensing by evanescent waves, or terahertz spectroscopy.

During analysis, the spot produces a signal that is measured by any suitable detection means. Where the signal is detected optically, detection may be accomplished using any optical detector that is compatible with the spectroscopic properties of the produced signal. The assay may involve an increase in an optical signal or a decrease. The optical signal may be based on any of a variety of optical principles, including fluorescence, elastic scattering, light absorbance, polarization, circular dichroism, optical rotation, Raman scattering, and light scattering. Preferably, the optical signal is based on the intrinsic fluorescence of biological particles.

In general, the optical signal to be detected will involve absorbance or emission of light having a wavelength between about 180 nm (ultraviolet) and about 50 μm (far infrared). More typically, the wavelength is between about 200 nm (ultraviolet) and about 800 nm (near infrared). A variety of detection apparatus for measuring light having such wavelengths are known in the art, and will typically involve the use of light filters, photomultipliers, diode-based detectors, and/or charge-coupled detectors (CCD), for example. The optical signal produced by a spot may be based on detection of light having one or more selected wavelengths with defined bandwidths (e.g., 500 nm+/−0.5 nm). Alternatively, the optical signal may be based on the shape or profile of emitted or absorbed light in a selected wavelength range. This profile can measured by an array of narrow bandwidth sensors or with a spectral photometer (such as that sold by Ocean Optics, Inc.) The signals may be recorded with the aid of a computer.

In preferred embodiments the analyzer is a fluorescence detector, which comprises an excitation light source for stimulating the fluorophores on the collection surface and a fluorescence photosensor for measuring the resulting emissions from the spot. The optical signals produced by individual spots may be measured sequentially by iteratively interrogating the deposit with light of different wavelengths and/or measuring different emission characteristics.

In some embodiments, the optical signal measurement will involve light having at least two distinctive wavelengths in order to include an internal control. For example, a first wavelength is used to determine the presence or concentration of biological materials, and a second wavelength is used to determine the presence or concentration of non-biological materials that may interfere with the reading at the first wavelength. An aberration or absence of the signal for the second wavelength is an indication that the sample was improperly prepared, the estimate of concentration of biological particles is unreliable in that cycle, nonbiological airborne materials are present and affect the fluorescence expected from biological particles in the sample, or the analyzer is malfunctioning.

Biological materials are known to contain autofluorescent materials. For example, fluorophores include the aromatic amino acids tryptophan, tyrosine, and phnylalanine, nicotinamide adenine dinucleotide compounds (NADH and NADPH), flavins, and chlorophylls. In addition, cultured bacteria are known to have characteristic fluorescence features distinguishable from wild bacteria. This property may be employed in the design of the biological alarm as biological weapons are typically produced in cultures.

In some embodiments, improved discrimination between biological particles and other non-biological particles is possible by incorporating several excitation wavelengths in sequential manner, thereby interrogating each sample spot multiples times.

Measuring intrinsic fluorescence of particles trapped in a spot requires comparatively less sophisticated equipment than that necessary for similar measurements of particles in an airborne state. Fluorescence emissions are typically higher due to the presence of concentrated fluorophores. Excitation can thus be performed with less powerful sources, for example, depending on the embodiment with typical electric-arc lamp, LED or laser diodes, although any other types of lasers may also be used. For example, laser diodes or LEDs suitable for some embodiments may be obtained from Nichia Corporation, Tokushima, JAPAN. In addition, excitation for longer time periods is possible. In some embodiments, fluorescence spectra can be collected, while in others only peak fluorescence emission is of interest. Additionally, several autofluorescence characteristics can be determined for each spot. For example, as detailed below, fluorescence emitted in response to excitation at about 266 nm, 340 nm, 360 nm and/or 400 nm, may be measured for each spot.

Fluorescence detectors comprise an excitation light source, such as an UV light source, and a fluorescence photosensor for measuring light emitted from a sample in response to excitation. Any light detector can be used as a detection device. Three common detectors are (1) photomultiplier tubes (PMT), (2) avalanche photo-diodes; and (3) solid-state silicon photo diodes. Focusing the light may be important depending on the type of detector that is used. For example, avalanche photo-diodes have relatively small detection surfaces. Consequently, when using avalanche photo-diodes, it is preferable to focus the light so as to direct the light to the avalanche photo-diode's detection surface. Focusing the fluorescence signal to a small sensor is preferable because it will becomes more likely for stray light to miss the sensor. In some cases, smaller sensors have less noise than sensors with larger active areas.

In one embodiment the excitation light source is positioned underneath a horizontal UV transparent impact plate, and the emission sensor is positioned above the plate, as is the collection surface (see FIG. 2). For example, the impaction plate may be shaped as a disk or may otherwise be planar. Accordingly, the impaction plate has a collection surface side, on which the spot forms, and a side opposite to the collection surface side, which may be called the interrogation side. In some embodiments, the impaction plate is made at least in part of a material substantially transparent to ultraviolet radiation. In these embodiments the spot is collected on a UV transparent collection surface. In these embodiments, the impaction plate allows components of UV-based detectors, such as an excitation light source and fluorescence photodetector, to be placed on the two opposite sides of the impaction plate. Thus, the excitation light source may be placed on the interrogation side and the fluorescence photosensor is placed on the collection surface side.

Figure 26:
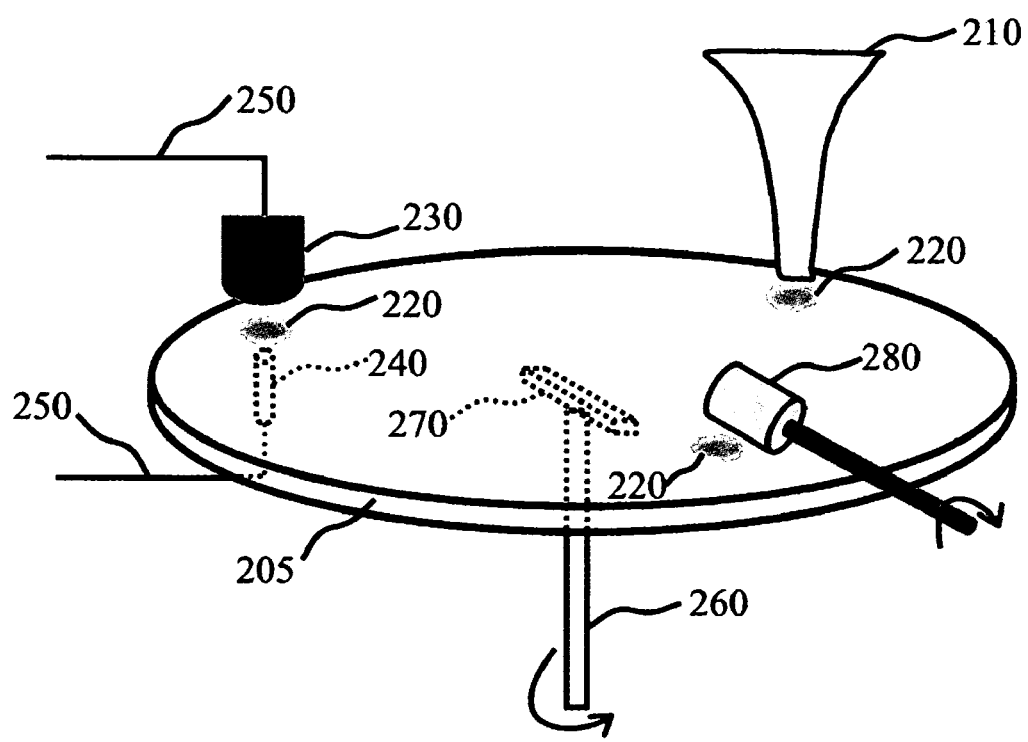
FIG. 26 is a diagram of several components present in various embodiments of the present invention, namely an impaction plate (205) with a collection surface on which a deposit (220) forms, a spotting nozzle (210), an analyzer comprising a fluorescence photosensor (230) and an excitation light source (240) coupled by wires (250), a shaft (260) mounted to the impaction plate (205) by a bracket (270) and a regenerator (280). Three collection surfaces/spots (220) are drawn only for illustration; a single collection surface suffices in most embodiments.

In one embodiment the excitation light source (240) is positioned underneath a horizontal UV transparent impact plate (205), and the emission sensor (fluorescence photosensor 230) is positioned above the plate, as is the collection surface (see FIG. 26). For example, the impaction plate (205) may be shaped as a disk or may otherwise be planar. Accordingly, the impaction plate (205) has a collection surface side, on which the spot (220) forms, and a side opposite to the collection surface side, which may be called the interrogation side. In some embodiments, the impaction plate (205) is made at least in part of a material substantially transparent to ultraviolet radiation. In these embodiments the spot (220) is collected on a UV transparent collection surface. In these embodiments, the impaction plate (205) allows components of UV-based detectors, such as an excitation light source (240) and fluorescence photodetector (photosensor (230)), to be placed on the two opposite sides of the impaction plate. Thus, the excitation light source (240) may be placed on the interrogation side and the fluorescence photosensor (230) is placed on the collection surface side.

Those of skill in the art appreciate that many variables can be optimized, for example angles between the emitter and sensor may be adjusted for maximum signal to noise ratio, filters may be used to reduce or eliminate undesirable wavelengths, or an excitation laser beam may be pulsed and the receiver coupled to the photodetector may be gated to respond in a delayed manner during a short period following each laser illumination pulse, so as to discriminate against false ambient illumination.

The spot is immobilized for an amount of time suitable for multiple analytical measurements. Thus, the intrinsic fluorescence properties of the deposit may be analyzed sequentially at different excitation wavelengths. For example, excitation wavelengths may be of about 266 nm, 340 nm, and/or 400 nm. Excitation at different wavelengths is desirable in some embodiments, as it is expected that non-biological materials also autofluoresce thus interfering with accurate quantification of biological materials present in the spot. Furthermore, it may be possible to distinguish between various classes of biologicals by measuring the fluorescence signature and comparing that signature to known signatures for specific classes of biologicals. For example, by using multiple wavelengths of excitation light and measuring the fluorescence emission spectra over at least several ranges of wavelengths, it may be possible to differentiate bacteria, viruses, bacterial spores, mold spores, and fungi. Within each class, it may be possible to identify cultured from naturally occurring specimens. Thus, a better characterization of biological materials is possible through characterization of fluorescence of airborne particles in response to different excitation wavelengths.

In another embodiment, a particle counter may be used in parallel with a sensor based on a regenerative surface to assist in the characterization of the biologicals. Particle counters use light scattering as particles pass through a beam of light to measure the density particles in air. Some particle counters are also capable of determining the size of each particle. Some particle counters are capable of assessing characteristics of the particle shape based on the particle's light scattering properties. If a particle counter is capable of measuring either or both the size and the shape of many particles in a short period of time, then a dynamic measure of either or both of the particle size distribution and particle shape distribution in air coincident with the particles being analyzed by the sensor based on a regenerative surface. Thus, a better characterization of biological materials is possible through characterization of fluorescence, combined with particle counts broken down by either or both of size and shape.

In another embodiment, two detection methods can be used in sequential combination within a sensor based regenerative surface air sampler to assist in the characterization of the biologicals. For example, after the sample spot is created, the spot may be analyzed sequentially by fluorescence and then by Raman. A Raman sensor may be capable to differentiate various species or genii within a specific class of microbes. Such a combination of sensors would allow for greater confidence in the need to indicate an alarm in response to a particular sample spot.

One useful excitation wavelength is 266 nm, which excites amino acids tryptophan and tyrosine, which have peak emissions around 340 nm and 310 nm respectively. 266 nm UV light also excites NADH and riboflavin, which have emission peaks from airborne particles around 450 nm and 560 nm respectively. In addition to 266 nm, it is feasible to use other close wavelengths, for example 220, 225, 230, 235, 240, 245, 250, 255, 260, 265, 270, 275, 280, 285, 290, or 295 nm. While nonbiological airborne particles within the size range of interest also fluoresce in response to 266 nm UV light, the fluorescence spectra of tryptophan and tyrosine-containing particles exhibit characteristic intensity peaks (between about 310-350 nm; see Pan et al., Field Analytical Chemistry and Technology 3:221-239, 1999). These characteristic peaks can be used to quantitatively distinguish the amount of biological materials relative to non-biological particles which typically have broad emissions spectra. For example, emissions at the expected peak intensity of about 340 may be normalized to emissions at other spectral regions, for example around about 400 nm and/or 500 nm.

Another useful excitation wavelength is about 340 nm. Two related fluorescent coenzymes or biomolecules are found in all living cells: nicotinamide adenine dinucleotide phosphate (NADP) and nicotinamide adenine dinucleotide (NAD). They are essential for cellular metabolism, and therefore their fluorescence can serve to monitor the presence and/or concentration of airborne bacteria. In other words, these measurements are especially suitable for determining the presence and/or concentration of viable airborne cells, such as bacterial cells. The fluorescence excitation and emission wavelengths of NADH are well separated, which facilitates detection. The excitation wavelength of NADH/NAD(P)H is centered at 340 nm in the near ultraviolet spectrum, and their fluorescent emission wavelength extends from 400 to 540 nm. Thus, a desirable excitation wavelength is about 340 nm, but it is feasible to use other close wavelengths, for example 320, 325, 330, 335, 345, 350, 351, 355, 360, 370, 375, or 380 nm.

Riboflavin, a flavonoid, has fluorescent wavebands that partially overlap those of NADH, so it may also be detected by a system designed for NADH, or it may be detected in separate measurements. Riboflavin, exhibits peak excitation at approximately 400 nm, with characteristic emission between 475 nm and 580 nm (Li et al. in Monitoring Cell Concentration and Activity by Multiple Excitation Fluorometry, Biotechnol. Prog., 1991, p:21-27). The presence of both NADH and riboflavin are characteristic of viable bacteria in an air medium. Thus, autofluorescence in response to these wavelengths of excitation can indicate the presence of viable bacteria or cells (see, for example, U.S. Pat. No. 5,895,922, and U.S. patent application Ser. No. 09/993,448). The longer excitation wavelength of less energy also makes it less likely for fluorescence to occur in a wide group of non-biological particles that would interfere with the measurements.

As mentioned above, the detector produces signals, typically electrical signals, which are related to the biological signature detected. The signals are conveyed to a receiver, which may then relay the signals for further processing. The signals typically reach a processor, which may be a computer or a Neuron Chip® as described in more detail below. The processor is capable to process or interpret the signals and thus establish or gauge the concentration of biological particles in the spot. Such signal processing may be performed according to the methods outlined below. Consequently, the processor is capable to establish when the concentration of biological particles in the spot exceeds a predetermined value. In such a case, the processor outputs an alarm signal that alerts users of the presence of potentially harmful airborne biological particles.

In one embodiment, a photodetector is connected to current-to-voltage converter if the photodetector outputs a current proportional to the incident light. This voltage may need amplification to give an output signal in the 0-5 volt range. The signal may require filtration to reduce the noise, thereby increasing the signal to noise ratio. The signal is then fed to an analog-to-digital converter. The digital signal is then read and processed by a microprocessor.

In yet another aspect, the present invention relates to methods of detecting specific airborne particles or monitoring concentrations of airborne biological materials. The methods comprise a plurality of steps, which may be repeated cyclically to ensure continuous monitoring of environmental air.

One step according to the invented methods is depositing airborne particles on a regenerative collection surface to form a spot, which may be accomplished by inertial impaction.

Figure 29:
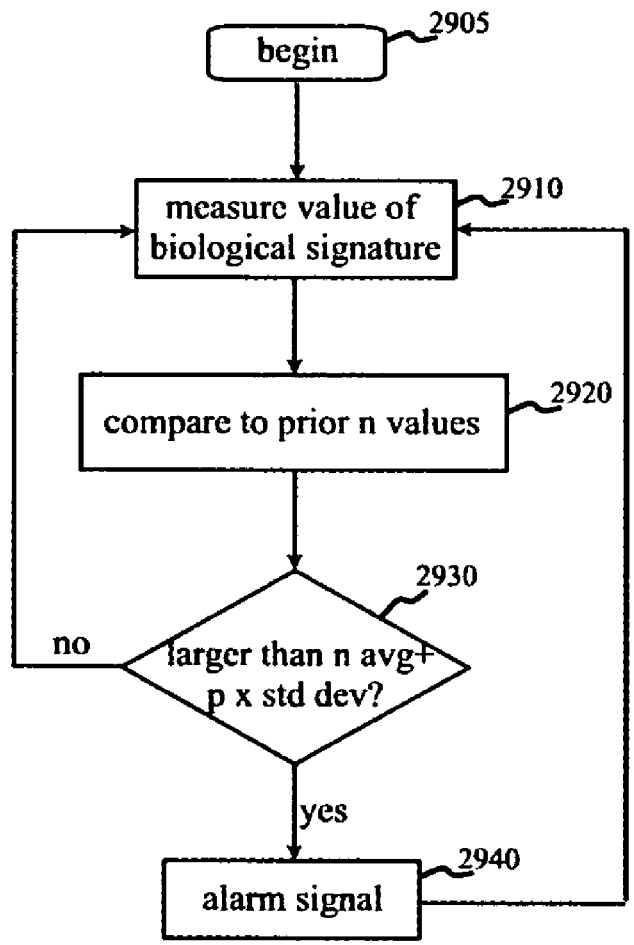
FIG. 29 is a flow diagram of the signal processing for determining the presence unusually high concentrations of airborne biological particles.

Another step comprises measuring a biological signature present in the spot (FIG. 29). Any biological signature and its corresponding measurement known in the art, including those discussed in some detail above, may be utilized at this step. Consequently this measurement indicates the concentration of airborne biological particles. Each measurement performed on a spot deposited on a regenerative surface provides a value of the concentration of airborne biological particles (2910).

Values from a defined number of preceding measurements may be stored temporarily. They can be used in calculating the average value and the standard deviation from prior measurements. Any number of measurements, for example 3, 4, 5, 6, 7, 8, 9, 10 or more, may be used in calculating the average and standard deviation. The number of preceding measurements (n) used in calculations is typically constant.

The value of the last measurement is then compared to the calculated average of preceding measurements to determine if the present value exceeds the average to a significant extent (2920). The standard deviation from the prior measurements can be used to establish if the present value is abnormally high, i.e. if the present value exceeds the average to a significant extent. Thus, the present value may be compared to the average value plus a preset number (p) multiplied by the standard deviation (2930). For example, the preset number may be between 2 and 8, although it may be set at different levels depending on specific operating conditions of the invented methods. If the present value does exceed the average value to a significant extent, then the processor outputs an alarm signal (2940). Other algorithms may also be suitable and by be preferable for specific applications.

Another step is regenerating the collection surface. Then, the processor proceeds to analyze a newly obtained present value from another spot.

In other aspects, the present invention provides sensors, sensor systems and networks based on regenerative surface air samplers. Integrated in various applications, the invented devices and systems are useful for monitoring and controlling air quality, as well as warning promptly of the presence of potentially noxious airborne hazards. Sensors based on regenerative surface air samplers can be adapted to monitor the presence of any airborne hazard. For example, biological, chemical, or radiological sensors can be used to continuously detect the presence of respective particles in the ambient air.

By sensors it is meant devices that are responsive to changes in the quantity to be measured. As used herein sensors may encompass transducers that convert measurements into electrical signals.

Sensors according to the present invention are desirable in a large number of civilian or military contexts. They are especially useful in densely populated and possibly closed areas. For example, they are desirable in buildings or public facilities like stadiums or auditoriums where a large number of people may get simultaneously exposed to airborne hazards. They may be mounted on walls or ceilings, and may be especially useful in air ducts and air plenums, at entrance or delivery points. As such, sensors may interact with HVAC systems, or may be part of HVAC systems. The present sensors may also be useful in any vehicles such as airplanes or cruise ships.

Sensors based on regenerative surface air samplers may be embodied as various types of devices. As those of skill in the art will appreciate, devices attached to sensors may have various types of processing capabilities. Dumb sensors may simply generate analog or digital uncalibrated or calibrated outputs. Smart sensors may fuse or correlate different readings to send a number of different types of alerts, or have communication capabilities and can be programmed to send raw data and/or sets of alerts. Intelligent sensors can additionally reason about how to investigate and resolve their own alerts.

The sensors communicate their signals through a communication interface. In simpler embodiments, the sensors may merely issue a local audio or visual signal. In other embodiments, however, the sensors communicate information through the communication interface to one or more distant locations. The communication interface may be simply a transmitter in some cases, such as with dumb sensors. In other embodiments the communication interface is a transceiver, i.e. a device that is both a transmitter and a receiver for a communications channel.

Signals from and to sensors may be communicated by any known feasible means. As such, signals are communicated through wired or wireless connections. Examples of wired connections include twisted pair, coaxial, power lines, or fiber optic cables. Examples of wireless connections include radio frequency (RF), infrared (IR) communication means. For example, in some embodiments the transceiver communicates via an RF link to an RF link network.

In many embodiments a controller is coupled to the sensor. In some embodiments, the controller is a programmed personal computer or other computer with processor, memory and I/O devices. In some embodiments the controller is a Neuron® chip, a system-on-chip microcontroller used with LonTalk®, LonWorks® communications protocol referred to below. Different chip versions share the same basic features in various combinations: processor cores, memory, communications, and I/O, as well as sensors, actuators, and transceivers. The Neuron® chip is actually three, 8-bit inline processors in one. Two of the processors execute the LONWORKS protocol referred to below, and the third is for the device's application. The chip is, therefore, both a network communications processor and an application processor. Typically, the controller is also coupled to a transceiver. In some embodiments, the function of the controller may be performed by more than one computer or controller, which may be coupled through a network. The controller may incorporate software or firmware used to operate sensors based on regenerative surfaces. The methods of operation embodied in the software or firmware may be substantially similar to the methods of detecting biological particles disclosed herein. The controller may operate or integrate information from other system components as described below.

Signals from the communication interface are typically communicated over a network or system that may be a computer data network, but is more typically a control network, such as a building automation network. There are many examples of systems in which sensors based on regenerative surface air samplers may be integrated. One such system is the CEBus system, which has been made an EIA standard, known as the EIA 600 standard, which was originally developed by Intellon Corp. A second system is the LonWorks system commercially available from and developed by Echelon Corp, San Jose, Calif. Both the CEBus and LonWorks systems specify physical and link layer means for communicating over a variety of different media including power line, coaxial cable, fiber optic cable, radio frequency (RF), infrared (IR) and twisted pair cable. While the sensors may be adapted to communicate by a variety of means, it is preferable that the sensors communicate to a local operating network using a standard protocol, such as the BACnet (ISO standard 16484-5) protocol or the LonTalk® (also known as the ANSI/EIA 709.1 Control Networking Standard) protocol, CEBus, X10 or CAN. Sensors based on regenerative surfaces may also be integrated into any other sensor network, such as the one described in U.S. patent application Ser. No. 10/021,898.

In some embodiments the controller is coupled to at least one actuator and configured to operate at least one air management component in response to information received from the sensor. Thus, in response to a potential hazard indicated by the sensor, the controller may turn on one or more components. It may be useful to activate different types of system components in such situations. The components may be loosely categorized as air analysis devices, air control devices, or self-diagnostic devices. Depending on the configuration of the system, the actuated devices may be near or far from the sensor that issued the original alert, and they may be located indoors or outdoors. The controller may also be communicatively coupled to the air management component, and thus it may be able to receive and integrate information additional to that received from sensors based on regenerative surfaces. Evacuation alarms may be triggered based solely on information from a sensor based on a regenerative surface, or may be triggered based on additional information also available.

Air analysis devices may be any devices known in the art that would be useful in analyzing the composition of air. Examples of suitable devices include a light detection and ranging (Lidar) system, an aerodynamic particle sizer, a mass spectrometer to detect chemicals present in the threat, sample capture and archival devices (as in U.S. patent application Ser. No. 10/366,595) or specific antibody or PCR based sensing to precisely identify agents in the threat. Use of specific sensors may minimize the impact of false alarms. They also provide information valuable for treatment of affected personnel. Sensors of this type perform DNA analysis using the PCR technology, and antibody analysis using antibody-based assays.

Air control devices control the flow of air, such as by operating dampers of an HVAC system. Thus an HVAC system can be used to control the flow of air within a building in response to a threat. If the threat is exterior to the building, air is stopped from entering the building, or air is taken in through alternate air intakes that do not appear to be affected by the threat. If the threat is from within the building, its location can be identified, and air exhausted from the threatened area, while providing fresh, unaffected air to the non affected areas of the building. Other examples of air control devices include UV lights, heat or microwave, HEPA filters, and corona based disinfection, chemical foggers, thermo or photocatalytic filters, or carbon filters.

In some embodiments, sensors based on regenerative surfaces have self-diagnostic capabilities. Operation of various components the regenerative surface sensor may be itself monitored by one or more sensors, which may be coupled to the controller. The controller may turn on a self-diagnostic program either periodically or as part of a response to an alarm by the sensor.

Because sensors based on regenerative surfaces are desirably active in emergency situations, in some embodiments they include a battery backup. Thus, while the sensors are routinely powered from a regular alternative current outlet, they may have a battery backup to be used during power outages.

Data on the control network may be transmitted or accessible to a large number of interested persons, or organizations, or systems, such as facility managers, fire departments or law enforcement agencies, and/or building security systems.

In operation, sensors based on regenerative surfaces operate virtually continuously in a sampling mode. When they detect a high probability of presence of airborne hazards, they issue an alert signal, which may be communicated locally and/or remotely. At the same time, depending on the specific embodiment, the sensors may activate a self-diagnosis program, activate specific sensors, and/or initiate prophylactic measures such as operate air duct dampers to contain the contamination, or increase intake of outside air by the HVAC system.

System components other than sensors based on regenerative surfaces usually operate in a standby mode to conserve power and reagents. They are controlled based on input detection by sensors based on regenerative surfaces and/or other early detection sensors, and are placed in an active mode only when a potential threat is detected. The network provides the ability to tailor sets of sensors based on an area to be protected in combination with different threat scenarios. In the case of a building or other enclosed structure, both large and small releases, as well as slow and fast releases, of agents may occur either internal or external to the structure. The rate of release is also variable. By correct placement of the sensors, each of these scenarios is quickly detected, and appropriate measures may be taken to minimize damage from the threat. The network may provide input to a heating and ventilation system, or the security management system of the structure in a further embodiment to automate the control response.

In another aspect, the present invention relates to methods of constructing a sensors network. Accordingly, sensors based on a regenerative surface air sampler can be added into a network. The sensors may be of biological particles, or may be of other types such as chemical or radiological sensors.

Figure 32:
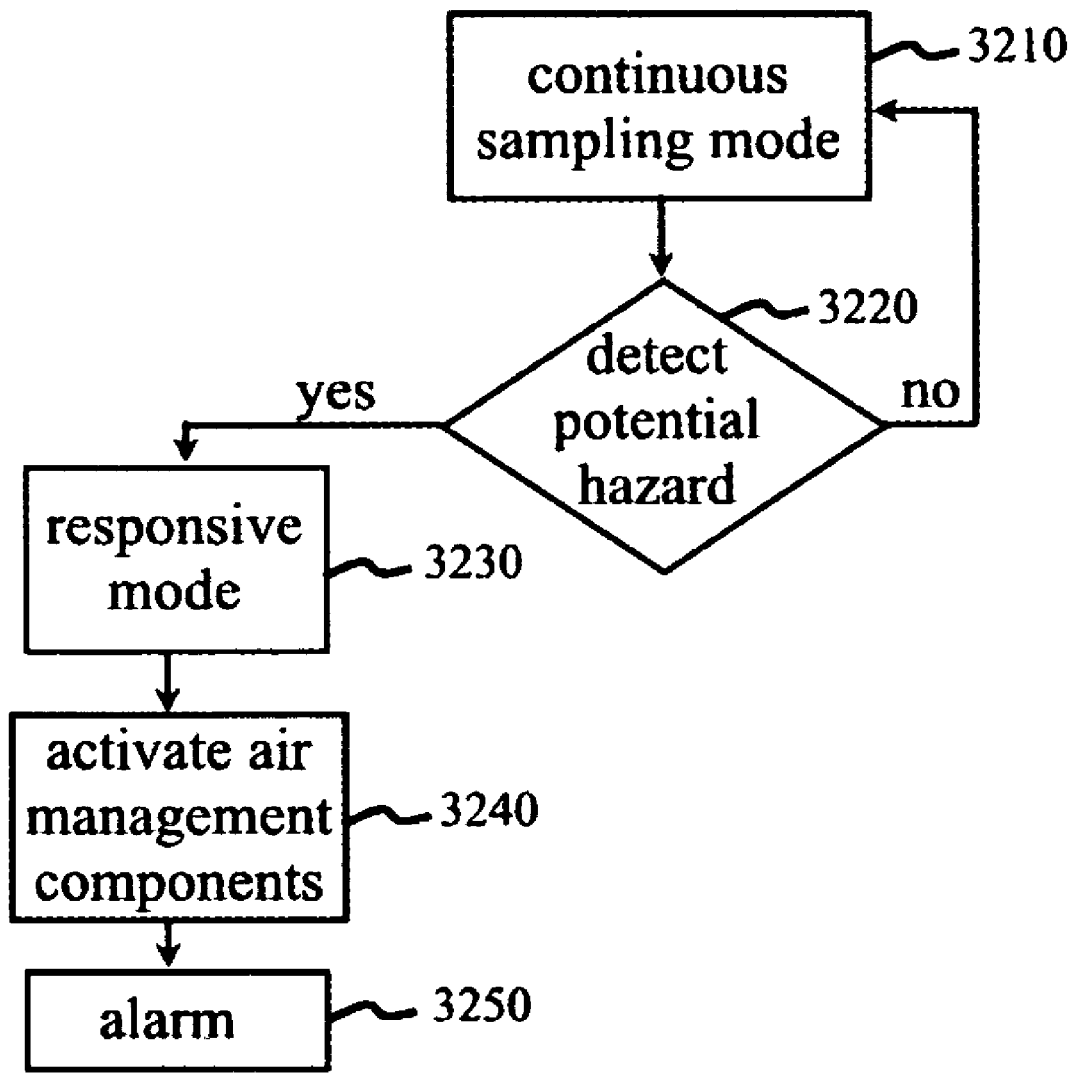
FIG. 32 shows a diagram of a method of controlling ambient air quality.

In yet another aspect the present invention relates to methods of controlling ambient air quality and alerting those potentially affected by airborne hazards (see FIG. 32). According to the invented methods, ambient air is routinely monitored with at least one sensor based on a regenerative surface air sampler in a continuous sampling mode (3210). Sampling can take place continuously and automatically for extended periods of time. As long as no potential hazard is detected (3220) continuous sampling (3210) is performed. If at one time sampling by the sensor indicates a probable threat (3220), at least one responsive action is taken performed (3230). For example, the responsive step may comprise actuating at least one air management component (3240), such as activating at least one specific sensor. A warning signal (3250) may also issued immediately upon initial detection of the hazard or after confirmation of the presence of a hazard at a second location. In case an alert signal is issued, it may be transmitted to one or several locations, such as building controller, facility management, and or a fire department or law enforcement agency.

The invention provides several advantages compared to current related technologies, although all advantages are not necessarily present in every embodiment of the invention. Unlike most extractive techniques, the disclosed invention is automatic and requires little or no consumable items. Consequently, it requires human intervention quite rarely, whether for operation, maintenance or service. The technology is thus user friendly, i.e. its use does not require training. In addition, the cost of employing the invented technology is also kept low because consumables are unnecessary.

Unlike in situ detection methods, the invented technology is inexpensive and even allows a more comprehensive analysis of airborne particles. Because aggregates of particles rather than individual particles are subject to characterization, the technology does not require sophisticated equipment like powerful lasers and very sensitive photon counters. Therefore, the invented technology is more affordable. In addition, immobilization of particles makes possible prolonged analysis or multiple analyses of samples. Hence, the invention is compatible with a more thorough sample analysis and consequent increased reliability.

The invented technology allows affordable, automatic, and user friendly monitoring of airborne particles. Consequently, prolonged monitoring of a large number and variety of premises is feasible. Continuous monitoring even of buildings at low risk of biohazard exposure might make a critical difference because noxious biologicals can have devastating effects. Thus, the invention can minimize exposure of persons and expedite protective measures. Moreover, the technology lends itself to integration with other types of monitoring technologies, for example smoke, chemical, and/or radiological alarms, for comprehensive environmental monitoring solutions. In sum, the invented technology permits widespread adoption of airborne biological detectors, resulting in increased security of a large segment of the human population.

The examples presented below are provided as a further guide to a practitioner of ordinary skill in the art, and are not meant to be limiting in any way.

EXAMPLE

Detection of Aerosolized Fluorescent Particles Using a Regenerative Surface

Figure 28:
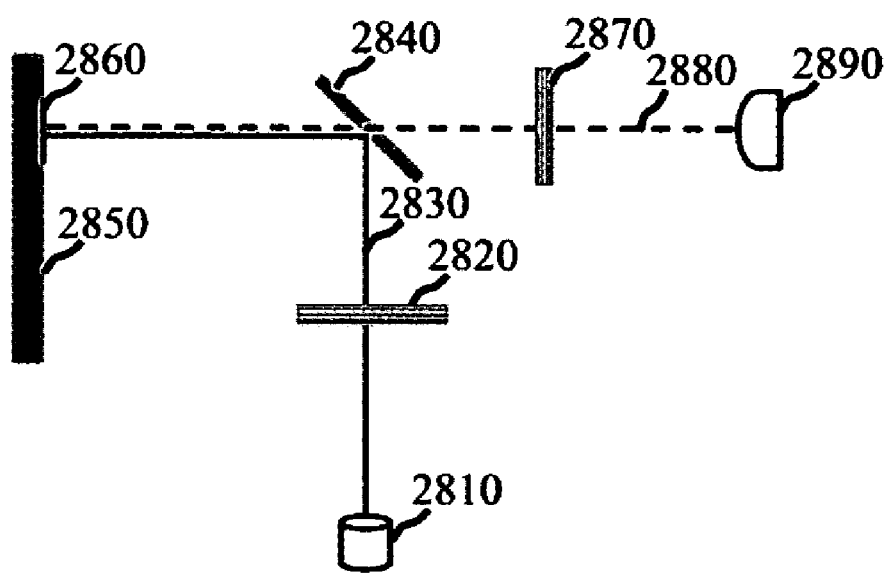
FIG. 28 illustrates an arrangement of the components of a fluorescence detector. A UV LED 2810 emits an excitatory light 2830 that passes through excitation filter 2820. A dichroic mirror reflects the excitatory UV light, which then reaches the sample spot 2860 on a regenerative surface 2850. Fluorescent light 2880 in the visible part of the spectrum passes through the dichroic mirror 2840 and an emission filter 2870 until it reaches the photodiode detector 2890.
Figure 30:
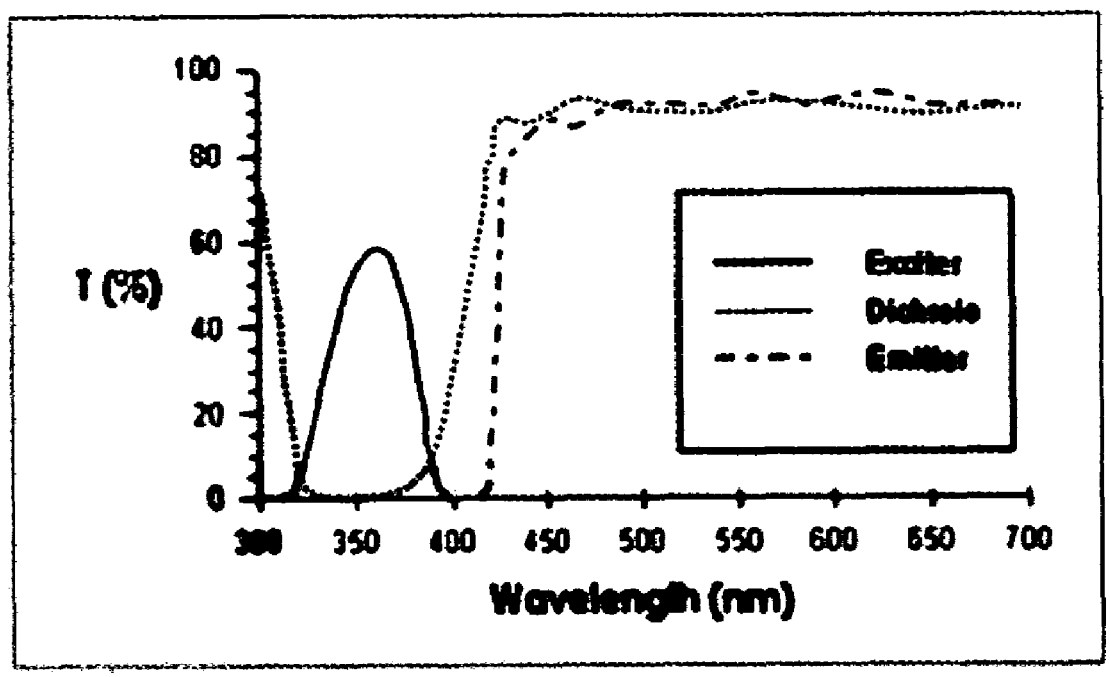
FIG. 30 shows transmission profiles of the dichroic mirror, exciter and emitter filters.

A regenerative surface air sampler based was constructed. The impaction plate was made of aluminum, and was shaped as a lobed cam with three regenerative surfaces. Components of the system included an inertial impactor, a fluorescence detector, and a felt wheel brush surface regenerator. The fluorescence detector was arranged essentially as depicted in FIG. 28, with transmission characteristics of the dichroic mirror, excitation and emission filters as shown in FIG. 30. The UV LED emission was specified to be about 375+/−3 nm.

Biological aerosol was simulated with a fluorescent powder (UVPN UV Powder sold by LDP, LLC (www.maxmax.com)). It was aerosolized by tapping an open envelope of the powder three times, releasing approximately 100 milligrams of the powder into the air several feet away from the air inlet to the sensor.

Figure 31:
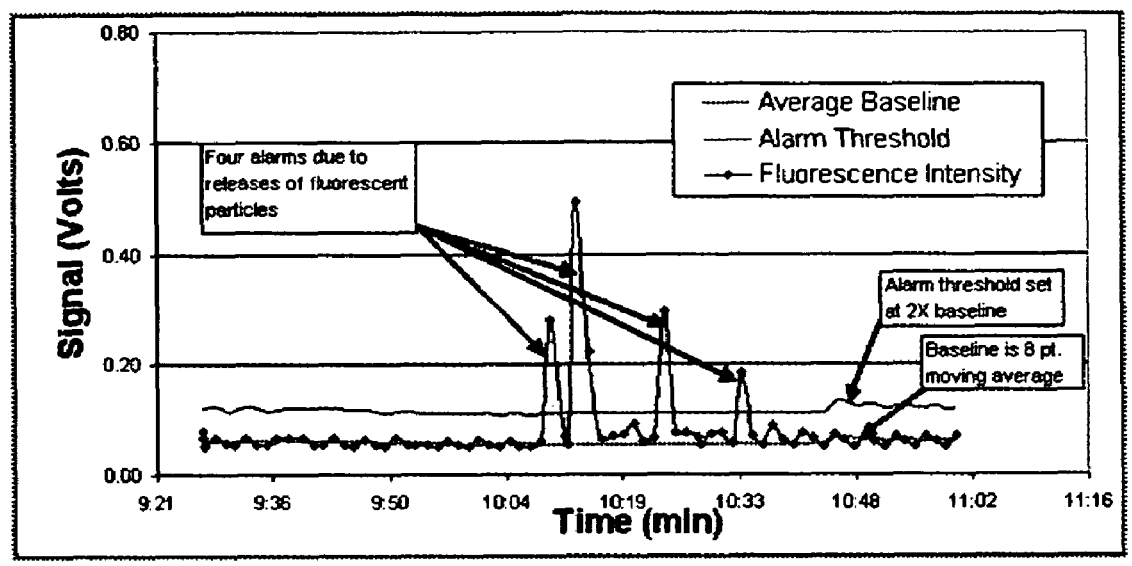
FIG. 31 shows results of testing fluorescent aerosol detection using a regenerative collection surface air sampler.

Results of the test are shown in FIG. 31. As can be seen, the apparatus reliably detected releases of fluorescent particles. It is also noticeable that the baseline value varies slightly for each independent regenerative surface, suggesting that improved accuracy may be achieved using surface specific averages. Note that the algorithm employed for this example holds the baseline at a constant level for the next 10 samples after an alarm.

All cited documents, including patents, patent applications, and other publications are incorporated herein by reference in their entirety.

Foregoing described embodiments of the invention are provided as illustrations and descriptions. They are not intended to limit the invention to the precise form described. Other variations and embodiments are possible in light of above teachings, and it is thus intended that the scope of invention not be limited by this Detailed Description, but rather by the following claims.

What is claimed is:

1. A device comprising:
   an impaction plate,
   a planar collection surface on the impaction plate,
   a spotting nozzle for directing an air stream towards the collection surface, the air stream passing through the spotting nozzle before impacting on the surface to form a spot of airborne particles on the collection surface,
   an analyzer configured to analyze the particles while the particles are retained on the collection surface and the impaction plate remains in the device, the analyzer comprising an optical detector that can analyze the particles as they remain on the collection surface, a surface regenerator for regenerating the collection surface such that particles collected before regenerating the collection surface are removed from the collection surface, and thus are substantially no longer present to contaminate a spot of particles collected after regenerating the collection surface, and a homing sensor, wherein the homing sensor is a mechanical structure configured to cyclically and automatically move the collection surface relative to the nozzle, the analyzer, and the surface regenerator, movement of the collection surface being controlled such that in each successive cycle a first portion of the collection surface will initially be adjacent to the nozzle, then adjacent to the analyzer, then adjacent to the surface regenerator, and then adjacent to the nozzle once again in a subsequent cycle, such that the analyzer and the surface regenerator are disposed proximate to the impaction plate during operation of the device.

2. The device according to claim 1 wherein the collection surface is smooth.

3. The device according to claim 1 wherein the spot is enriched in particles of 1-10 μm size range.

4. The device according to claim 1 wherein the analyzer is a fluorescence detector.

5. The device according to claim 1 wherein the analyzer is an infrared absorbance detector.

6. The device according to claim 1 wherein the analyzer is a mass spectrometer.

7. The device according to claim 1 wherein the analyzer is a surface enhanced Raman spectrometer.

8. The device according to claim 1 wherein the surface regenerator is a felt wheel.

9. The device according to claim 1 wherein the impaction plate comprises a plurality of collection surfaces.

10. The device according to claim 1 further comprising at least one particle concentrator upstream of the nozzle.

11. The device according to claim 1 further comprising a size selective inlet upstream of the nozzle.

12. The device according to claim 1 wherein the impaction plate is a lobed cam having a shaft, the impaction plate comprises at least one planar collection surface substantially parallel to the shaft, and the homing sensor comprises the shaft.

13. A device comprising:
an impaction plate,
a planar collection surface on the impaction plate, said planar collection surface being incorporated into the device,
a spotting nozzle for directing an air stream towards the collection surface, whereby impact of the air stream on the surface forms a spot of airborne particles on the collection surface,
means for analyzing the particles while the particles are retained on the collection surface and without removing the collection surface from the device, said means comprising an optical detector that can analyze the particles while they remain on the collection surface, means for regenerating the collection surface such that particles collected before regenerating the collection surface are removed from the collection surface, and thus are substantially no longer present to contaminate a spot of particles collected after regenerating the collection surface, and means for translocating the collection surface relative to the nozzle, the analyzer, and the surface regenerator, each of said means for analyzing and means for regenerating are disposed proximate the impaction plate during operation of the device.

14. The device according to claim 13 wherein the means of analyzing the spot is selected from the group consisting of means for measuring biological, chemical, and radiological properties.

15. The device according to claim 13 wherein the means of analyzing the spot is a fluorescence detector.

16. The device according to claim 13 wherein the means for regenerating the collection surface comprises a felt pad.

17. The device according to claim 13 further comprising at least one particle concentrator upstream of the nozzle.

18. The device according to claim 13 further comprising a size selective inlet upstream of the nozzle.

19. The device according to claim 13 wherein the impaction plate is a lobed cam having a shaft, the impaction plate comprises at least one planar collection surface substantially parallel to the shaft, and the means of translocating comprises the shaft and a prime mover incorporated into the device.

20. A device comprising:

an impaction plate, a planar collection surface on the impaction plate, a nozzle for directing an air stream towards the collection surface, whereby impact of the air stream on the surface forms a spot of airborne particles on the collection surface, a pre-analysis spot preparation station, an analyzer for examining the particles while the particles are retained on the collection surface and the impaction plate and collection surface remain in the device, a surface regenerator capable of removing the deposit from the surface after analysis such that particles collected before regenerating the collection surface are removed from the collection surface, and thus are substantially no longer present to contaminate a spot of particles collected after regenerating the collection surface, and a homing sensor, wherein the homing sensor is configured to automatically and operatively position the collection surface relative to the nozzle, the analyzer, and the surface regenerator, the homing sensor comprising a prime mover configured to provide a motive force to operatively position the collection surface relative to the nozzle, the analyzer, and the surface regenerator.

21. The device according to claim 20 wherein the surface comprises pyramid-shaped structures of about 1-10 μm in height and width.

22. The device according to claim 20 wherein the surface regenerator comprises a regenerator nozzle for blowing air towards the collection surface.

23. The device according to claim 20 wherein the impaction plate is a lobed cam having a shaft, the impaction plate comprises at least one planar collection surface substantially parallel to the shaft, and the homing sensor comprises the shaft.

24. The device according to claim 20 further comprising at least one particle concentrator upstream of the nozzle.

25. The device according to claim 20 further comprising a size selective inlet upstream of the nozzle.

26. A device comprising:

an impaction plate, a planar collection surface on the impaction plate, said planar collection surface being incorporated into the device, a spotting nozzle for directing an air stream towards the collection surface, whereby impact of the air stream on the surface forms a spot of airborne particles on the collection surface, means for analyzing the particles while the particles are retained on the collection surface and without removing the collection surface from the device, means for regenerating the collection surface such that particles collected before regenerating the collection surface are removed from the collection surface, and thus are substantially no longer present to contaminate a spot of particles collected after regenerating the collection surface, and means for translocating the collection surface relative to the nozzle, the analyzer, and the surface regenerator, said means for translocating the collection surface comprising a shaft attached to the impaction plate, wherein rotation of the shaft by a prime mover incorporated into the device at predetermined angles operatively positions the collection surface to the spotting nozzle, the means for analyzing the spot, and the means for regenerating the collection surface, each of said means for analyzing and means for regenerating are disposed proximate the impaction plate during operation of the device.

27. A device comprising:

an impaction plate, wherein the impaction plate comprises a lobed cam having a shaft, and at least one planar collection surface substantially parallel to the shaft, a spotting nozzle for directing an air stream towards the collection surface, the air stream passing through the spotting nozzle before impacting on the surface to form a spot of airborne particles on the collection surface, an analyzer configured to analyze the particles while the particles are retained on the collection surface, a surface regenerator for regenerating the collection surface such that particles collected before regenerating the collection surface are removed from the collection surface, and thus are substantially no longer present to contaminate a spot of particles collected after regenerating the collection surface, and a homing sensor, wherein the homing sensor is a mechanical structure configured to cyclically and automatically move the collection surface relative to the nozzle, the analyzer, and the surface regenerator, movement of the collection surface being controlled such that in each successive cycle a first portion of the collection surface will initially be adjacent to the nozzle, then adjacent to the analyzer, then adjacent to the surface regenerator, and then adjacent to the nozzle once again in a subsequent cycle, such that said shaft is part of the homing sensor and such that the analyzer and the surface regenerator are disposed proximate to the impaction plate during operation of the device.

* * * * *